US009932338B2

(12) United States Patent
Carzaniga et al.

(10) Patent No.: US 9,932,338 B2
(45) Date of Patent: Apr. 3, 2018

(54) COMPOUNDS HAVING MUSCARINIC RECEPTOR ANTAGONIST AND BETA2 ADRENERGIC RECEPTOR AGONIST ACTIVITY

(71) Applicant: CHIESI FARMACEUTICI S.P.A., Parma (IT)

(72) Inventors: Laura Carzaniga, Parma (IT); Fabio Rancati, Parma (IT); Andrea Rizzi, Parma (IT); Ian Linney, Saffron Walden (GB)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 15/364,669

(22) Filed: Nov. 30, 2016

(65) Prior Publication Data
US 2017/0158694 A1 Jun. 8, 2017

(30) Foreign Application Priority Data

Dec. 3, 2015 (EP) .................... 15197730

(51) Int. Cl.
*A61K 31/44* (2006.01)
*C07D 471/08* (2006.01)
*A61K 31/4704* (2006.01)
*A61K 45/06* (2006.01)
*C07D 401/12* (2006.01)
*C07D 405/14* (2006.01)
*C07D 409/12* (2006.01)
*C07D 409/14* (2006.01)
*A61K 31/4709* (2006.01)

(52) U.S. Cl.
CPC ........ *C07D 471/08* (2013.01); *A61K 31/4704* (2013.01); *A61K 31/4709* (2013.01); *A61K 45/06* (2013.01); *C07D 401/12* (2013.01); *C07D 405/14* (2013.01); *C07D 409/12* (2013.01); *C07D 409/14* (2013.01)

(58) Field of Classification Search
USPC ........................................................ 514/299
See application file for complete search history.

(56) References Cited

U.S. PATENT DOCUMENTS 9,662,323 B2 * 5/2017 Carzaniga .......... A61K 31/4709

FOREIGN PATENT DOCUMENTS

| WO | 2012/168349 | 12/2012 |
|----|-------------|---------|
| WO | 2012/168359 | 12/2012 |
| WO | 2014/086927 | 6/2014 |

OTHER PUBLICATIONS

International Search Report issued in Application No. PCT/EP2016/079064 dated Mar. 10, 2017.
European Search Report in Application No. 15197730.3 dated May 30, 2016.

* cited by examiner

*Primary Examiner* — Rei Tsang Shiao
(74) *Attorney, Agent, or Firm* — Oblon, McClelland, Maier & Neustadt, L.L.P.

(57) ABSTRACT

Compounds of formula (I), defined herein, act both as muscarinic receptor antagonists and beta2 adrenergic receptor agonists and are useful for the prevention and/or treatment of broncho-obstructive or inflammatory diseases.

17 Claims, No Drawings

COMPOUNDS HAVING MUSCARINIC RECEPTOR ANTAGONIST AND BETA2 ADRENERGIC RECEPTOR AGONIST ACTIVITY

CROSS REFERENCES TO RELATED APPLICATIONS

This application claims priority to European Patent Application No. 15197730.3, filed on Dec. 3, 2015, which is incorporated herein by reference in its entirety.

BACKGROUND OF THE INVENTION

Field of the Invention

The present invention relates to compounds which act both as muscarinic receptor antagonists and beta2 adrenergic receptor agonists. The present invention further relates to processes for the preparation of such a compound, compositions containing such a compound, therapeutic uses of such a compound, and combinations of such a compound with other pharmaceutical active ingredients.

Discussion of the Background

Pulmonary disorders, such as asthma and chronic obstructive pulmonary disease (COPD), are commonly treated with bronchodilators. A well-known class of bronchodilators consists of beta-2 adrenergic receptor agonists, such as salbutamol, fenoterol, formoterol and salmeterol. These compounds are generally administered by inhalation.

Another well-known class of bronchodilators consists of muscarinic receptor antagonists (anticholinergic compounds), such as ipratropium and tiotropium. These compounds are also typically administered by inhalation.

Inhaled formulations of both beta-2 agonists and muscarinic receptor antagonists are valuable agents in the treatment of asthma and COPD, with both classes of agents providing symptomatic relief due to their ability to relax constricted airways. Observations that the bronchodilator effects of the two classes of agents were additive, prompted studies with combinations of the two agents. In 1975, it was shown that beneficial effects could be achieved by combining two ingredients such as fenoterol and ipratropium bromide in a single aerosol. This prompted the development of fixed dose combinations of ipratropium bromide firstly with fenoterol (Berodual, introduced in 1980), and then with salbutamol (Combivent, introduced in 1994).

More recently the availability of both long-acting muscarinic antagonists and long-acting beta-2 agonists prompted to the development of combinations of these agents.

For example, WO 00/69468, which is incorporated herein by reference in its entirety, discloses medicament compositions containing a muscarinic receptor antagonist, such as tiotropium bromide, and beta-2 adrenergic receptor agonists, such as formoterol fumarate or salmeterol, and WO 2005/115467, which is incorporated herein by reference in its entirety, discloses a combination which comprises a beta-2 agonist and an antagonist of M3 muscarinic receptors which is a salt of 3(R)-(2-hydroxy-2,2-dithien-2-ylacetoxy)-1-(3-phenoxypropyl)-1-azoniabicyclo[2.2.2]octane.

An alternative approach to the development of fixed dose combinations is the identification of molecules that combine both activities of muscarinic antagonism and beta-2 agonism. In fact compounds possessing both beta-2 adrenergic receptor agonist and muscarinic receptor antagonist activity are highly desirable since such bifunctional compounds would provide bronchodilation through two independent mechanisms of action while having a single molecule pharmacokinetics.

Such kind of compounds was described in some patent applications, such as WO 2004/074246, WO 2004/074812, WO 2005/051946, WO 2006/023457, WO 2006/023460, WO 2010/123766, and WO 2011/048409, all of which are incorporated herein by reference in their entireties, and co-pending patent applications from the same Applicant WO 2012/168349, WO 2012/168359, WO 2014/086924, and WO 2014/086927, all of which are incorporated herein by reference in their entireties.

However, there remains a need for compounds which act both as muscarinic receptor antagonists and beta2 adrenergic receptor agonists.

SUMMARY OF THE INVENTION

Accordingly, it is one object of the present invention to provide novel compounds which act both as muscarinic receptor antagonists and beta2 adrenergic receptor agonists.

It is another object of the present invention to provide novel processes for the preparation of such a compound.

It is another object of the present invention to provide compositions which contain such a compound.

It is another object of the present invention to provided novel therapeutic uses of such a compound.

It is another object of the present invention to provided novel combinations of such a compound with other pharmaceutical active ingredients among which are, for instance, those currently used in the treatment of respiratory disorders, e.g., corticosteroids, P38 MAP kinase inhibitors, IKK2, HNE inhibitors, PDE4 inhibitors, leukotriene modulators, NSAIDs, and mucus regulators These and other objects, which will become apparent during the following detailed description, have been achieved by the inventors' discovery that some indane carboxylate derivatives, besides possessing both beta-2 adrenergic receptor agonist and muscarinic receptor antagonist activity, possess elevated affinity for the M3 muscarinic receptors and long lasting bronchodilating activity.

Thus, provides compounds of general formula I, which act both as muscarinic receptor antagonists and beta2 adrenergic receptor agonists.

DETAILED DESCRIPTION OF THE PREFERRED EMBODIMENTS

In particular, the invention is directed to compounds of general formula (I)

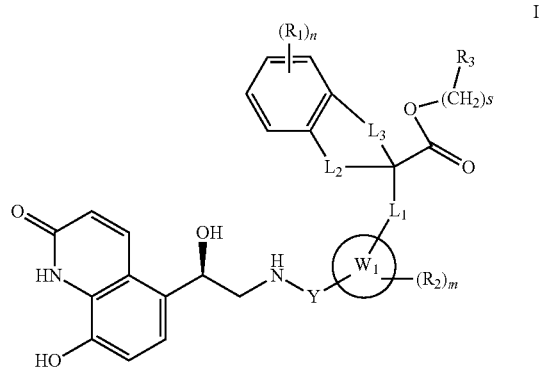

wherein
Y is a divalent group of formula

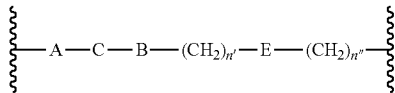
Y wherein
A is selected from the group consisting of $(C_1-C_6)$alkylene;
B is absent or is selected from the group consisting of $(C_3-C_8)$cycloalkylene, $(C_3-C_8)$heterocycloalkylene, arylene or heteroarylene optionally substituted by one or more groups selected from halogens, —CN, $(C_1-C_6)$alkyl, $(C_1-C_6)$alkoxy and aryl$(C_1-C_6)$alkyl;
C is absent or is selected from the group consisting of —O—, —C(O)—, —OC(O)—, —(O)CO—, —S—, —S(O)—, —S(O)$_2$— and —N(R$_5$)—
n' and n" are at each occurrence independently 0 or an integer from 1 to 3;
E is absent or is selected from —O—, —NR$_5$—, —NR$_5$—C(O)—, —C(O)—NR$_5$—, —OC(O)— and —S—;
W$_1$ is selected from a divalent arylene and a divalent heteroarylene group;
R$_1$ and R$_2$ when present are in each occurrence independently selected from halogen, $(C_1-C_6)$alkyl and $(C_1-C_6)$alkoxy; wherein n and m are in each occurrence independently 0 or an integer ranging from 1 to 3;
L$_1$ is a group selected from: —(CH$_2$)$_t$—NR$_5$—, —(CH$_2$)$_t$—C(O)—NR$_5$—, —C(O)—NR$_5$—(CH$_2$)$_t$—C(O)—NR$_5$—; wherein t is an integer ranging from 0 to 4;
L$_2$ is —(CH$_2$)$_q$— and L$_3$ is —(CH$_2$)$_{2-q}$—; wherein q is an integer ranging from 0 to 2;
s is an integer ranging from 0 to 3,
R$_3$ is a nitrogen containing group which is selected from J1, J2, J3 and J4

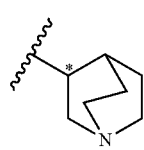
J1

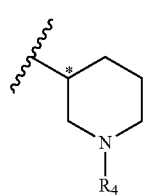
J2

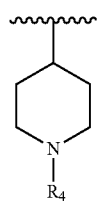
J3

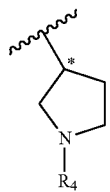
J4

R$_4$ is a group of formula K

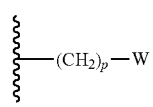
K wherein p is 0 or an integer from 1 to 4; and W is selected from the group consisting of H, $(C_1-C_6)$alkyl, $(C_3-C_8)$cycloalkyl, aryl and heteroaryl, optionally substituted by one or more substituents selected independently from the group consisting of halogen atoms, —OH, oxo (=O), —SH;
R$_5$ is in each occurrence independently selected from the group consisting H, linear or branched $(C_1-C_6)$alkyl, $(C_3-C_8)$cycloalkyl, $(C_3-C_8)$heterocycloalkyl, aryl, heteroaryl;
and pharmaceutically acceptable salts or solvates thereof.

The expression "$(C_1-C_x)$alkyl" refers to straight or branched chain alkyl groups wherein the number of carbon atoms is from 1 to x, for examples it refers to "$(C_1-C_6)$alkyl" wherein x is from 1 to 6. Examples of groups are methyl, ethyl, n-propyl, isopropyl, t-butyl, pentyl, hexyl; when x>6 examples are octyl, nonyl, decyl, undecyl, dodecyl and the like.

In an analogous manner, the expression "$(C_1-C_x)$alkylene" herewith refers to divalent groups, wherein the number of carbon atoms is from 1 to x, for examples it refers to "$(C_1-C_6)$alkylene" wherein x is from 1 to 6. Examples of such groups are methylene, ethylene, n-propylene, isopropylene, t-butylene, pentylene, hexylene; when x>6 examples are, octylene, nonylene, decylene, undecylene, dodecylene and the like. With alternative common name, deriving from the name of the corresponding alkanes, the above divalent groups can be referred to also as methanediyl, ethanediyl, n-propanediyl, propan 1,2diyl and the like.

The expression "$(C_1-C_x)$alkoxy" refers to alkyl-oxy (i.e. alkoxy) groups, being the alkyl portion as above defined, wherein the number of carbon atoms is from 1 to x. For example it refers to "$(C_1-C_6)$alkoxy" groups wherein x is from 1 to 6. Examples of said groups comprise methoxy, ethoxy, n-propoxy, isopropoxy, n-butoxy, isobutoxy, sec-butoxy, tert-butoxy, pentoxy, hexoxy and the like.

The expression "$(C_1-C_x)$alkylamino" refers to alkylamino (i.e. alkylamino) groups, being the alkyl portion as above defined, wherein the number of carbon atoms is from 1 to x. Examples of said groups comprise methylamino, ethylamino, n-propylamino, isopropylamino, n-butylamino, isobutylamino, sec-butylamino, tert-butylamino, pentylamino, hexylamino, and the like.

The expression "$(C_3-C_8)$cycloalkyl" refers to mono or bi-cycloaliphatic hydrocarbon groups with 3 to 8 carbon atoms. Examples include cyclopropyl, cyclobutyl, cyclopentyl, cyclohexyl, cycloheptyl, bicyclo[2.2.1]hept-2-yl and the like.

The expression "($C_3$-$C_8$)heterocycloalkyl" refers to saturated or partially saturated monocyclic ($C_3$-$C_8$)cycloalkyl groups, in which at least one ring carbon atom is replaced by a heteroatom or heteroaromatic group (e.g., N, NH, S or O). Examples include quinuclidinyl, pyrrolidinyl, piperidinyl, azabicyclo[3.2.1]octan-3-yl and azoniabicyclo[2.2.2]octanyl, [1.2.3.6]tetrahydropyridin-1yl and the like.

In an analogous manner, the expressions "($C_3$-$C_8$)cycloalkylene" and "($C_3$-$C_8$)heterocycloalkylene" herewith refer to divalent groups. The term cycloalkylene refers to saturated cycloalkane-diyl and partially saturated monocyclic groups such as cycloalkene-diyl. Examples of such ($C_3$-$C_8$)cycloalkylene and ($C_3$-$C_8$)heterocycloalkylene are divalent groups, such as, respectively, cyclopropylene, cyclobutylene, cyclopentylene, cyclohexylene, cycloheptylene, bicyclo[2.2.1]hept-2-ylene and quinuclidinylene, pyrrolidinylene, piperidinylene, azabicyclo[3.2.1]octan-3-ylene, azoniabicyclo[2.2.2]octanylene, [1.2.3.6]tetrahydropyridine[1.4]diyl and the like. With alternative common name, deriving from the name of the corresponding alkanes or alkenes, the above divalent groups can be referred to also as cyclopropanediyl, cyclobutanediyl, cyclopentanediyl, cyclohexanediyl, cycloheptanediyl, bicyclo[2.2.1]heptanediyl and quinuclidinediyl, pyrrolidinediyl, piperidinediyl, azabicyclo[3.2.1]octanediyl, azoniabicyclo[2.2.2]octanediyl, [1.2.3.6]tetrahydropyridine-[1.4]diyl and the like.

The expression "aryl" refers to mono, bi- or tricyclic ring systems having 5 to 20, preferably from 5 to 15, more preferably from 5 to 8 ring atoms, and wherein at least one ring is aromatic.

The expression "heteroaryl" refers to mono, bi- or tricyclic systems with 5 to 20 ring atoms, preferably from 5 to 15, in which at least one ring is aromatic and in which at least one carbon ring atom is a heteroatom or heteroaromatic group (e.g., N, NH, S or O).

Examples of suitable aryl or heteroaryl monocyclic systems include, for instance, thiophene (thiophenyl), benzene (phenyl), pyrrole (pyrrolyl), pyrazole (pyrazolyl), imidazole (imidazolyl), isoxazole (isoaxzolyl), oxazole (oxazolyl), isothiazole (isothiazolyl), thiazole (thiazolyl), pyridine (pyridinyl), imidazolidine (imidazolidinyl), furan (furanyl) radicals and the like.

Examples of suitable aryl or heteroaryl bicyclic systems include naphthalene (naphthalenyl), biphenylene (biphenylenyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydro-indene, dihydrobenzo dioxepin, benzo oxazine radicals and the like.

Examples of suitable aryl or heteroaryl tricyclic systems include fluorene radicals as well as benzocondensed derivatives of the aforementioned heteroaryl bicyclic systems. In an analogous manner, the expressions "arylene" and "heteroarylene" refer to divalent groups, such a phenylene, biphenylene and thienylene. Such groups are also commonly named as "arenediyl" or "heteroarenediyl" groups. For example o-phenylene is also named benzene-1,2-diyl. Thienyl-ene is alternatively named thiophenediyl.

The expressions "aryl($C_1$-$C_6$)alkyl", and analogously "heteroaryl($C_1$-$C_6$)alkyl" and "($C_3$-$C_8$)cycloalkyl($C_1$-$C_6$)alkyl" refer to a "($C_1$-$C_6$)alkyl" respectively substituted by one or more aryl, heteroaryl or ($C_3$-$C_8$)cycloalkyl groups, as defined above. Examples of aryl($C_1$-$C_6$)alkyl include triphenylmethyl.

As used herein an oxo moiety is represented by (O) as an alternative to other common representations, e.g., (=O). Thus, in terms of general formula, the carbonyl group is herein preferably represented as —C(O)— as an alternative to the other common representations such as —CO—, —(CO)— or —C(=O)—. In general, the group in parentheses is a lateral group, not included into the chain, and brackets are used, when deemed useful, to help disambiguating linear chemical formulas; e.g., the sulfonyl group —$SO_2$— might be also represented as —$S(O)_2$— to disambiguate e.g., with respect to the sulfinic group —S(O)O—.

Whenever basic amino or quaternary ammonium groups are present in the compounds of formula I, physiological acceptable anions, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate may be present. Likewise, in the presence of acidic groups such as —COOH groups, corresponding physiological cation salts may be present as well, for instance including alkaline or alkaline earth metal ions.

In a first preferred embodiment the invention is directed compounds of general formula I wherein $R_3$ is a group of formula J1:

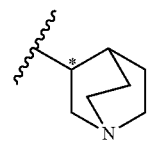

J1 and all the other variables as defined above.

In this first embodiment, the compounds of formula I, wherein $R_3$ is a group of formula J1 whose absolute configuration is R, are particularly preferred.

A second preferred group of compounds is that of general formula I wherein $R_3$ is a nitrogen-containing group selected from J2, J3 or J4

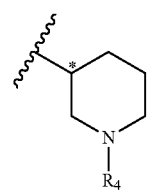

J2

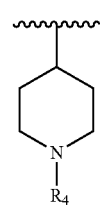

J3

-continued

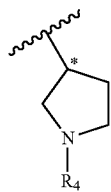

wherein $R_4$ is a group of formula K

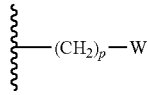

wherein p is 0 or 1 and W is H or is selected from $(C_1-C_6)$alkyl, $(C_3-C_8)$cycloalkyl aryl and heteroaryl optionally substituted by hydroxyl and all the other variables are as defined above.

In a further preferred embodiment, $R_3$ is a group of formula J3, $R_4$ is benzyl optionally substituted by —OH, and all the other variables are as defined above.

In another preferred embodiment the invention is directed to group of compounds of formula I wherein q is 0 or 2 giving a group of compounds of formula Ia:

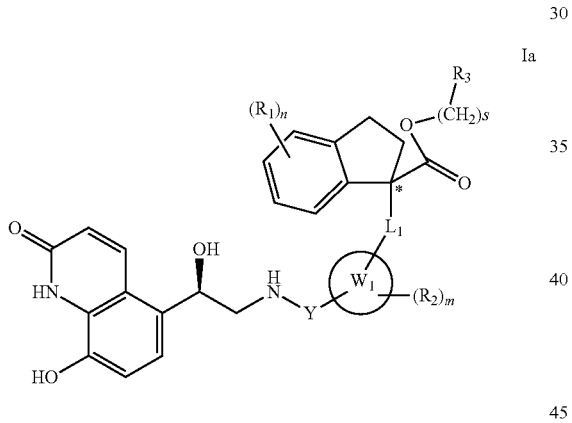

wherein
Y is a divalent group of formula $$\begin{array}{c} Y \\ \xi\text{—A—C—B—}(CH_2)_{n'}\text{—E—}(CH_2)_{n''}\text{—}\xi \end{array}$$

A is selected from the group consisting of $(C_1-C_6)$alkylene, which is methylene, butylene, pentylene or hexylene;
B is absent or is an arylene which is phenylene;
C is absent or is —O—;
n' and n" are at each occurrence independently 0 or 1;
E is absent or is selected from —O—, —NR$_5$—C(O)— and —C(O)—NR$_5$—;
$W_1$ is selected from an arylene which is phenylene and a heteroarylene which is thiophenediyl;
$R_1$ when present is $(C_1-C_6)$alkyl which is methyl; $R_2$ when present is $(C_1-C_{10})$alkoxy which is methoxyl; n and m are in each occurrence independently 0 or 1;

$L_1$ is a group selected from —(CH$_2$)$_t$—NR$_5$— which is —CH$_2$—NH—, —(CH$_2$)$_t$—C(O)—NR$_5$— which is —C(O)—NH— or CH$_2$—C(O)—NH— and —C(O)—NR$_5$—(CH$_2$)$_t$C(O)—NR$_5$— which is —C(O)—NH—(CH$_2$)$_2$—C(O)—NH—;
s is 0 or 1;
$R_3$ is a nitrogen containing group which is selected from J1, J2, J3 and J4

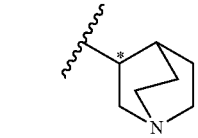

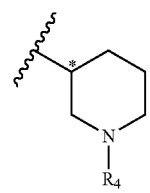

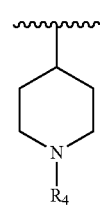

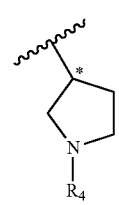

$R_4$ is a group of formula K

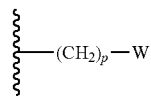

wherein p is 0 or 1; and W is selected from the group consisting of H, $(C_1-C_6)$alkyl which is isopropyl, $(C_3-C_8)$ cycloalkyl which is cyclopentyl, aryl which is phenyl and heteroaryl which is thienyl or furanyl, optionally substituted by an —OH;
$R_5$ is in each occurrence H;
and pharmaceutically acceptable salts or solvates thereof.

In another preferred embodiment the invention is directed to compounds of general formula I wherein q is 1 giving a group of compounds of formula Ib:

wherein
Y is a divalent group of formula $$\text{─A─C─B─(CH}_2)_{n'}\text{─E─(CH}_2)_{n''}\text{─}$$

wherein
A is a (C$_1$-C$_6$)alkylene which is butylene or pentylene;
B is absent;
C is absent;
n' and n" are 0;
E is —O— or —NR$_5$—C(O)—;
W$_1$ is selected from an arylene which is phenylene and a heteroarylene which is thiophenediyl;
n and m are 0;
L$_1$ is —(CH$_2$)$_1$—NR$_5$— wherein t is 1 or —(CH$_2$)$_t$—C(O)—NR$_5$— wherein t is 0;
s is 0,
R$_3$ is a nitrogen containing group which is J1

R$_5$ is in each occurrence H;
and pharmaceutically acceptable salts or solvates thereof.

In this embodiment, the compounds of formula Ib, wherein R$_3$ is a group of formula J1 whose absolute configuration is R, are particularly preferred Compounds of formula I wherein R$_3$ is a group selected from J1, J2, or J4 contain at least two stereogenic centers.

The symbol * is used to indicate a stereogenic center. Therefore, the invention also includes any of the optical stereoisomers, diastereoisomers and mixtures thereof, in any proportion.

Thus, compounds of the present invention having at least two stereogenic centers may exist as at least four diastereoisomers. Where the compounds according to the invention possess more than two stereogenic centers, they will exist as $2^n$ diastereoisomers (wherein n here refers to the number of stereogenic centers). It is to be understood that all such isomers and mixtures thereof in any proportion are encompassed within the scope of the present invention.

The present invention is also directed to a process for the preparation of the compounds of general formula I.

The present invention also provides pharmaceutical compositions of compounds of formula I alone or in combination with or in admixture with one or more pharmaceutically acceptable carriers and/or excipients.

The present invention also provides the use of compounds of formula I for preparing a medicament.

In a further aspect, the present invention provides the use of compounds of formula I for the prevention and/or treatment of any broncho-obstructive or inflammatory disease, preferably asthma or chronic bronchitis or chronic obstructive pulmonary disease (COPD).

In a further aspect, the present invention provides the use of compounds of formula I for the manufacture of a medicament for the prevention and/or treatment of any broncho-obstructive or inflammatory disease, preferably asthma or chronic bronchitis or chronic obstructive pulmonary disease (COPD).

The present invention further provides a method for prevention and/or treatment of any broncho-obstructive or inflammatory disease, preferably asthma or chronic bronchitis or chronic obstructive pulmonary disease (COPD), which comprises administering to a subject in need thereof a therapeutically effective amount of a compound of general formula I.

The present invention also provides pharmaceutical compositions suitable for administration by inhalation.

Inhalable preparations include inhalable powders, propellant-containing metering aerosols or propellant-free inhalable formulations.

The present invention is also directed to a device which may be a single- or multi-dose dry powder inhaler, a metered dose inhaler and a soft mist nebulizer comprising the compounds of formula I.

The present invention is also directed to a kit comprising the pharmaceutical compositions of compounds of formula I alone or in combination with or in admixture with one or more pharmaceutically acceptable carriers and/or excipients and a device which may be a single- or multi-dose dry powder inhaler, a metered dose inhaler and a soft mist nebulizer comprising the said combination or admixture.

According to specific embodiments, the invention provides the compounds reported below:

| No | CHEMICAL NAME |
|---|---|
| 1 | (R)-quinuclidin-3-yl 1-((3-((4-(((R)-2-hydroxy-2-(8-hydroxy-2-oxo-1,2-dihydroquinolin-5-yl)ethyl)amino)butyl)carbamoyl)benzyl)amino)-2,3-dihydro-1H-indene-1-carboxylate |
| 2 | (R)-quinuclidin-3-yl 1-(3-((5-(((R)-2-hydroxy-2-(8-hydroxy-2-oxo-1,2-dihydroquinolin-5-yl)ethyl)amino)pentyl)oxy)benzamido)-2,3-dihydro-1H-indene-1-carboxylate |
| 3 | (R)-quinuclidin-3-yl 1-((3-((5-(((R)-2-hydroxy-2-(8-hydroxy-2-oxo-1,2-dihydroquinolin-5-yl)ethyl)amino)pentyl)oxy)benzyl)amino)-2,3-dihydro-1H-indene-1-carboxylate |

| No | CHEMICAL NAME |
|---|---|
| 4 | (R)-quinuclidin-3-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate |
| 5 | (R)-quinuclidin-3-yl 1-((3-((4-(((R)-2-hydroxy-2-(8-hydroxy-2-oxo-1,2-dihydroquinolin-5-yl)ethyl)amino)butyl)carbamoyl)benzyl)amino)-4-methyl-2,3-dihydro-1H-indene-1-carboxylate |
| 5A | (R)-quinuclidin-3-yl 1-(3-((5-(((R)-2-hydroxy-2-(8-hydroxy-2-oxo-1,2-dihydroquinolin-5-yl)ethyl)amino)pentyl)oxy)benzamido)-4-methyl-2,3-dihydro-1H-indene-1-carboxylate single diastereoisomer 1 |
| 5B | (R)-quinuclidin-3-yl 1-(3-((5-(((R)-2-hydroxy-2-(8-hydroxy-2-oxo-1,2-dihydroquinolin-5-yl)ethyl)amino)pentyl)oxy)benzamido)-4-methyl-2,3-dihydro-1H-indene-1-carboxylate single diastereoisomer 2 |
| 6 | (R)-quinuclidin-3-yl 1-(3-(4-(((R)-2-hydroxy-2-(8-hydroxy-2-oxo-1,2-dihydroquinolin-5-yl)ethyl)amino)butoxy)benzamido)-2,3-dihydro-1H-indene-1-carboxylate |
| 7 | (1-isopropylpiperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate |
| 8 | (R)-quinuclidin-3-yl 1-(3-((4-(((R)-2-hydroxy-2-(8-hydroxy-2-oxo-1,2-dihydroquinolin-5-yl)ethyl)amino)butyl)carbamoyl)benzamido)-2,3-dihydro-1H-indene-1-carboxylate |
| 9 | (1-benzylpiperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate |
| 10 | (1-(furan-2-ylmethyl)piperidin-4-yl)methyl 1-(3-((6-(((R)-2-hydroxy-2-oxo-1,2-dihydroquinolin-5-yl)ethyl)amino)hexyl)oxy)benzamido)-2,3-dihydro-1H-indene-1-carboxylate |
| 11 | (1-(3-hydroxybenzyl)piperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate |
| 12 | (R)-quinuclidin-3-yl 1-(3-((4-(((R)-2-hydroxy-2-(8-hydroxy-2-oxo-1,2-dihydroquinolin-5-yl)ethyl)amino)butoxy)methyl)benzamido)-2,3-dihydro-1H-indene-1-carboxylate |
| 13 | (R)-quinuclidin-3-yl 2-(3-((5-(((R)-2-hydroxy-2-(8-hydroxy-2-oxo-1,2-dihydroquinolin-5-yl)ethyl)amino)pentyl)oxy)benzamido)-2,3-dihydro-1H-indene-2-carboxylate |
| 14 | (R)-quinuclidin-3-yl 2-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-2-carboxylate |
| 15 | (1-(3-hydroxybenzyl)piperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate |
| 16 | (1-benzylpiperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate |
| 17 | (1-(thiophen-2-ylmethyl)piperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate |
| 18 | (R)-quinuclidin-3-yl 1-(2-(4-(2-((4-((((R)-2-hydroxy-2-(8-hydroxy-2-oxo-1,2-dihydroquinolin-5-yl)ethyl)amino)methyl)phenyl)amino)-2-oxoethyl)phenyl)acetamido)-2,3-dihydro-1H-indene-1-carboxylate |
| 19 | (R)-quinuclidin-3-yl 1-(4-((4-((((R)-2-hydroxy-2-(8-hydroxy-2-oxo-1,2-dihydroquinolin-5-yl)ethyl)amino)methyl)benzyl)oxy)benzamido)-2,3-dihydro-1H-indene-1-carboxylate |
| 20 | (R)-quinuclidin-3-yl 1-((3-((4-((((R)-2-hydroxy-2-(8-hydroxy-2-oxo-1,2-dihydroquinolin-5-yl)ethyl)amino)methyl)benzyl)oxy)benzyl)amino)-2,3-dihydro-1H-indene-1-carboxylate |
| 21 | (R)-quinuclidin-3-yl 1-((3-((3-(4-(((R)-2-hydroxy-2-(8-hydroxy-2-oxo-1,2-dihydroquinolin-5-yl)ethyl)amino)butoxy)benzyl)oxy)benzyl)amino)-2,3-dihydro-1H-indene-1-carboxylate |
| 22 | (1-benzylpiperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate single stereoisomer 1 |
| 23 | (1-benzylpiperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate single stereoisomer 2 |
| 24 | 1-benzylpiperidin-4-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate single stereoisomer 1 |
| 25 | (R)-1-benzylpiperidin-3-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate single stereoisomer 1 |
| 26 | (R)-1-benzylpyrrolidin-3-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate single stereoisomer 1 |

| No | CHEMICAL NAME |
|---|---|
| 27 | 1-benzylpiperidin-4-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate single stereoisomer 2 |
| 28 | (R)-1-benzylpyrrolidin-3-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate single stereoisomer 2 |

The compounds of the present invention can be prepared from readily available starting materials using the following general methods and procedures or by using other information readily available to those of ordinary skill in the art. Although a particular embodiment of the invention may be shown or described herein, those skilled in the art will recognize that all embodiments or aspects of the invention can be prepared using the methods described herein or by using other known methods, reagents and starting materials. It will also be appreciated that where typical or preferred process conditions (i.e., reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by one skilled in the art by routine optimisation procedures.

Compounds of formula I may be prepared according to the following synthetic Schemes 1A and 1B.

Scheme 1A

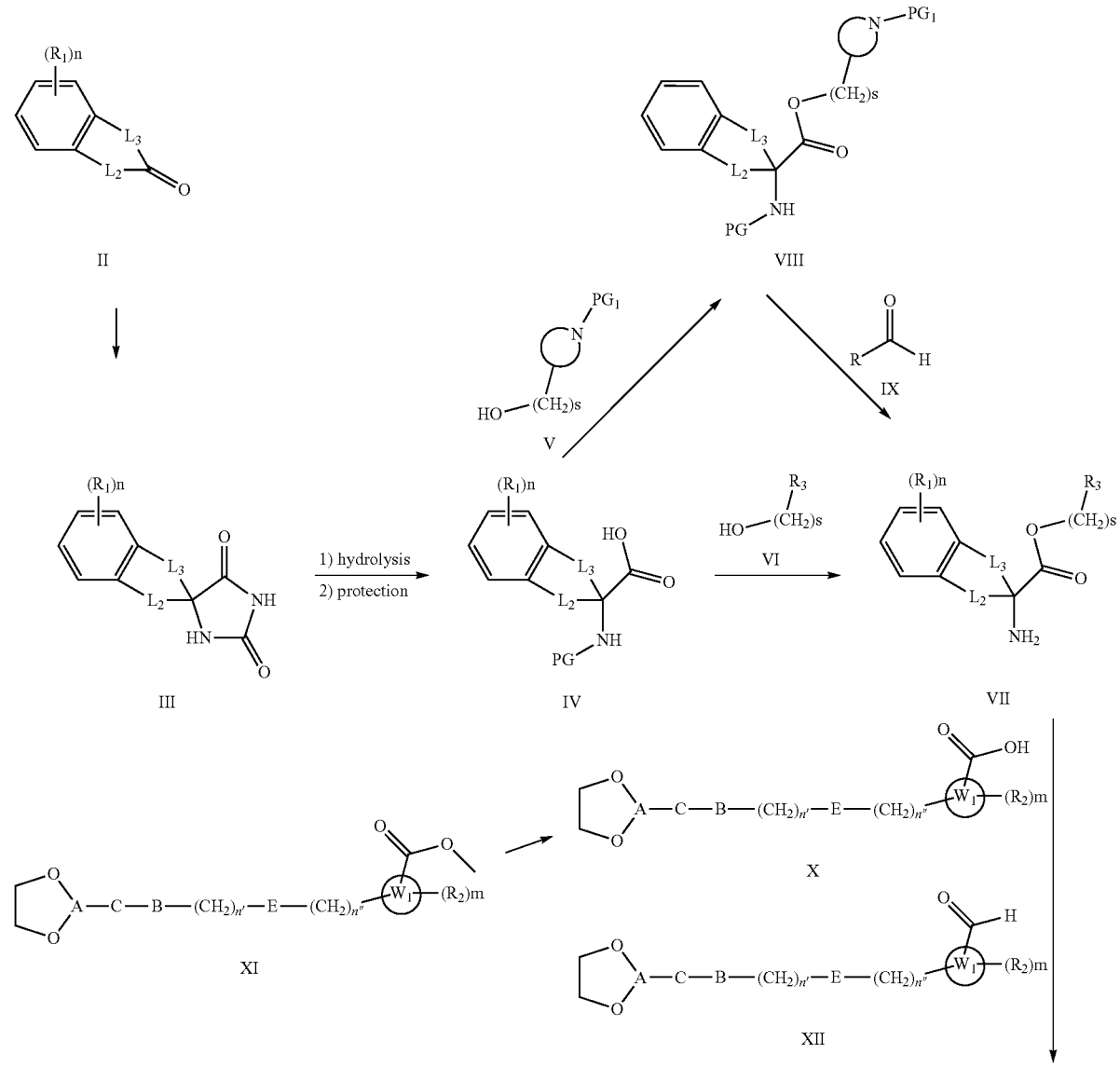

-continued
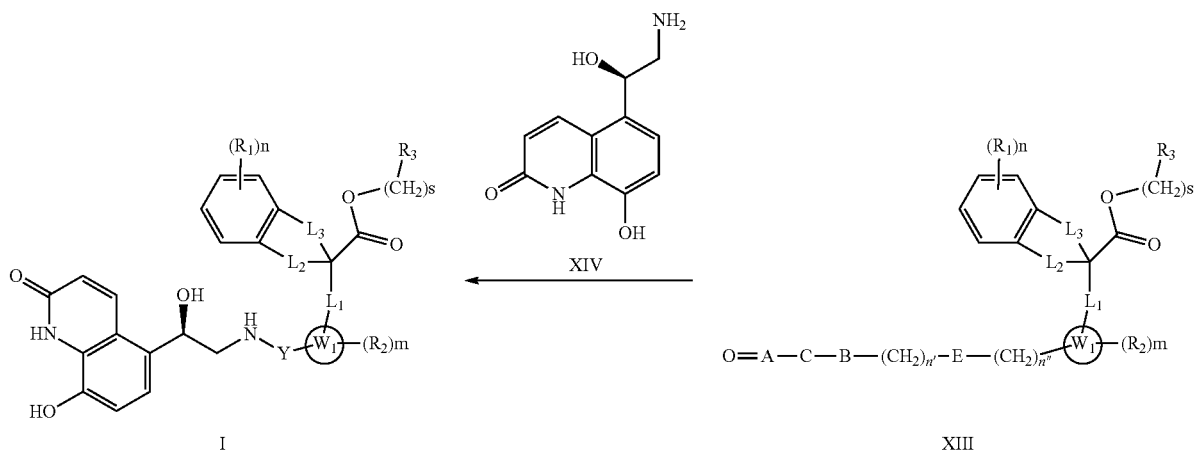
Scheme 1B
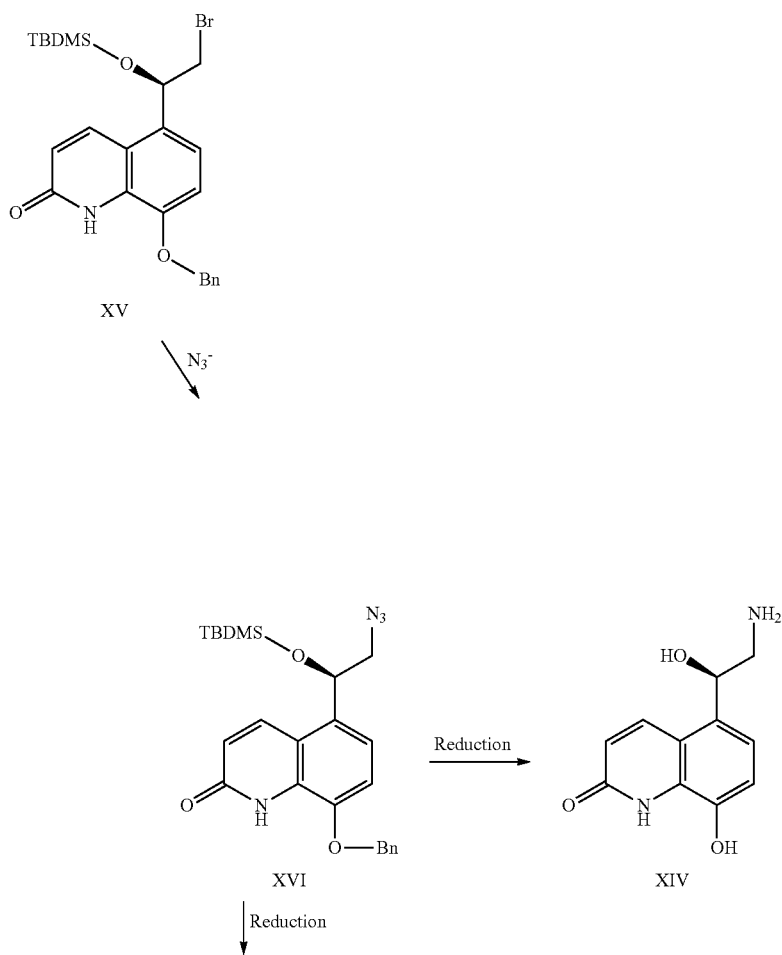

-continued

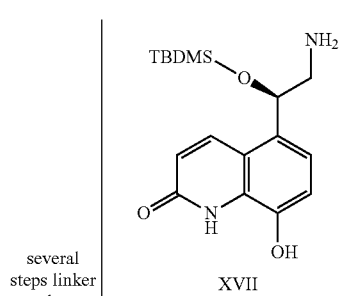

XVII several steps linker attachment

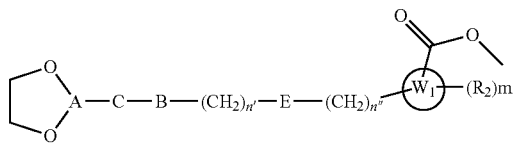

XI

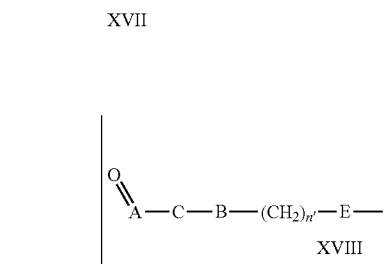

XVIII 2) hydrolysis

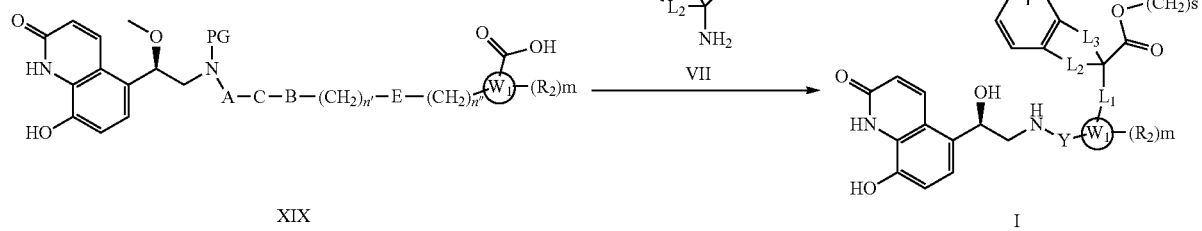

XIX

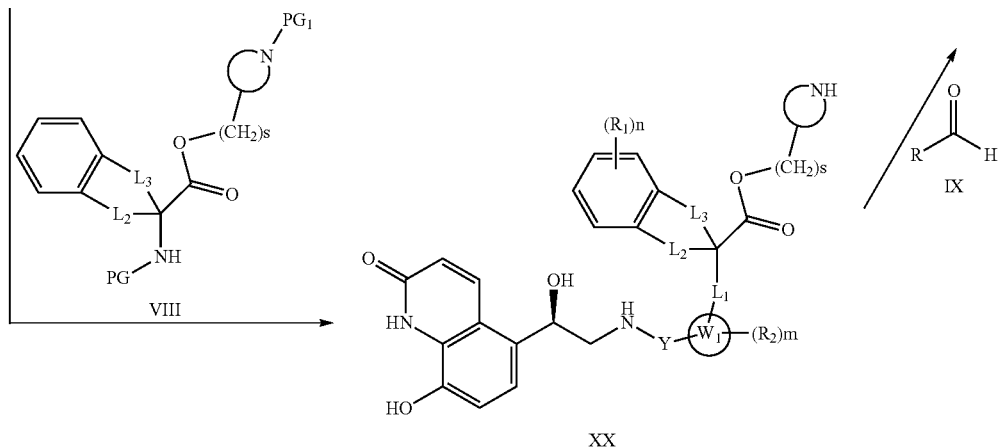

VIII

XX

General Procedure for the Preparation of Compounds of Formula I

Compounds of formula I are compounds in which Y is a divalent group that links to heads at the two sides of the molecule. There are many different strategies that can be considered for the preparation of compound of formula I, but a few can be more evident to a person skilled in the art: start from left hand side head, building up the linker Y and then attach the right hand side head, perform the opposite or complete the synthesis of an advanced intermediate that requires modification at one head to complete the preparation of compound of formula I.

The synthesis of compounds of formula I may require the protection of potential reactive functionalities in addition to those methods described hereinbelow. In such a case, examples of compatible protecting groups (PG) and their particular methods of protection and deprotection are described in "Protecting groups in organic Synthesis" by T. W. Green and P. Wutz (Wiley-Interscience publication, 1999), which is incorporated herein by reference in its entirety. Compounds of formula I can be prepared for example by reaction of a compound of formula XIII with a compound of formula XIV. This reductive amination reaction can be performed following several known different protocols. For example, it can be performed in solvent such as methanol, ethanol, tetrahydrofuran (THF) or dichloromethane (DCM) using a reducing agent such as NaBH$_4$, NaCNBH$_3$ or NaB(AcO)$_3$H. It could be useful to preform the imine before adding the reducing agent. The reaction proceeds smoothly at room temperature (RT) over 1 to 12 hours.

The compounds of formula X represents a compound wherein A is alkylene substituted with oxo, leading to an aldehyde or ketone protected as cyclic acetal. The cyclic acetal can be also replaced by other non cyclic acetals, protecting groups widely used for ketones and aldehydes. Where present, the cyclic acetal-protecting group (PG) can be easily removed under acidic aqueous condition, leading to the deprotected aldehyde or ketone.

In one embodiment of the present invention, compound X can be used for the preparation of a compound of formula XIII by reaction with a compound of formula VII, followed by hydrolysis of the acetal protecting group of the carbonyl moiety. The first step is a condensation that can be performed under the well-known condensation conditions for the preparation of amides. The reaction occurs smoothly in an aprotic polar solvent such as acetonitrile (ACN), THF or DMF at room or higher temperature in the presence of a condensing agent such as for example EDC, DCC, HATU. The reaction described above can be also performed under same reaction conditions described using compound of formula X deprotected at the carbonyl moiety of group A.

Alternatively, a compound of formula XIII can be prepared, using the same reaction conditions described above for the preparation of compound of formula I, by reacting a compound of formula VII with an aldehyde of formula XII. The preparation of a compound of formula X and XII can be faced in a wide variety of ways that depends on functional groups present. A versatile compound that can be used for the preparation of X is XI. The ester present in XI can be easily converted in X by mean of an aqueous hydrolysis performed under basic condition.

The compound of formula XI is a versatile intermediate because it can be converted into compound of formula XVIII that can be used for the preparation of compound of formula XIX as described below.

The compound of formula VII can be easily obtained from a compound of formula IV, under esters reaction condition, with a compound of formula VI, followed by deprotection. The reaction is performed using condensing agents like EDC, DCC, HATU cited above for the preparation of amide, or pre-activating the acid IV with carbonyldiimidazole (CDI). The reaction with CDI occurs at room temperature in an aprotic solvent such as THF or DMF leading to the imidazolide intermediate that react easily with an alcohol of formula VI. Alternatively, the acid can be converted into the corresponding acyl chloride (COCl$_2$ in DCM).

The compound of IV can be reacted under same identical conditions described above with a compound of formula V leading to a compound of formula VIII that, after removal of PG1, can be reacted with a compound of formula IX under the same reductive amination conditions described above for the reaction of XIII with a compound of general formula XIV, leading to compound VII wherein R$_3$ is J$_2$, J$_3$ or J$_4$.

The compounds of formula IV are commercially available or can be obtained by introduction of a suitable protecting group at the nitrogen moiety using condition known for the protection of amino acids.

In case a suitable precursor of IV is not available, it can be prepared using known reaction methodologies for the synthesis of amino acids such as for example the Strecker synthesis or Bucherer-Bergs Reaction. In the latter, a ketone of formula II is reacted with sodium or potassium cyanide in the presence of ammonium carbonate, or another source of carbon dioxide, in a polar solvent such as ethanol or THF often in mixture with water. The reaction requires few hours to complete at a temperature ranging from 50 to 100° C. and provides a compound of formula III that by treatment with aqueous NaOH, KOH or Ba(OH)$_2$ at high temperature (100-150° C.) followed by introduction of protecting group PG, leads to a compound of formula IV.

In another embodiment of the invention, the compound of formula I can be prepared reacting a compound of formula XIX with a compound of formula VII under the same reaction condition described above for the reaction of compound XIII with compound XIV.

Alternatively, the same conversion can be obtained in with a three-step preparation that requires the reaction of compound of foimula XIX with a compound of formula VIII (Deprotected at PG) followed by first deprotection of PG1 and then by reductive amination of the obtained compound XX with a compound of formula IX, under reaction condition described above.

The compound of formula XIX can be obtained by a two-step preparation, reacting a compound of formula XVII with a compound of formula XVIII under the reaction condition described above for the reaction of compound XIII with compound XIV, followed by hydrolysis of the ester leading to compound of formula XIX.

The compound of formula XVII can be obtained by simple reduction of the azide of formula XVI. The reaction can be accomplished by mean of a catalytic hydrogenation in the presence Palladium catalyst. The reaction occurs, in polar solvent such as methanol or ethanol, under hydrogen atmosphere or under hydrogen transfer conditions, using for example 1,4-cyclohexadiene or 1-methyl, 1,4-cyclohexadiene as source of hydrogen. The reaction proceeds at room temperature. In case it is performed under hydrogen transfer conditions higher temperature can be required.

If the reduction is performed under acidic conditions, for example using formic acid as source of hydrogen, it can cause complete deprotection and lead to a compound of formula XIV.

Alternatively, the conversion of compound XVI into compound XVII, can be accomplished under Staudinger reaction conditions, reacting the azide XVI for example first with triphenyl phosphine in THF, and then with water to hydrolyse the formed phosphazene.

The azide XVI can be easily prepared from XV, in most of the case featuring the OH protected as silyl ether, by the well-known nucleophilic substitution of alkyl bromide with alkaline azide. The reaction proceeds at a temperature ranging from 50 to 80° C. and in a polar solvent such as for example DMF of NMP and can be accelerated by the presence of alkaline iodide.

The preparation of single enantiomerically pure compounds of general formula XV is described in WO2005/092861, which is incorporated herein by reference in its entirety (cited by WO2007/107228, which is incorporated herein by reference in its entirety).

In another embodiment of the invention, the compound of formula XIX can be prepared starting from compound of formula XV or XVII and building up the linker step by step. For example, a compound of formula XVII can be reacted with 4-nitrobenzaldehyde under the reductive amination condition described above. After reduction of the nitro group, the obtained compound can be condensed, under amide formation conditions, with for example di-carboxylic acid mono-ester that lead to a compound of general formula XIX.

It is evident that compounds X, XI, XII, and XVIII represent a linker for the connection of two portions of the molecule. Some possible examples of synthesis have been provided in the present description, but these are just representative of possible approaches and they have not to be considered limiting the scope of the present invention. The synthesis of the linker and the sequence of synthetic steps depend on the functional groups present and on the availability of suitable reagents.

Compounds of general formula I wherein $R_3$ is J1, J2 or J4 and q=0 or q=2 contain at least three stereogenic centres. For example, as indicated in the structure below (wherein e.g. J=J1 and q=0) there are three stereogenic centers 1 and 2 on the alcoholic carbon and the quinuclidine carbon, and the symbol * is used to indicate a stereogenic center 3 whose absolute configuration has not been assigned.

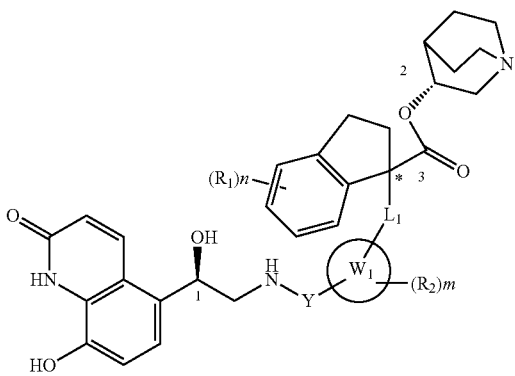

Each diastereoisomer can be obtained theoretically by chromatographic separation of the mixture obtained by reacting racemic mixtures of the required intermediates. It is clear that this approach it is not convenient and that it can be used only for the separation of mixtures containing few diastereoisomers.

In a more convenient approach, the synthesis of each single stereoisomer can be accomplished using, in the reactions described above, only enantiomerically pure intermediates assuming that any subsequent reaction steps do not cause epimerization.

The present invention also provides pharmaceutical compositions of compounds of formula I in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the present invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such as suitable carriers, are also known.

For topical administration the pharmaceutical composition can be in the form of creams, ointments, liniments, lotions, emulsions, suspensions, gels, solutions, pastes, powders, sprays, and drops suitable for administration to the skin, eye, ear, or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the present invention, e.g., lactose or any other additive suitable for improving the respirable fraction may be added to the powdered compounds of the invention.

Inhalation aerosols containing propellant gas such as hydrofluoroalkanes may contain the compounds of the present invention either in solution or in dispersed form. The propellant-driven formulations may also contain other ingredients such as co-solvents, stabilizers and optionally other excipients.

The propellant-free inhalable formulations comprising the compounds of the present invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the present invention may be administered as the sole active agent or in combination with other pharmaceutical active ingredients including those currently used in the treatment of respiratory disorders, e.g., corticosteroids, P38 MAP kinase inhibitors, IKK2, HNE inhibitors, PDE4 inhibitors, leukotriene modulators, NSAIDs and mucus regulators.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula I can be administered for example, at a dosage of 0.001 to 1000 mg/day, preferably 0.1 to 500 mg/day.

When the compounds of formula I are administered by inhalation route, they are preferably given at a dosage of 0.001 to 500 mg/day, preferably 0.1 to 200 mg/day.

The compounds of formula I may be administered for the prevention and/or treatment of broncho-obstructive or inflammatory diseases, such as asthma, chronic bronchitis, chronic obstructive pulmonary disease (COPD), bronchial hyperreactivity, cough, emphysema or rhinitis; urological disorders such as urinary incontinence, pollakiuria, cystospasm, chronic cystitis and overactive bladder (OAB); gastrointestinal disorders such as bowel syndrome, spastic colitis, diverticulitis, peptic ulceration, gastrointestinal motility or gastric acid secretion; dry mouth; mydriasis, tachycardia; ophthalmic interventions cardiovascular disorders such as vagally induced sinus bradycardia.

Other features of the invention will become apparent in the course of the following descriptions of exemplary embodiments which are given for illustration of the invention and are not intended to be limiting thereof.

EXAMPLES

The intermediate compounds for the synthesis of final compounds of general formula (I) were obtained through the preparations herebelow described.

Chemical Names of the compounds were generated with Structure To Name Enterprise 10.0 Cambridge Software.
Abbreviations
Bn=benzyl group;
DCC=N,N'-dicyclohexylcarbodiimide;
DIAD=diisopropyl azodicarboxylate;
DIPEA=diisopropylethylamine;
HOBt=hydroxybenzotriazole;
HATU=(dimethylamino)-N,N-dimethyl(3H-[1,2,3]triazolo[4,5-b]pyridin-3-yloxy)methaniminium hexafluorophosphate;
EDC=1-ethyl-3-(3-dimethylaminopropyl) carbodiimide hydrochloride;
DMAP=4-dimethylaminopyridine;
DMF=dimethylformamide;
EtOAc=ethyl acetate;
NMP=N-methyl-2-pyrrolidone;
RT=room temperature;
TBDMS=tert-butyldimethylsilyl group;
THF=tetrahydrofuran;
DCM=dichloromethane;
LiHMDS=lithium bis(trimethylsilyl)amide;
p-TSA-H$_2$O=p-toluenesulphonic acid hydrate;
TFA=trifluoroacetic acid;
LC-MS=liquid chromatography/mass spectrometry;
HPLC=high pressure liquid chromatography;
ESI=electrospray ionization;
APCI=atmospheric pressure chemical ionization;
ESCI=combined ESI-APCI Ionization Source;
ELS=evaporative light scattering.
General Experimental Details
NMR Characterization:

$^1$H-NMR spectra were performed on a Varian MR-400 spectrometer operating at 400 MHz (proton frequency), equipped with: a self-shielded z-gradient coil 5 mm 1H/nX broad band probehead for reverse detection, deuterium digital lock channel unit, quadrature digital detection unit with transmitter offset frequency shift. Chemical shift are reported as S values in ppm relative to trimethyl silane (TMS) as an internal standard. Coupling constants (J values) are given in hertz (Hz) and multiplicities are reported using the following abbreviation (s=singlet, d=doublet, t=triplet, q=quartet, m=multiplet, br=broad, nd=not determined).
LC/UV/MS Analytical Methods LC/MS retention times are estimated to be affected by an experimental error of ±0.5 min.
Method 1
    10 cm_Formic_ACE 3 C18 AR_HPLC_CH3CN
    HPLC setup;
    Solvents—Acetonitrile (Far UV grade) with 0.1% (V/V) formic acid; Water (High purity via PureLab Ultra unit) with 0.1% formic acid
    Column—Hichrom ACE 3 C18-AR mixed mode column 100×4.6 mm
    Flow rate—1 mL/min
    Gradient

| Time (min) | % A | % B |
|---|---|---|
| 0.00 | 98 | 2 |
| 3 | 98 | 2 |
| 12 | 0 | 100 |
| 15.4 | 0 | 100 |
| 15.5 | 98 | 2 |
| 17 | 98 | 2 |

Injection—0.2-10 µl
    Maximum pressure setting—400 bar.
    Instrument—Agilent 1100, Binary Pump, Agilent Sampler and Agilent DAD detector
    Diode array detection—(300 nm, Band Width 200 nm; Ref. 450 nm, Band Width 100 nm)
Method 2
    15 cm_Formic_Ascentic_HPLC_CH3CN
    HPLC setup;
    Solvents—Acetonitrile (Far UV grade) with 0.1% (V/V) formic acid; Water (High purity via PureLab Ultra unit) with 0.1% formic acid
    Column—Supelco, Ascentis® Express C18 or Hichrom Halo C18, 2.7 µm C18, 150×4.6 mm.
    Flow rate—1 mL/min
    Gradient:

| Time (min) | % A | % B |
|---|---|---|
| 0.00 | 96 | 4 |
| 3 | 96 | 4 |
| 9 | 0 | 100 |
| 13.6 | 0 | 100 |
| 13.7 | 96 | 4 |
| 15 | 96 | 4 |

Injection—0.2-10 µl
    Maximum pressure setting—400 bar.
    Instrument—Agilent 1100, Binary Pump, Agilent Sampler and Agilent DAD detector
    Diode array detection—(300 nm, Band Width 200 nm; Ref. 450 nm, Band Width 100 nm)
Method 3
    10 cm_ESCI_Formic_MeCN
    HPLC Setup Solvents—Acetonitrile (Far UV grade) with 0.1% (V/V) formic acid; Water (High purity via PureLab Option unit) with 0.1% formic acid Column:—Phenomenex Luna 5μ C18 (2), 100×4.6 mm. (Plus guard cartridge)

Flow Rate:—2 ml/min

Gradient:

| Time (min) | % A | % B |
|---|---|---|
| 0.00 | 95 | 5 |
| 3.5 | 5 | 95 |
| 5.5 | 5 | 95 |
| 5.6 | 95 | 5 |
| 6.5 | 95 | 5 |

Injections 2-7 μl (concentration ~0.2-1 mg/ml).

UV detection via HP or Waters DAD

Start Range (nm) 210 End Range (nm) 400 Range interval (nm) 4.0

Other wavelength traces are extracted from the DAD data.

Optional ELS detection using Polymer Labs ELS-1000.

MS detection: Micromass ZQ, single quadrupole LC-MS or Quattro Micro LC-MS-MS.

Flow splitter gives approximately 300 μl/min to mass spec

Scan range for MS Data (m/z)

Start (m/z) 100

End (m/z) 650 or 1500 when required

With +ve/−ve switching

Ionization is routinely ESCI an option which gives both ESI and APCI data from a single run.

Typical ESI voltages and temperatures are:

Source 120-150° C. 3.5 KV capillary 25V cone

Typical APCI voltages and temperatures are:

Source 140-160° C. 17 uA corona 25V cone

Method 4

10 cm_Formic_AQ

UPLC Setup

Solvents:—B Acetonitrile (Far UV grade) with 0.1% (V/V) formic acid; Water (High purity via PureLab Option unit) with 0.1% formic acid Column:—Acquity UPLC HSS C18 1.8 um 100×2.1 mm. (Plus guard cartridge)

Flow Rate:—0.5 ml/min

Gradient:

| Time (min) | % A | % B |
|---|---|---|
| 0.00 | 95 | 5 |
| 1.2 | 95 | 5 |
| 3.5 | 0 | 100 |
| 4.9 | 0 | 100 |
| 5 | 95 | 5 |
| 6 | 95 | 5 |

Injections 0.5-2 μl

UV detection via Waters DAD

Start Range (nm) 210 End Range (nm) 400 Resolution (nm) 1.2

MS detection: Waters SQD2, single quadrupole UPLC-MS

Scan range for MS Data (m/z)

Start (m/z) 100

End (m/z) 700 or 1500 when required

With +ve/−ve switching

Ionization is ESI.

ESI voltages and temperatures are:

Source 150° C. 3.5 KV capillary 25V cone

Preparative Reverse-Phase HPLC Conditions

Post-synthesis all compounds were purified using reverse phase HPLC.

The column used for the preparative purification of the compounds was a Waters Sunfire OBD, Phenomenex Luna Phenyl Hexyl or Waters Xbridge Phenyl at 10 um 19×150.

All compounds were screen analytically prior to the purification step. Each sample was run under both acidic and basic conditions. As it is common practice, the best method and conditions to be used for the purification was chosen depending on where the desired product elutes and the separation achieved.

The modifier used in the purification determined the final salt form obtained (e.g., formate or trifluoroacetate).

Where the preparation of starting materials is not described, these are commercially available, known in the literature, or readily obtainable using standard procedures.

Many of the compounds described in the following Examples have been prepared from stereochemically pure starting materials, for example 95% ee.

The stereochemistry of the compounds in the Examples, where indicated, has been assigned on the assumption that absolute configuration at resolved stereogenic centers of starting materials is maintained throughout any subsequent reaction conditions.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

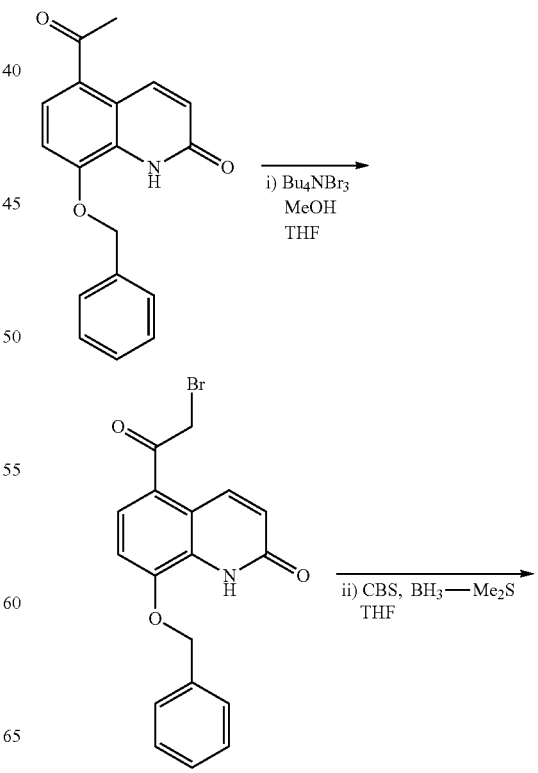

-continued

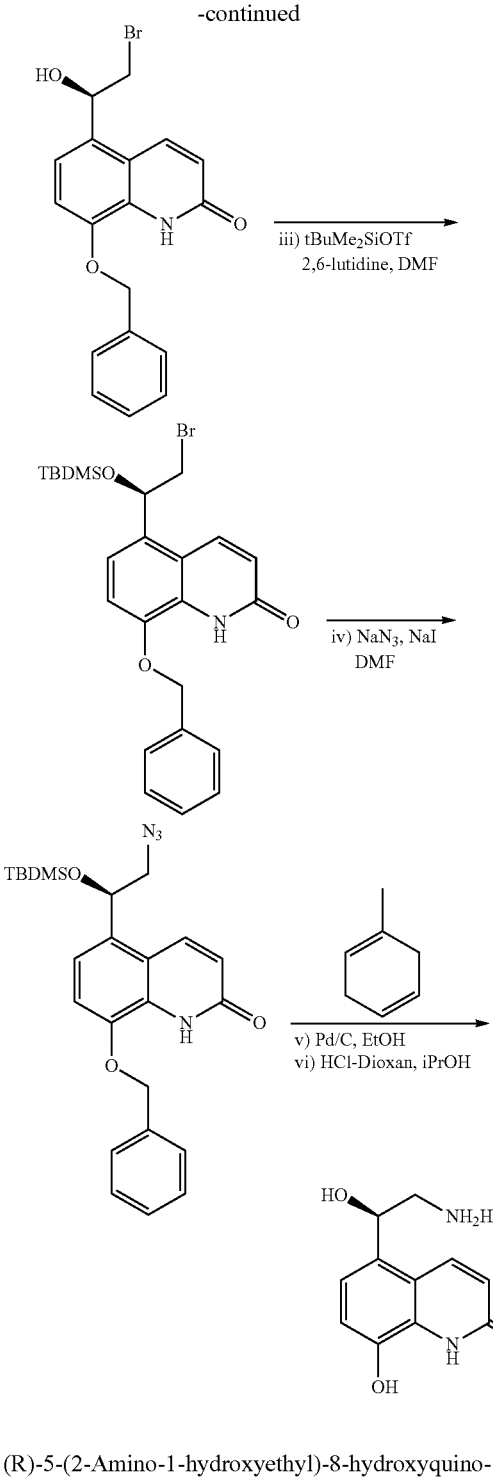

Step 1. 8-(Benzyloxy)-5-(2-bromoacetyl)quinolin-2(1H)-one

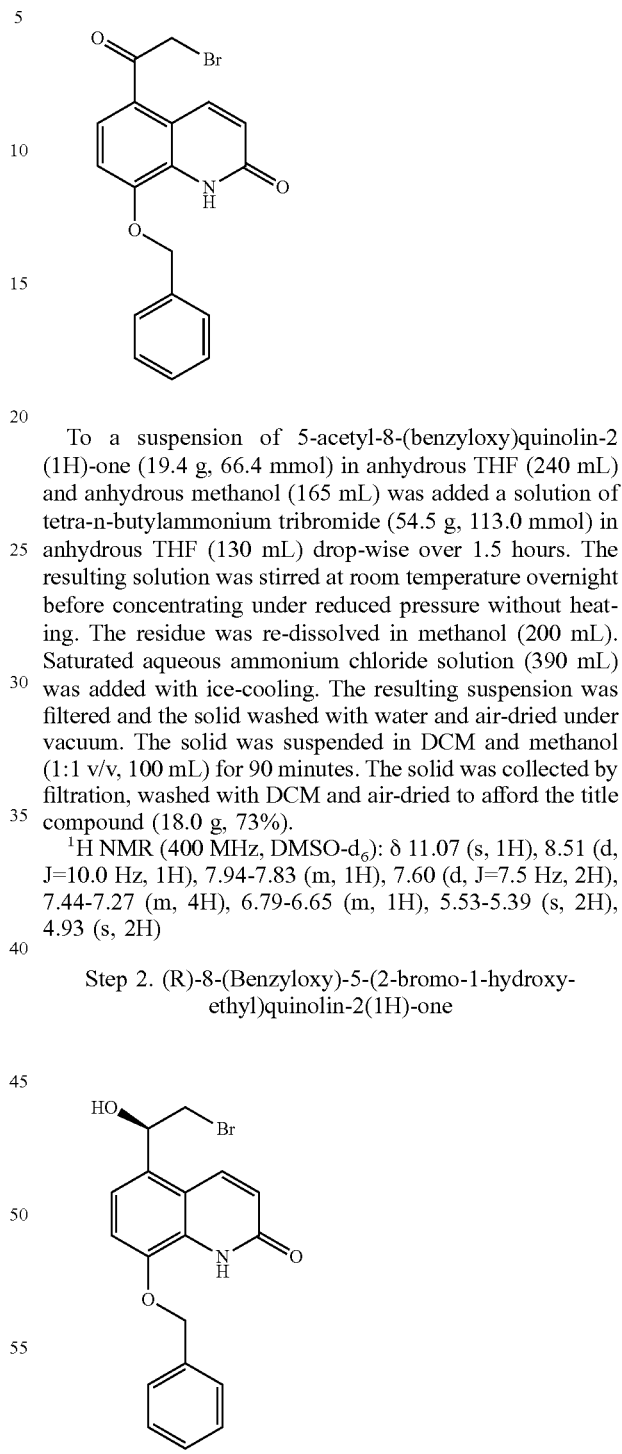

To a suspension of 5-acetyl-8-(benzyloxy)quinolin-2(1H)-one (19.4 g, 66.4 mmol) in anhydrous THF (240 mL) and anhydrous methanol (165 mL) was added a solution of tetra-n-butylammonium tribromide (54.5 g, 113.0 mmol) in anhydrous THF (130 mL) drop-wise over 1.5 hours. The resulting solution was stirred at room temperature overnight before concentrating under reduced pressure without heating. The residue was re-dissolved in methanol (200 mL). Saturated aqueous ammonium chloride solution (390 mL) was added with ice-cooling. The resulting suspension was filtered and the solid washed with water and air-dried under vacuum. The solid was suspended in DCM and methanol (1:1 v/v, 100 mL) for 90 minutes. The solid was collected by filtration, washed with DCM and air-dried to afford the title compound (18.0 g, 73%).

$^1$H NMR (400 MHz, DMSO-$d_6$): δ 11.07 (s, 1H), 8.51 (d, J=10.0 Hz, 1H), 7.94-7.83 (m, 1H), 7.60 (d, J=7.5 Hz, 2H), 7.44-7.27 (m, 4H), 6.79-6.65 (m, 1H), 5.53-5.39 (s, 2H), 4.93 (s, 2H)

Step 2. (R)-8-(Benzyloxy)-5-(2-bromo-1-hydroxyethyl)quinolin-2(1H)-one 8-(Benzyloxy)-5-(2-bromoacetyl)quinolin-2(1H)-one (26.0 g, 69.9 mmol) and (R)-3,3-diphenyl-1-methyltetrahydro-3H-pyrrolo[1,2-c][1,3,2]oxazaborole (21.3 g, 76.8 mmol) were azeotroped with toluene (×3) then suspended in anhydrous THF (400 mL) under an atmosphere of nitrogen. The suspension was cooled to −20° C. (external temperature) and borane dimethyl sulfide complex solution (45.4 mL, 90.8 mmol, 2.0 M solution in THF) was added by syringe pump over 3 hours. After complete addition the reaction mixture was stirred for one hour before quenching with methanol (25 mL). The reaction was warmed to room temperature over 20 minutes. The mixture was concentrated under reduced pressure and the residue was suspended in aqueous hydrochloric acid (500 mL, 1 M solution) and stirred at room temperature for 18 hours. After this time the solid was collected by filtration and washed with water (3×100 mL). The solid was partially dissolved in ethyl acetate and heated at reflux for 2 hours. The remaining solid was removed by hot filtration and the filtrate was evaporated to afford the title compound. The solid collected from the hot ethyl acetate was again partially dissolved in ethyl acetate and heated at reflux for 2 hours then filtered to give filtrate containing pure product. This process was repeated four more times. The combined solid was recrystallised from ethyl acetate and petroleum ether to afford the title compound (20.0 g, 76%).

$^1$H NMR (400 MHz, DMSO-$d_6$): δ 10.68 (s, 1H), 8.19 (d, J=9.9 Hz, 1H), 7.58 (d, J=7.5 Hz, 2H), 7.41-7.36 (m, 2H), 7.34-7.29 (m, 1H), 7.23-7.19 (m, 2H), 6.57 (d, J=9.8 Hz, 1H), 5.94 (d, J=4.7 Hz, 1H), 5.31 (s, 2H); 5.25-5.19 (m, 1H), 3.71-3.58 (m, 2H).

Step 3. (R)-8-(Benzyloxy)-5-(2-bromo-1-((tert-butyldimethylsilyl)oxy)ethyl)quinolin-2(1H)-one

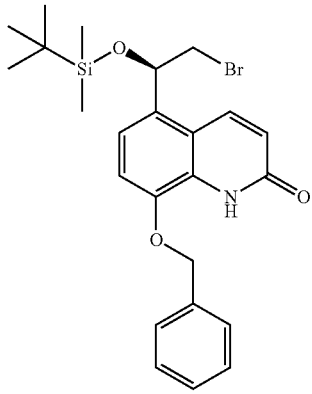 [SMILES: CC(C)(C)[Si](C)(C)O[C@@H](CBr)c1ccc(OCc2ccccc2)c2[nH]c(=O)ccc12]

2,6-Lutidine (6.9 mL, 59.5 mmol) was added to a solution of (R)-8-(benzyloxy)-5-(2-bromo-1-hydroxyethyl)quinolin-2(1H)-one (10.1 g, 27.0 mmol) in DCM (100 mL) at 0° C. The reaction mixture was stirred for 5 minutes then tert-butyldimethylsilyl trifluoromethanesulfonate (13.0 mL, 56.8 mmol) was added dropwise over 15 minutes. The mixture was stirred at 0° C. for 30 minutes, followed by room temperature overnight. After this time the reaction was quenched with saturated aqueous sodium bicarbonate solution and extracted with DCM (×3). The combined organic extracts were dried (magnesium sulfate), filtered and concentrated under reduced pressure. Iso-hexane (500 mL) was added to the crude material and the resulting solid collected by filtration. The solid was recrystallised from ethyl acetate and petroleum ether (40:60) to afford the title compound (11.3 g, 85%).

$^1$H NMR (400 MHz, CDCl$_3$): δ 9.19 (s, 1H), 8.23 (dd, J=9.9, 4.4 Hz, 1H), 7.43 (d, J=4.6 Hz, 5H), 7.17 (dd, J=8.3, 4.5 Hz, 1H), 7.03 (dd, J=8.2, 4.4 Hz, 1H), 6.71 (dd, J=9.9, 3.7 Hz, 1H), 5.18 (d, J=4.5 Hz, 3H), 3.63-3.56 (m, 1H), 3.49 (dd, J=10.4, 4.8 Hz, 1H), 0.88 (t, J=4.4 Hz, 9H), 0.14 (d, J=4.4 Hz, 3H), −0.11 (d, J=4.4 Hz, 3H).

Step 4. (R)-5-(2-Azido-1-((tert-butyldimethylsilyl)oxy)ethyl)-8-(benzyloxy)quinolin-2(1H)-one

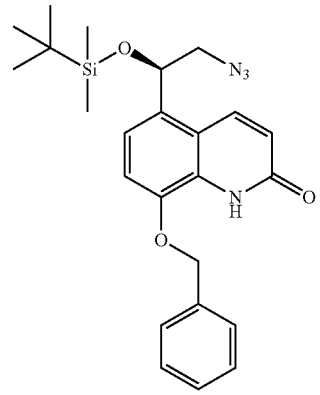 [SMILES: CC(C)(C)[Si](C)(C)O[C@@H](CN=[N+]=[N-])c1ccc(OCc2ccccc2)c2[nH]c(=O)ccc12]

(R)-8-(Benzyloxy)-5-(2-bromo-1-((tert-butyldimethylsilyl)oxy)ethyl)quinolin-2(1H)-one (10.0 g, 20.5 mmol) was dissolved in DMF (180 mL) and water (20 mL). Sodium iodide (3.39 g, 22.6 mmol) and sodium azide (1.47 g, 22.6 mmol) were added sequentially. The reaction mixture was stirred at RT until all the solid was in solution. The solution was heated at 80° C. for 40 hours then cooled to RT and diluted with ethyl acetate (300 mL). The mixture was washed with water, brine (×2) and the organic extract was dried (magnesium sulfate), filtered and concentrated under reduced pressure. The crude residue was triturated with iso-hexane to afford the desired compound (8.16 g, 88%). Used without further purification in the next step.

$^1$H NMR (400 MHz, CDCl$_3$): δ 9.19 (s, 1H), 8.18 (d, J=9.9 Hz, 1H), 7.45-7.36 (m, 5H), 7.20 (d, J=8.3 Hz, 1H), 7.04 (d, J=8.3 Hz, 1H), 6.70 (dd, J=9.9, 2.2 Hz, 1H), 5.19-5.13 (m, 3H), 3.48 (dd, J=12.7, 8.1 Hz, 1H), 3.26 (dd, J=12.7, 3.8 Hz, 1H), 0.89 (s, 9H), 0.14 (s, 3H), −0.11 (s, 3H).

Step 5. (R)-5-(2-Amino-1-hydroxyethyl)-8-hydroxyquinolin-2(1H)-one hydrochloride

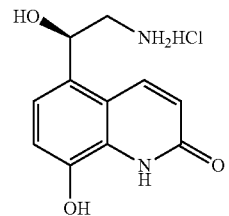

To a solution of (R)-5-(2-azido-1-((tert-butyldimethylsilyl)oxy)ethyl)-8-(benzyloxy)quinolin-2(1H)-one (4.50 g, 10.0 mmol) in ethanol (50 mL) was added 10% palladium on charcoal (4.50 g) followed by 1-methyl-1,4-cyclohexadiene (11.0 mL, 97.9 mmol). The reaction was warmed to 60° C. and then stirred at 60° C. for 2 hours. The reaction mixture was allowed to cool and filtered through a pad of celite. The filtercake was washed with further ethanol and the filtrate was evaporated at reduced pressure. The residue was evaporated from iso-propanol (×2) and dissolved in iso-propanol (30 mL). HCl-dioxane (4M, 50 mL, 200 mmol) was added and the reaction mixture stirred at room temperature for 18 hours. The resultant suspension was filtered, the filtercake washed with ether and the solid dried under vacuum in the presence of $P_2O_5$ to afford the title compound (1.65 g, 62%).

$^1$H NMR (400 MHz, MeOD): δ 7.71 (d, J=9.8 Hz, 1H), 6.57 (d, J=8.2 Hz, 1H), 6.31 (d, J=8.2 Hz, 1H), 6.02 (dd, J=9.8, 6.5 Hz, 1H), 4.58 (dd, J=9.6, 3.5 Hz, 1H), 2.47-2.31 (m, 2H).

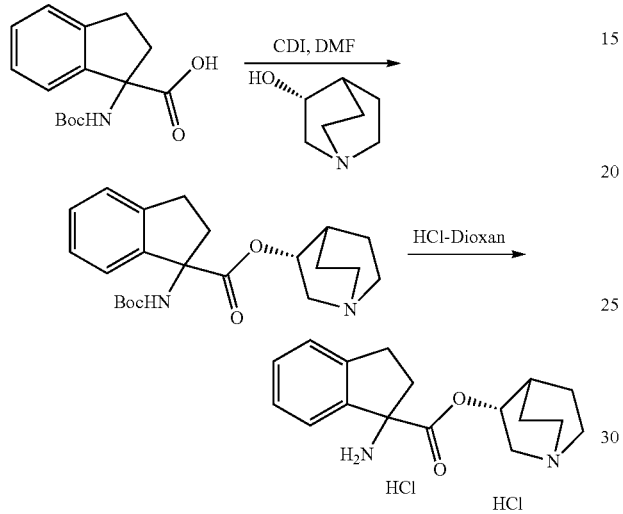

Step 1. (R)-Quinuclidin-3-yl 1-((tert-butoxycarbonyDamino)-2,3-dihydro-1H-indene-1-carboxylate

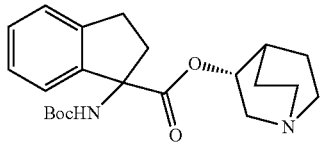 [SMILES: CC(C)(C)OC(=O)NC1(C(=O)O[C@H]2CN3CCC2CC3)CCc2ccccc21]

To a solution of 1-((tert-butoxycarbonyl)amino)-2,3-dihydro-1H-indene-1-carboxylic acid (2.8 g, 10.09 mmol) in DMF (28 mL) was added carbonyldiimidazole (1.63 g, 13.12 mmol) and the mixture was stirred at 50° C. for 90 minutes. (R)-Quinuclidinol (1.67 g, 13.12 mmol) was added and the mixture stirred at this temperature for a further 48 hours. The reaction mixture was diluted with ethyl acetate and washed with water, aqueous 2M sodium carbonate and brine. The organic phase was dried over magnesium sulfate, filtered and the filtrate evaporated at reduced pressure to afford the title compound (3.62 g, 93%).

$^1$H NMR (400 MHz, CDCl$_3$); δ 7.34-7.29 (m, 2H), 7.26-7.18 (m, 2H), 5.48-5.41 (m, 1H), 4.81-4.74 (m, 1H), 3.19-3.05 (m, 6H), 2.82-2.63 (m, 6H), 2.53 (d, J=14.7 Hz, 1H), 2.44-2.38 (m, 2H), 1.98 (d, J=2.4 Hz, 1H), 1.90 (s, 1H), 1.70-1.56 (m, 2H), 1.55-1.43 (m, 5H).

Step 2. (R)-Quinuclidin-3-yl 1-amino-2,3-dihydro-1H-indene-1-carboxylate dihydrochloride

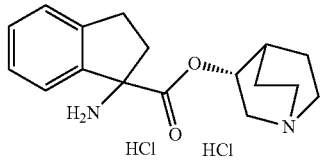 [SMILES: NC1(C(=O)O[C@H]2CN3CCC2CC3)CCc2ccccc21 ; Cl ; Cl]

A solution of HCl-dioxane (4M, 11.7 mL) was added to (R)-quinuclidin-3-yl 1-((tert-butoxycarbonyl)amino)-2,3-dihydro-1H-indene-1-carboxylate (3.62 g, 9.36 mmol) and the mixture stirred at room temperature for 48 hours. The solvent was evaporated at reduced pressure to afford the title compound (3.83 g, 100%).

$^1$H NMR (400 MHz, DMSO-d$_6$); δ 10.82-10.77 (m, 1H), 9.43 (d, J=14.7 Hz, 3H), 7.70-7.66 (m, 2H), 7.42-7.31 (m, 2H), 5.14-5.09 (m, 1H), 3.44-3.06 (m, 9H), 2.89-2.83 (m, 1H), 2.44-2.35 (m, 1H), 2.17-2.12 (m, 1H), 1.89 (ddd, J=4.6, 9.2, 18.4 Hz, 1H), 1.82-1.70 (m, 2H).

Example 1. (R)-Quinuclidin-3-yl 1-((3-((4-(((R)-2-hydroxy-2-(8-hydroxy-2-oxo-1,2-dihydroquinolin-5-yl)ethyl)amino)butyl)carbamoyl)benzyl)amino)-2,3-dihydro-1H-indene-1-carboxylate (Compound 1)

Step 1. N-(4,4-Diethoxybutyl)-3-formylbenzamide

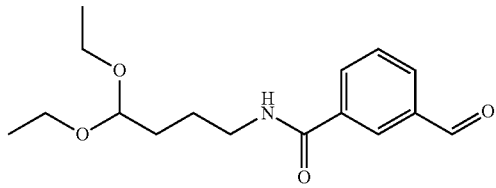 [SMILES: CCOC(CCCNC(=O)c1cccc(C=O)c1)OCC]

To a stirred solution of 3-formylbenzoic acid (0.50 g, 3.3 mmol) in DMF (7 mL) was added DIPEA (0.61 mL, 3.5 mmol) and HATU (1.5 g, 4.0 mmol) and the mixture stirred at room temperature for 15 minutes. 4,4-Diethoxybutan-1-amine (0.43 g, 2.68 mmol) was added and the stirring continued for a further five hours. The reaction mixture was diluted and washed sequentially with aqueous 1M sodium hydroxide, aqueous 2M sodium hydroxide and brine. The organic phase was dried over magnesium sulfate, filtered and the filtrate evaporated at reduced pressure to afford the title compound (0.72 g, 93%).

$^1$H NMR (400 MHz, DMSO-d$_6$); δ 10.08 (s, 1H), 8.71 (dd, J=5.5, 5.5 Hz, 1H), 8.38 (s, 1H), 8.16 (d, J=7.8 Hz, 1H), 8.06 (d, J=7.7 Hz, 1H), 7.71 (dd, J=7.7, 7.7 Hz, 1H), 4.53-4.47 (m, 1H), 3.57 (ddd, J=7.0, 9.5, 14.1 Hz, 2H), 3.43 (ddd, J=7.1, 9.5, 14.1 Hz, 2H), 3.31-3.27 (m, 2H), 1.58-1.54 (m, 4H), 1.11 (dd, J=7.0, 7.0 Hz, 6H).

Step 2. (R)-Quinuclidin-3-yl 1-((3-((4,4-diethoxybutyl)carbamoyl)benzyl)amino)-2,3-dihydro-1H-indene-1-carboxylate

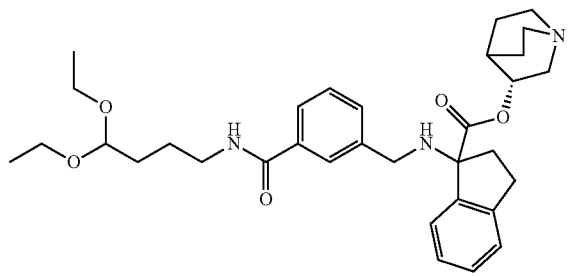 [SMILES: CCOC(CCCNC(=O)c1cccc(CNC2(C(=O)O[C@H]3CN4CCC3CC4)CCc3ccccc32)c1)OCC]

The pH of a stirred solution of (R)-quinuclidin-3-yl 1-amino-2,3-dihydro-1H-indene-1-carboxylate dihydrochloride (0.29 g, 1.02 mmol) in ethanol (4 mL) was adjusted to pH 7 with triethylamine and stirred at room temperature for 15 minutes. The pH of the mixture was adjusted to pH 6 with acetic acid and then a solution of N-(4,4-diethoxybutyl)-3-formylbenzamide (0.200 mg, 0.68 mL) in ethanol (1 mL) was added. The reaction mixture was stirred at this temperature for one hour and sodium cyanoborohydride (0.125 g, 2 mmol) was added. The reaction mixture stirred for a further one hour. The pH of the reaction mixture was adjusted to pH6 with triethylamine and the solvent evaporated at reduced pressure. The residue was diluted with a mixture of ethyl acetate/chloroform and washed with brine and the organic phase passed through a hydrophobic separation cartridge. The solvent was evaporated at reduced pressure. The residue was purified by flash column chromatography (eluent—90:10 ethyl acetate/methanol to 90:10 ethyl acetate/7N ammonia in methanol) to afford the title compound (0.158 g, 32%).

$^1$H NMR (400 MHz, DMSO-$d_6$); δ 8.41 (dd, J=5.4, 5.4 Hz, 1H), 7.81-7.78 (m, 1H), 7.68 (d, J=7.5 Hz, 1H), 7.51-7.45 (m, 2H), 7.37 (dd, J=7.6, 7.6 Hz, 1H), 7.30-7.22 (m, 3H), 4.83-4.78 (m, 1H), 4.48 (s, 1H), 3.70-3.65 (m, 2H), 3.55 (ddd, J=7.1, 9.5, 14.1 Hz, 2H), 3.42 (ddd, J=7.1, 9.5, 14.1 Hz, 2H), 3.29-3.21 (m, 4H), 3.17 (d, J=3.8 Hz, 1H), 3.04-2.96 (m, 3H), 2.89-2.79 (m, 4H), 2.72-2.61 (m, 2H), 2.24-2.15 (m, 1H), 2.00-1.91 (m, 1H), 1.74-1.58 (m, 3H), 1.41 (s, 1H), 1.31-1.20 (m, 1H), 1.17-1.08 (m, 6H).

Step 3. (R)-Quinuclidin-3-yl 1-((3-((4-(((R)-2-hydroxy-2-(8-hydroxy-2-oxo-1,2-dihydroquinolin-5-yl)ethyl)amino)butyl)carbamoyl)benzyl)amino)-2,3-dihydro-1H-indene-1-carboxylate (Compound 1)

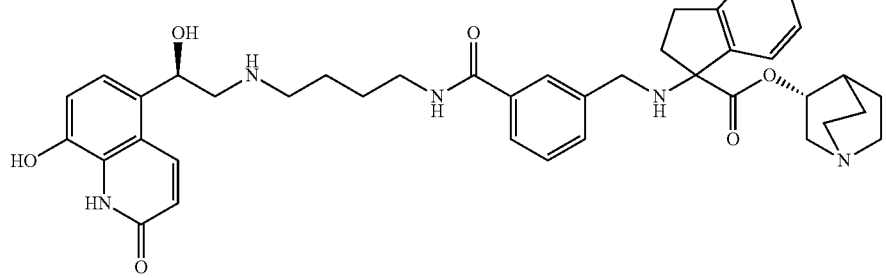

To a stirred solution of (R)-quinuclidin-3-yl 1-((3-(4,4-diethoxybutyl)-carbamoyl)benzyl)amino)-2,3-dihydro-1H-indene-1-carboxylate (0.158 g, 0.28 mmol) in THF (3.0 mL) was added aqueous 1M hydrochloric acid (3.0 mL) and the reaction mixture stirred at room temperature for 30 minutes. The reaction mixture was quenched with saturated aqueous sodium carbonate and the mixture extracted with ethyl acetate. The organic phase was dried over magnesium sulfate, filtered and the filtrate evaporated at reduced pressure. The residue was dissolved in ethanol (2 mL) and added to a pre-stirred (10 minutes) mixture of (R)-5-(2-amino-1-hydroxyethyl)-8-hydroxyquinolin-2(1H)-one hydrochloride (0.082 g, 0.31 mmol) and triethylamine (0.08 mL, 0.5 mmol) in ethanol (2 mL). The reaction mixture was stirred at room temperature for one hour. Sodium triacetoxyborohydride (0.110 g, 0.5 mmol) and acetic acid (0.07 mL, 1.0 mmol) were added and the reaction mixture stirred at room temperature for 18 hours. The reaction mixture was concentrated at reduced pressure and the residue partitioned between water and iso-butanol. The aqueous phase was extracted with additional iso-butanol and the combined organic extracts evaporated at reduced pressure. The residue was purified by reverse phase preparative HPLC to afford the title compound.

$^1$H NMR (400 MHz, MeOD); δ 8.37 (d, J=9.9 Hz, 1H), 8.02-8.00 (m, 1H), 7.90 (d, J=9.5 Hz, 1H), 7.73-7.52 (m, 5H), 7.46-7.38 (m, 1H), 7.31 (d, J=8.3 Hz, 1H), 7.05 (d, J=8.2 Hz, 1H), 6.66 (d, J=9.8 Hz, 1H), 5.44-5.39 (m, 1H), 5.39-5.28 (m, 1H), 4.39 (dd, J=8.8, 12.5 Hz, 1H), 4.29 (dd, J=5.5, 12.5 Hz, 1H), 3.83-3.72 (m, 1H), 3.50-3.35 (m, 3H), 3.32-3.21 (m, 6H), 3.18-2.99 (m, 4H), 2.88-2.72 (m, 2H), 2.49-2.45 (m, 0.5H), 2.25-2.20 (m, 0.5H), 2.10-1.72 (m, 6H), 1.71-1.62 (m, 1H), 1.33-1.24 (m, 1H).

Example 2. (R)-Quinuclidin-3-yl 1-(3-((5-(((R)-2-hydroxy-2-(8-hydroxy-2-oxo-1,2-dihydroquinolin-5-yl)ethyl)amino)pentyl)oxy)benzamido)-2,3-dihydro-1H-indene-1-carboxylate carboxylate (Compound 2)

Step 1. Methyl 3-(4-(1,3-dioxolan-2-yl)butoxy)benzoate

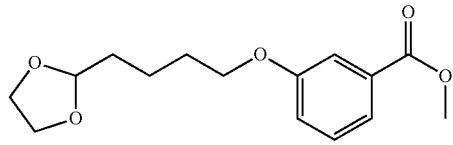 [SMILES: COC(=O)c1cccc(OCCCCC2OCCO2)c1]

To a stirred solution of methyl 3-hydroxybenzoate (0.350 g, 2.3 mmol) in DMF (6 mL) was added potassium carbonate (1.00 g, 7.0 mmol) followed by 2-(4-chlorobutyl)-1,3-dioxalane (0.515 g, 3.1 mmol). The reaction mixture was heated at 80° C. for 18 hours. The reaction mixture was diluted with ethyl acetate and washed sequentially with water and brine (×2). The organic phase was dried over anhydrous magnesium sulfate, the suspension was filtered and the filtrate concentrated at reduced pressure. The residue triturated with i-hexane to afford the title compound (0.7 g, 100%).

$^1$H NMR (400 MHz, DMSO-d$_6$); δ 7.53 (d, J=7.8 Hz, 1H), 7.45-7.41 (m, 2H), 7.22 (dd, J=2.4, 7.9 Hz, 1H), 4.81-4.77 (m, 1H), 4.02 (dd, J=6.4, 6.4 Hz, 2H), 3.85-3.75 (m, 7H), 1.80-1.46 (m, 6H).

Step 2. 3-(4-(1,3-Dioxolan-2-yl)butoxy)benzoic acid

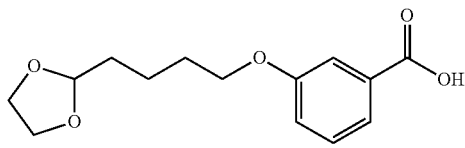 [SMILES: O=C(O)c1cccc(OCCCCC2OCCO2)c1]

To a stirred solution of methyl 3-(4-(1,3-dioxolan-2-yl)butoxy)benzoate (0.70 g, 2.5 mmol) in THF/methanol (12 mL/12 mL) was added aqueous 2M sodium hydroxide (12 mL). The reaction mixture was stirred at room temperature for 2.5 hours. The reaction mixture was evaporated at reduced pressure to half-volume. The mixture was diluted with water and washed with ether. The aqueous phase was treated with aqueous 1M hydrochloric acid to give pH 4. The mixture was extracted with ethyl acetate (×3) and the combined ethyl acetate extracts were dried over magnesium sulfate. The suspension was filtered and the filtrate concentrated at reduced pressure to afford the title compound (0.50 g, 75%).

$^1$H NMR (400 MHz, DMSO-d$_6$); δ 7.51 (d, J=7.8 Hz, 1H), 7.43-7.37 (m, 2H), 7.17 (dd, J=2.2, 8.1 Hz, 1H), 4.79 (dd, J=4.7, 4.7 Hz, 1H), 4.05-3.99 (m, 2H), 3.90-3.74 (m, 4H), 1.80-1.71 (m, 2H), 1.66-1.60 (m, 2H), 1.54-1.47 (m, 2H).

Step 3. (R)-Quinuclidin-3-yl 1-(3-(4-(1,3-dioxolan-2-yl)butoxy)benzamido)-2,3-dihydro-1H-indene-1-carboxylate

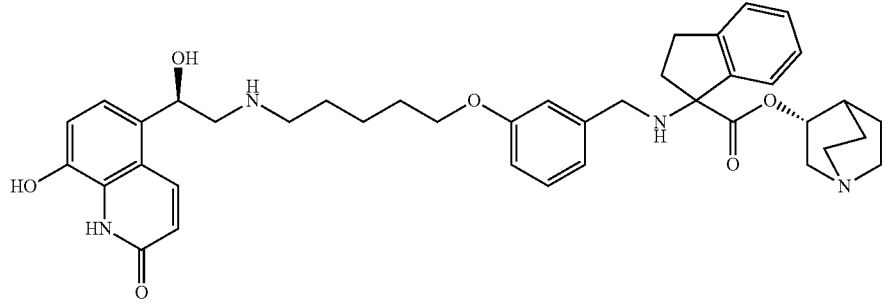 [SMILES: O=C(O[C@H]1CN2CCC1CC2)C1(NCc2cccc(OCCCCCNC[C@H](O)c3ccc(O)c4[nH]c(=O)ccc34)c2)CCc2ccccc21]

To a stirred solution of 3-(4-(1,3-dioxolan-2-yl)butoxy)benzoic acid (0.4 g, 1.5 mmol) in DMF (6 mL) was added DIPEA (0.65 mL, 3.75 mmol) and HATU (0.855 g, 2.3 mmol). This reaction mixture was stirred at room temperature for 45 minutes. (R)-Quinuclidin-3-yl 1-amino-2,3-dihydro-1H-indene-1-carboxylate dihydrochloride (0.43 g, 1.5 mmol) was added and the reaction mixture stirred at room temperature for 18 hours followed by stirring at 50° C. for 7 hours. The reaction mixture was diluted with ethyl acetate and washed with saturated aqueous sodium carbonate (×3) and brine. The organic phase was dried over anhydrous magnesium sulfate, the suspension was filtered and the filtrate concentrated at reduced pressure. The residue was purified by flash column chromatography (eluent—90:10 ethyl acetate/methanol to 90:10 ethyl acetate/7N ammonia in methanol) to afford the title compound (0.195 g, 24%).

$^1$H NMR (400 MHz, DMSO-d$_6$); δ 9.12-9.07 (m, 1H), 7.64-7.24 (m, 7H), 7.08 (dd, J=2.4, 8.1 Hz, 1H), 4.79 (dd, J=4.7, 4.7 Hz, 1H), 4.66-4.58 (m, 1H), 4.07-3.97 (m, 2H), 3.89-3.73 (m, 4H), 3.06-2.97 (m, 4H), 2.68-2.53 (m, 3H), 2.34-2.20 (m, 1H), 1.79-1.71 (m, 4H), 1.66-1.43 (m, 7H), 1.29-1.18 (m, 2H).

Step 4. (R)-Quinuclidin-3-yl 1-(3-((5-(((R)-2-hydroxy-2-(8-hydroxy-2-oxo-1,2-dihydroquinolin-5-yl)ethyl)amino)pentyl)oxy)benzamido)-2,3-dihydro-1H-indene-1-carboxylate (Compound 2)

The title compound was prepared as in Example 1 Step 3 with (R)-quinuclidin-3-yl 1-(3-(4-(1,3-dioxolan-2-yl)butoxy)benzamido)-2,3-dihydro-1H-indene-1-carboxylate replacing (R)-quinuclidin-3-yl 1-((3-((4,4-diethoxybutyl)carbamoyl)benzyl)amino)-2,3-dihydro-1H-indene-1-carboxylate.

$^1$H NMR (400 MHz, MeOD); δ 8.52 (s, 2H), 8.39 (d, J=9.9 Hz, 1H), 7.61 (t, J=8.9 Hz, 1H), 7.46-7.28 (m, 7H), 7.14-7.10 (m, 1H), 7.05 (d, J=8.2 Hz, 11-1), 6.70 (d, J=9.8 Hz, 1H), 5.41 (t, J=6.7 Hz, 1H), 5.04-5.01 (m, 0.5H), 4.99-4.95 (m, 0.511), 4.09 (t, J=5.6 Hz, 2H), 3.60-3.50 (m, 1H), 3.31-3.22 (m, 3H), 3.19-3.05 (m, 8H), 2.99-2.90 (m, 1H), 2.41-2.22 (m, 211), 2.00-1.79 (m, 7H), 1.73-1.59 (m, 3H).

Example 3. (R)-Quinuclidin-3-yl 1-((3-((5-(((R)-2-hydroxy-2-(8-hydroxy-2-oxo-1,2-dihydroquinolin-5-yl)ethyl)amino)pentyl)oxy)benzyl)amino)-2,3-dihydro-1H-indene-1-carboxylate (Compound 3)

Step 1. 3-(4-(1,3-Dioxolan-2-yl)butoxy)benzaldehyde

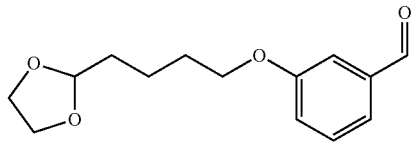 [SMILES: O=Cc1cccc(OCCCCC2OCCO2)c1]

The target compound was prepared as described in Example 2 Step 1 with 3-hydroxybenzaldehyde replacing methyl 3-hydroxybenzoate.

$^1$H NMR (400 MHz, CDCl$_3$); δ 9.96 (s, 1H), 7.45-7.42 (m, 2H), 7.40-7.37 (m, 1H), 7.19-7.15 (m, 1H), 4.89-4.87 (m, 1H), 4.14-4.01 (m, 2H), 3.99-3.95 (m, 2H), 3.82-3.81 (m, 2H), 1.90-1.83 (m, 2H), 1.77-1.70 (m, 2H), 1.66-1.58 (m, 2H).

Step 2. (R)-Quinuclidin-3-yl 1-((3-((5-(((R)-2-hydroxy-2-(8-hydroxy-2-oxo-1,2-dihydroquinolin-5-yl)ethyl)amino)pentyl)oxy)benzyl)amino)-2,3-dihydro-1H-indene-1-carboxylate (Compound 3)

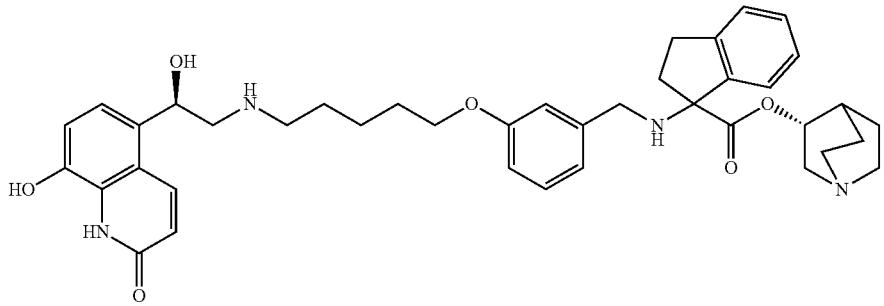 [SMILES: O=C(O[C@H]1CN2CCC1CC2)C1(NCc2cccc(OCCCCCNC[C@H](O)c3ccc(O)c4[nH]c(=O)ccc34)c2)CCc2ccccc21]

The title compound was prepared as described in Example 1 with 3-(4-(1,3-dioxolan-2-yl)butoxy)benzaldehyde replacing N-(4,4-diethoxybutyl)-3-formylbenzamide in Step 2 and the product used in subsequent steps.

$^1$H NMR (400 MHz, MeOD); δ 8.39 (d, J=9.9 Hz, 1H), 7.64 (dd, J=7.7, 17.0 Hz, 1H), 7.54-7.50 (m, 2H), 7.44-7.30 (m, 3H), 7.10-6.99 (m, 4H), 6.68 (d, J=9.8 Hz, 1H), 5.43 (dd, J=5.6, 7.8 Hz, 1H), 5.35-5.25 (m, 1H), 4.30-4.15 (m, 2H), 4.07-4.02 (m, 2H), 3.82-3.71 (m, 1H), 3.46-3.35 (m, 2H), 3.30-3.21 (m, 4H), 3.17-2.97 (m, 4H), 2.89-2.69 (m, 2H), 2.68 (s, 2H), 2.49-2.41 (m, 0.5H), 2.27-2.18 (m, 0.5H), 2.08-1.79 (m, 6H), 1.67-1.59 (m, 3H).

Example 4. (R)-Quinuclidin-3-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate (Compound 4)

The title compound was prepared as described in Example 1 with methyl 5-formylthiophene-2-carboxylate replacing 3-formylbenzoic acid in Step 1 and the product used in subsequent steps.

$^1$H NMR (400 MHz, DMSO-d$_6$ @ 90° C.); δ 8.17 (d, J=9.9 Hz, 1H), 8.12-8.09 (m, 1H), 7.51 (d, J=3.8 Hz, 1H), 7.45 (dd, J=7.5, 16.7 Hz, 1H), 7.33-7.24 (m, 3H), 7.15 (d, J=8.2 Hz, 1H), 7.01 (d, J=8.2 Hz, 1H), 6.93 (d, J=3.6 Hz, 1H), 6.56 (d, J=9.9 Hz, 1H), 5.33 (dd, J=4.4, 8.5 Hz, 1H), 5.11-5.05 (m, 1H), 4.00-3.84 (m, 2H), 3.71-3.65 (m, 1H), 3.30-3.01 (m, 1314), 2.75-2.64 (m, 1H), 2.35-2.16 (m, 1H), 1.93-1.82 (m, 3H), 1.75-1.57 (m, 6H).

Example 5. (R)-Quinuclidin-3-yl 1-(3-((4-(((R)-2-hydroxy-2-(8-hydroxy-2-oxo-1,2-dihydroquinolin-5-yl)ethyl)amino)butyl)carbamoyl)benzyl)amino)-4-methyl-2,3-dihydro-1H-indene-1-carboxylate (Compound 5)

Step 1. 4'-Methyl-2',3'-dihydrospiro[imidazolidine-4,1'-indene]-2,5-dione

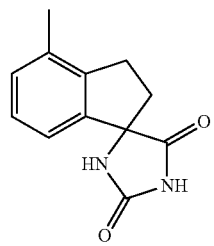 [SMILES: Cc1cccc2c1CCC21NC(=O)NC1=O]

To a solution of 4-methyl-1-indanone (1.0 g, 6.84 mmol) in ethanol/water (45 mL/45 mL) was added ammonium carbonate (5.25 g, 54.72 mmol) and potassium cyanide (0.667 g, 10.26 mmol) and the reaction mixture heated at 60° C. for 72 hours. Further ammonium carbonate (5.25 g, 54.72 mmol) and potassium cyanide (0.667 g, 10.26 mmol) and the reaction stirred at 70° C. for 24 hours. The reaction mixture was cooled and water (100 mL) added. The mixture was stirred for 45 minutes and the resultant suspension was filtered. The solid was washed with water and the solid dried in vacuo to afford the title compound (1.25 g, 85%).

$^1$H NMR (400 MHz, DMSO-d$_6$); δ 10.73-10.70 (m, 1H), 8.40 (s, 1H), 7.19-7.12 (m, 2H), 6.95 (d, J=6.7 Hz, 1H), 2.95-2.89 (m, 2H), 2.58-2.50 (m, 1H), 2.26 (s, 3H), 2.19-2.10 (m, 1H).

Step 2. (R)-quinuclidin-3-yl 1-amino-4-methyl-2,3-dihydro-1H-indene-1-carboxylate

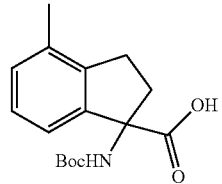 [SMILES: Cc1cccc2c1CCC2(NC(=O)OC(C)(C)C)C(=O)O]

To a pressure vessel was added 4'-methyl-2',3'-dihydrospiro[imidazolidine-4,1'-indene]-2,5-dione (1.25 g, 5.79 mmol), barium hydroxide octahydrate (2.75 g, 8.68 mmol) and water (25 mL). The vessel was sealed and heated at 150° C. for 18 hours. The reaction vessel was cooled and the suspension filtered. The pH of the filtrate was adjusted to pH 7 by the addition of solid carbon dioxide and the result solid filtered. The resultant filtrate was evaporated at reduced pressure. The residue was suspended in 1,4-dioxane (25 mL) and 2M aqueous sodium hydroxide (6.3 mL) was added. To this mixture was added di-tert-butyl dicarbonate (3.4 g, 15.71 mmol) and the reaction mixture was stirred at room temperature for 3 hours. Water added and the pH adjusted to 3 with aqueous 1M hydrochloric acid. The mixture was extracted with ethyl acetate (×2) and the combined organics evaporated at reduced pressure to afford the title compound (2.5 g, 100%).

$^1$H NMR (400 MHz, DMSO-d$_6$); δ 7.40 (s, 1H), 7.26-7.21 (m, 1H), 7.12-7.06 (m, 2H), 2.89-2.76 (m, 4H), 2.26 (s, 3H), 1.47 (s, 9H).

Step 3. (R)-Quinuclidin-3-yl 1-amino-4-methyl-2,3-dihydro-1H-indene-1-carboxylate dihydrochloride

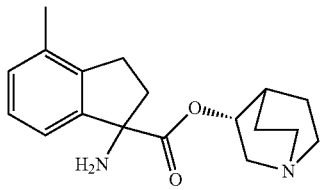 [SMILES: Cc1cccc2c1CCC2(N)C(=O)O[C@H]1CN2CCC1CC2]

The title compound was prepared as described in the synthesis of Intermediate 2 with (R)-quinuclidin-3-yl 1-amino-4-methyl-2,3-dihydro-1H-indene-1-carboxylate replacing 1-((tert-butoxycarbonyl)amino)-2,3-dihydro-1H-indene-1-carboxylic acid in Step 1 and the product used in subsequent steps.

$^1$H NMR (400 MHz, DMSO-d$_6$); δ 10.82-10.77 (m, 1H), 9.43 (d, J=14.7 Hz, 3H), 7.70-7.66 (m, 1H), 7.42-7.31 (m, 2H), 5.14-5.09 (m, 1H), 3.44-3.06 (m, 9H), 2.89-2.83 (m, 1H), 2.44-2.35 (m, 1H), 2.26 (s, 3H), 2.17-2.12 (m, 1H), 1.89 (ddd, J=4.6, 9.2, 18.4 Hz, 1H), 1.82-1.70 (m, 2H).

Step 4. (R)-Quinuclidin-3-yl 1-((3-((4-(((R)-2-hydroxy-2-(8-hydroxy-2-oxo-1,2-dihydroquinolin-5-yl)ethyl)amino)butyl)carbamoyl)benzyl)amino)-4-methyl-2,3-dihydro-1H-indene-1-carboxylate (Compound 5)

The title compound was prepared as described in Example 1 with (R)-quinuclidin-3-yl 1-amino-4-methyl-2,3-dihydro-1H-indene-1-carboxylate dihydrochloride replacing (R)-quinuclidin-3-yl 1-amino-2,3-dihydro-1H-indene-1-carboxylate dihydrochloride in Step 1 and the product used in subsequent steps.

$^1$H NMR (400 MHz, MeOD); δ 8.47 (s, 3H), 8.37 (d, J=9.6 Hz, 1H), 7.83 (s, 1H), 7.72 (d, J=7.6 Hz, 1H), 7.55 (d, J=7.6 Hz, 1H), 7.43 (t, J=8.7 Hz, 1H), 7.32-7.23 (m, 2H), 7.22-7.12 (m, 2H), 7.04 (d, J=8.1 Hz, 1H), 6.67 (d, J=9.1 Hz, 1H), 5.42 (s, 1H), 5.07-5.04 (m, 1H), 3.76 (d, J=2.5 Hz, 2H), 3.65-3.55 (m, 1H), 3.46 (br s, 2H), 3.25 (d, J=3.3 Hz, 2H), 3.21-3.00 (m, 8H), 2.92-2.79 (m, 2H), 2.40-2.31 (m, 6H), 2.06-1.94 (m, 1H), 1.81 (br s, 3H), 1.74 (br s, 3H), 1.65-1.57 (m, 1H).

Example 5A. (R)-Quinuclidin-3-yl 1-(3-((5-(((R)-2-hydroxy-2-(8-hydroxy-2-oxo-1,2-dihydroquinolin-5-yl)ethyl)amino)pentyl)oxy)benzamido)-4-methyl-2,3-dihydro-1H-indene-1-carboxylate (Compound 5A and Compound 5B)

Step 1. (R)-Quinuclidin-3-yl 1-((tert-butoxycarbonyl)amino)-4-methyl-2,3-dihydro-1H-indene-1-carboxylate

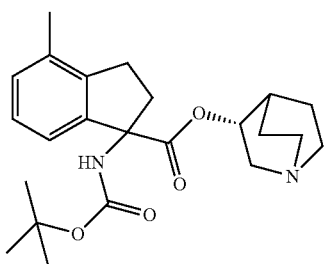

1

The title compound was prepared as described in the synthesis of Intermediate 2 with (R)-quinuclidin-3-yl 1-amino-4-methyl-2,3-dihydro-1H-indene-1-carboxylate replacing (R)-quinuclidin-3-yl 1-amino-2,3-dihydro-1H-indene-1-carboxylate in Step 1.

Compounds 5A and 5B were prepared as single diastereoisomers, as above, using the individual isomers of key intermediate 1 separated by reverse phase preparative HPLC.

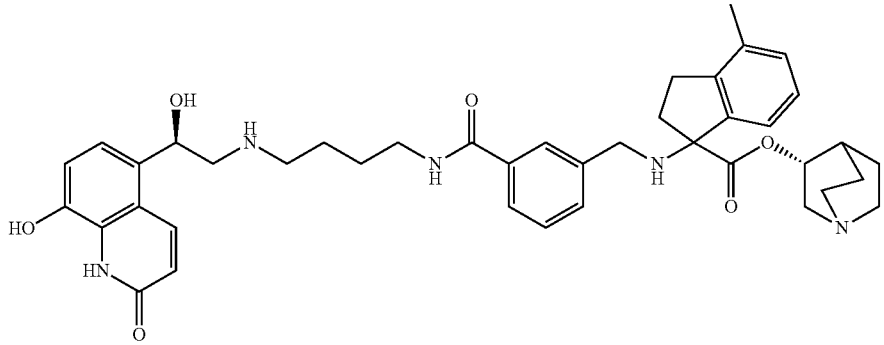 [SMILES: Cc1cccc2c1CCC2(NCc1cccc(C(=O)NCCCCNC[C@H](O)c2ccc(O)c3[nH]c(=O)ccc23)c1)C(=O)O[C@H]1CN2CCC1CC2]

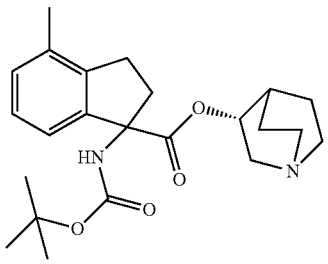

Compound 5A

¹H NMR (400 MHz, DMSO-d₆); δ 7.67 (s, 1H), 7.28 (d, J=7.2 Hz, 1H), 7.16-7.06 (m, 2H), 4.65-4.62 (m, 1H), 3.01 (dd, J=8.0, 14.2 Hz, 1H), 2.92-2.54 (m, 6H), 2.45-2.33 (m, 1H), 2.22 (s, 3H), 2.21-2.08 (m, 1H), 1.81-1.78 (m, 1H), 1.40-1.37 (m, 13H), 1.35-1.21 (m, 1H).

HPLC data (10 cm_ESCI_Bicarb_MeCN) Rt 3.23 min, M+H 401

Compound 5B

¹H NMR (400 MHz, DMSO) d 7.67 (s, 1H), 7.25 (dd, J=1.9, 6.7 Hz, 1H), 7.09 (dd, J=6.7, 6.7 Hz, 2H), 4.62-4.57 (m, 1H), 3.05-2.99 (m, 1H), 2.93-2.80 (m, 3H), 2.73-2.55 (m, 4H), 2.51-2.42 (m, 2H), 2.20-2.07 (m, 1H), 1.82 (d, J=2.9 Hz, 1H), 1.71 (d, J=2.9 Hz, 1H), 1.62-1.43 (m, 3H), 1.40 (s, 9H), 1.31 (dd, J=14.6, 14.6 Hz, 2H). HPLC data (10 cm_ESCI_Bicarb_MeCN) Rt 3.27 min, M+H 401

Step 2.

The two individual stereoisomers were prepared as described in Example 2.

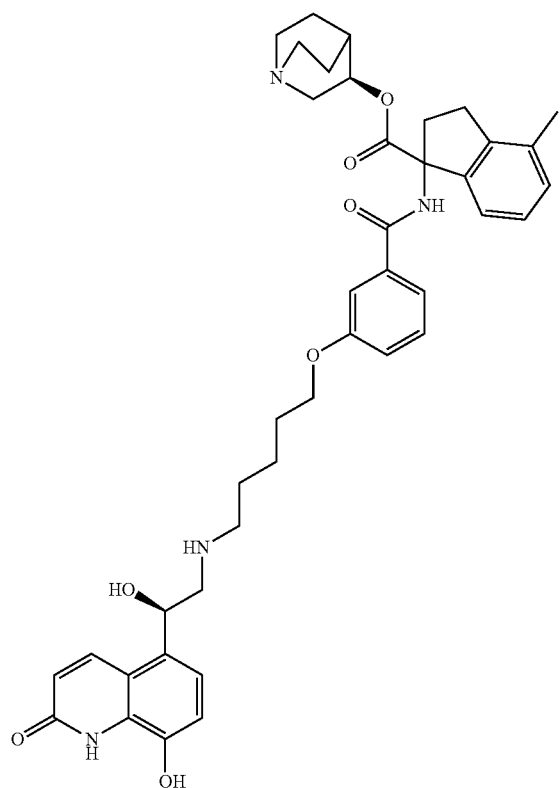 [SMILES: Cc1cccc2c1CCC2(NC(=O)c1cccc(OCCCCCNC[C@H](O)c2ccc(O)c3[nH]c(=O)ccc23)c1)C(=O)O[C@H]1CN2CCC1CC2]

(R)-quinuclidin-3-yl 1-(3-((5-(((R)-2-hydroxy-2-(8-hydroxy-2-oxo-1,2-dihydroquinolin-5-yl)ethyl)amino)pentypoxy)benzamido)-4-methyl-2,3-dihydro-1H-indene-1-carboxylate (Compound 5A_single isomer)

¹H NMR (400 MHz, MeOD); δ 1.39 (d, J=11.2 Hz, 1H), 7.46-7.35 (m, 4H), 7.31 (d, J=8.2 Hz, 1H), 7.25-7.18 (m, 2H), 7.13-7.11 (m, 1H), 7.05 (d, J=8.2 Hz, 1H), 6.70 (d, J=9.9 Hz, 1H), 5.41 (t, J=9.3 Hz, 1H), 5.12-5.08 (m, 1H), 4.08 (t, J=7.5 Hz, 2H), 3.73 (ddd, J=2.5, 8.4, 14.2 Hz, 1H), 3.27 (t, J=11.2 Hz, 8H), 3.17-3.03 (m, 4H), 2.32 (s, 5H), 2.05 (dd, J=16.8, 27.9 Hz, 2H), 1.87 (tt, J=18.0, 17.7 Hz, 6H), 1.68-1.59 (m, 2H).

(R)-quinuclidin-3-yl 1-(3-((5-(((R)-2-hydroxy-2-(8-hydroxy-2-oxo-1,2-dihydroquinolin-5-yl)ethyl)amino)pentyl)oxy)benzamido)-4-methyl-2,3-dihydro-1H-indene-1-carboxylate (Compound 5B_single isomer)

¹H NMR (400 MHz, MeOD); δ 8.38 (d, J=9.9 Hz, 1H), 7.47 (d, J=7.8 Hz, 1H), 7.43-7.36 (m, 3H), 7.31 (d, J=8.4 Hz, 1H), 7.26-7.19 (m, 2H), 7.14-7.11 (m, 1H), 7.05 (d, J=8.2 Hz, 1H), 6.70 (d, J=9.8 Hz, 1H), 5.41 (1H, t, J=8.7 Hz), 5.05-4.98 (m, 1H), 4.07 (t, J=7.3 Hz, 2H), 3.72 (ddd, J=2.6, 8.2, 14.1 Hz, 1H), 3.38 (dd, J=7.3, 19.6 Hz, 1H), 3.34-3.32 (m, 1H), 3.30-3.24 (m, 6H), 3.14 (ddd, J=6.7, 6.7, 6.7 Hz, 2H), 3.06 (dd, J=8.6, 11.0 Hz, 3H), 2.39 (d, J=17.1 Hz, 1H), 2.33-2.25 (m, 4H), 2.06-1.84 (m, 7H), 1.68-1.59 (m, 2H).

Example 6. (R)-Quinuclidin-3-yl 1-(3-(4-(((R)-2-hydroxy-2-(8-hydroxy-2-oxo-1,2-dihydroquinolin-5-yl)ethyl)amino)butoxy)benzamido)-2,3-dihydro-1H-indene-1-carboxylate (Compound 6)

The title compound was prepared as described in Example 2 with 2-(3-chloropropyl)-1,3-dioxalane replacing 2-(4-chlorobutyl)-1,3-dioxalane in Step 1 and the product used in subsequent steps.

¹H NMR (400 MHz, DMSO-d₆); δ 10.51 (d, J=3.9 Hz, 2H), 9.78-9.78 (m, 1H), 9.29 (d, J=37.0 Hz, 1H), 8.67 (s, 2H), 8.17 (d, J=9.9 Hz, 1H), 7.63-7.32 (m, 6H), 7.31-7.24 (m, 1H), 7.17-7.09 (m, 2H), 6.99 (d, J=8.2 Hz, 1H), 6.58 (d, J=9.9 Hz, 1H), 6.20-6.19 (m, 1H), 5.32 (d, J=9.2 Hz, 1H), 5.03-4.99 (m, 1H), 4.02 (s, 2H), 3.70-3.63 (m, 1H), 3.24-2.98 (m, 11H), 2.37-2.17 (m, 2H), 1.68-1.60 (m, 8H).

Example 7. (1-Isopropylpiperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate
(Compound 7)

Step 1. (R)-8-(Benzyloxy)-5-(1-((tert-butyldimethylsilyl)oxy)-2-((6-hydroxyhexyl)amino)ethyl)quinolin-2(1H)-one

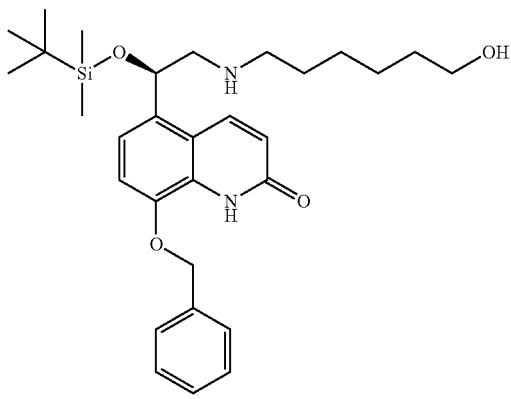 [SMILES: CC(C)(C)[Si](C)(C)O[C@@H](CNCCCCCCO)c1ccc(OCc2ccccc2)c2[nH]c(=O)ccc12]

To a solution of (R)-8-(benzyloxy)-5-(2-bromo-1-((tert-butyldimethylsilyl)oxy)ethyl)quinolin-2(1H)-one (5.01 g, 10.24 mmol) in NMP (19 mL) was added 6-amino-1-hexanol (5.99 g, 51.22 mmol). The reaction mixture was heated at 80° C. for 18 hours. The reaction mixture was diluted with ethyl acetate and washed with water and brine (×2). The organic phase was dried over anhydrous magnesium sulfate, filtered and the filtrate concentrated at reduced pressure to afford the title compound (5.36 g, 100%).

$^1$H NMR (400 MHz, CDCl$_3$); δ 8.25 (d, J=9.9 Hz, 1H), 7.38-7.33 (m, 5H), 7.07 (d, J=8.2 Hz, 1H), 6.94 (d, J=8.2 Hz, 1H), 6.60-6.58 (m, 1H), 5.09 (s, 2H), 5.08-5.06 (m, 1H), 4.08-4.01 (m, 2H), 3.60-3.52 (m, 3H), 3.34-3.27 (m, 1H), 2.90-2.81 (m, 1H), 2.70-2.49 (m, 3H), 1.55-1.39 (m, 2H), 1.30 (d, J=2.5 Hz, 2H), 0.81 (s, 9H), 0.00 (s, 3H), −0.26 (s, 3H).

Step 2. (R)-tert-Butyl (2-(8-(benzyloxy)-2-oxo-1,2-dihydroquinolin-5-yl)-2-((tert-butyldimethylsilyl)oxy)ethyl)(6-hydroxyhexyl)carbamate

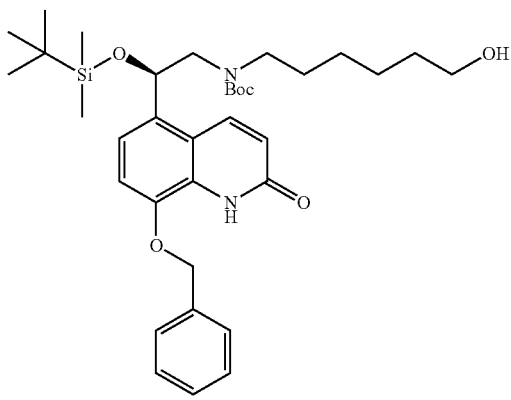 [SMILES: CC(C)(C)OC(=O)N(CCCCCCO)C[C@H](O[Si](C)(C)C(C)(C)C)c1ccc(OCc2ccccc2)c2[nH]c(=O)ccc12]

To a stirred solution of (R)-8-(benzyloxy)-5-(1-((tert-butyldimethylsilyl)oxy)-2-((6-hydroxyhexyl)amino)ethyl)quinolin-2(1H)-one (5.36 g, 10.24 mmol) in DCM (50 mL) was added di-tert-butyldicarbonate (4.47 g, 20.48 mmol). The reaction mixture was stirred at room temperature for 18 hours. The solvent was concentrated at reduced pressure and the residue purified by flash column chromatography (eluent 100% i-hexane to 100% ethyl acetate) to afford the title compound (4.05 g, 63%).

$^1$H NMR (400 MHz, CDCl$_3$); δ 9.17 (s, 1H), 8.54-8.45 (m, 1H), 7.46-7.26 (m, 5H), 7.12-6.99 (m, 1H), 6.79-6.62 (m, 1H), 5.49 (s, 1H), 5.23-5.15 (m, 2H), 3.66-2.91 (m, 6H), 1.64-1.16 (m, 17H), 0.91-0.85 (s, 9H), 0.06 (s, 3H), −0.13 (s, 3H).

Step 3. (R)-methyl 3-((6-((2-(8-(benzyloxy)-2-oxo-1,2-dihydroquinolin-5-yl)-2-((tert-butyldimethylsilyl)oxy)ethyl)(tert-butoxycarbonyl)amino)hexyl)oxy)benzoate

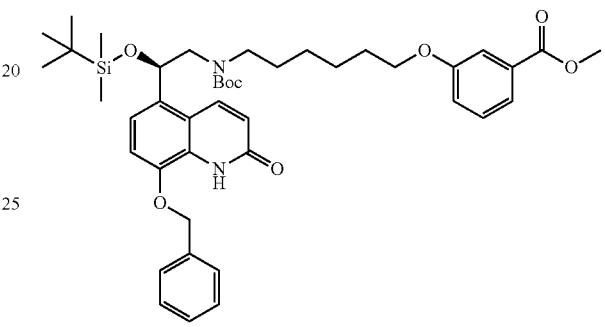

To a stirred solution of (R)-tert-butyl (2-(8-(benzyloxy)-2-oxo-1,2-dihydroquinolin-5-yl)-2-((tert-butyldimethylsilyl)oxy)ethyl)(6-hydroxyhexyl)carbamate (0.5 g, 0.8 mmol), methyl 3-hydroxybenzoate (0.133 g, 0.88 mmol) and triphenylphosphine (0.26 g, 0.98 mmol) in DCM was added DIAD (0.19 g, 0.98 mmol). The reaction mixture was stirred at room temperature for 16 hours. The solvent was concentrated at reduced pressure and the residue purified by column chromatography (eluent 100% i-hexane to 50% ethyl acetate/i-hexane) to afford the title compound (0.52 g, 86%).

$^1$H NMR (400 MHz, CDCl$_3$); δ 9.17 (s, 1H), 8.54-8.45 (m, 1H), 8.00-7.96 (m, 2H), 7.46-7.26 (m, 5H), 7.12-6.99 (m, 1H), 6.90-6.86 (m, 2H), 6.79-6.62 (m, 1H), 5.49 (s, 1H), 5.23-5.15 (m, 2H), 3.88 (s, 3H), 3.66-2.91 (m, 6H), 1.64-1.16 (m, 17H), 0.91-0.85 (s, 9H), 0.06 (s, 3H), −0.13 (s, 3H).

Step 4. (R)-3-((6-((2-(8-(Benzyloxy)-2-oxo-1,2-dihydroquinolin-5-yl)-2-((tert-butyldimethylsilyl)oxy)ethyl)(tert-butoxycarbonyl)amino)hexyl)oxy)benzoic acid

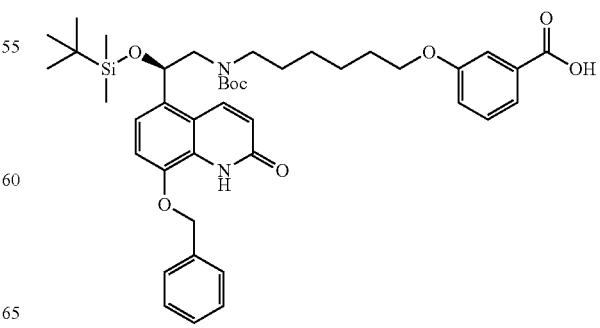

To a stirred solution of (R)-methyl 3-((6-((2-(8-(benzyloxy)-2-oxo-1,2-dihydroquinolin-5-yl)-2-((tert-butyldimethylsilyl)oxy)ethyl)(tert-butoxycarbonyl)amino)hexyl)oxy)benzoate (0.52 g, 0.68 mmol) in methanol/THF/water (14 mL/40 mL/14 mL) was added lithium hydroxide monohydrate (0.114 g, 2.72 mmol). The reaction mixture was stirred at room temperature for 18 hours. The reaction mixture was quenched with 1M aqueous hydrochloric acid and extracted with ethyl acetate. The organic phase was dried over anhydrous magnesium sulfate, filtered and the filtrate concentrated at reduced pressure to afford the title compound (0.46 g, 91%).

$^1$H NMR (400 MHz, DMSO-d$_6$); δ 9.14-9.06 (m, 3H), 7.51-7.47 (m, 1H), 7.42-7.31 (m, 8H), 5.06 (s, 2H), 4.05-3.88 (m, 4H), 3.23-3.05 (m, 2H), 2.80-2.67 (m, 3H), 2.44-2.29 (m, 1H), 1.82-1.70 (m, 1H), 1.56-1.46 (m, 2H), 1.06-0.92 (m, 2H).

Step 6. Piperidin-4-ylmethyl 1-(3-((6-((tert-butoxycarbonyl)((R)-2-((tert-butyldimethylsilyl)oxy)-2-(8-hydroxy-2-oxo-1,2-dihydroquinolin-5-yl)ethyl)amino)hexyl)oxy)benzamido)-2,3-dihydro-1H-indene-1-carboxylate

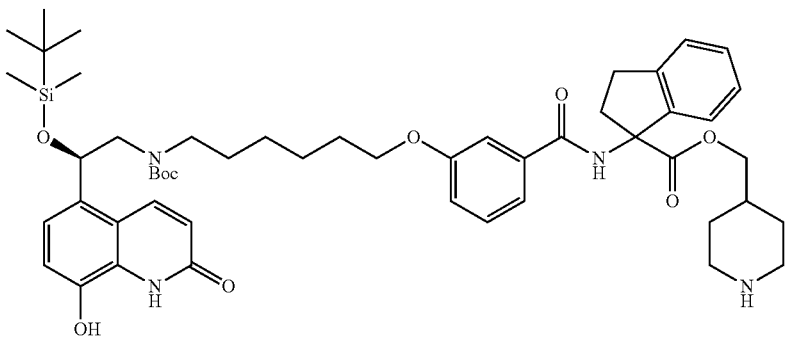

$^1$H NMR (400 MHz, CDCl$_3$); δ 9.17 (s, 1H), 8.54-8.45 (m, 1H), 8.00-7.96 (m, 2H), 7.46-7.26 (m, 5H), 7.12-6.99 (m, 1H), 6.90-6.86 (m, 2H), 6.79-6.62 (m, 1H), 5.49 (s, 1H), 5.23-5.15 (m, 2H), 3.66-2.91 (m, 6H), 1.64-1.16 (m, 17H), 0.91-0.85 (s, 9H), 0.06 (s, 3H), −0.13 (s, 3H).

Step 5. Benzyl 4-(((1-amino-2,3-dihydro-1H-indene-1-carbonyl)oxy)methyl)piperidine-1-carboxylate hydrochloride

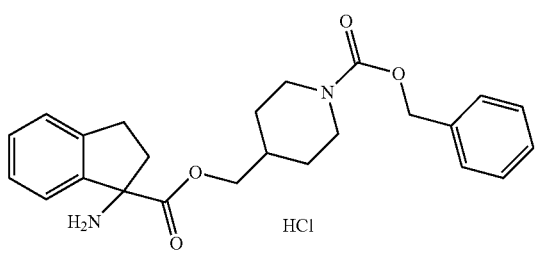 [SMILES: NC1(C(=O)OCC2CCN(C(=O)OCc3ccccc3)CC2)CCc2ccccc21 ; Cl]

To a solution of 1-((tert-butoxycarbonyl)amino)-2,3-dihydro-1H-indene-1-carboxylic acid (1.21 g, 4.4 mmol) in DMF (15 mL) was added potassium carbonate (0.729 g, 5.28 mmol) and benzyl 4-((tosyloxy)methyl)piperidine-1-carboxylate (1.78 g, 4.84 mmol). The reaction mixture was stirred at 80° C. for 16 hours. The reaction mixture was diluted with ethyl acetate and washed with water and brine (×2). The organic phase was dried over anhydrous magnesium sulfate, filtered and the filtrate concentrated at reduced pressure. The residue was purified by flash column chromatography (eluent—100% iso-hexane to 1:1 ethyl acetate/iso-hexane) to afford the title compound. The residue was diluted with a solution of HCl in dioxin (4M, 10 mL) and stirred for 4 hours. The solvent evaporated at reduced pressure to afford the title compound (1.8 g, 92%).

To a stirred mixture of benzyl 4-(((1-amino-2,3-dihydro-1H-indene-1-carbonyl)oxy)methyl)piperidine-1-carboxylate hydrochloride (2.13 g, 3.93 mmol) and (R)-3-((6-((2-(8-(benzyloxy)-2-oxo-1,2-dihydroquinolin-5-yl)-2-((tert-butyldimethylsilyl)oxy)ethyl)(tert-butoxycarbonyl)amino)hexyl)oxy)benzoic acid (2.65 g, 3.57 mmol) in DCM (50 mL) was added DIPEA (1.53 mL, 8.9 mmol) and HATU (1.62 g, 4.28 mmol). The reaction mixture was stirred at room temperature for 16 hours. The reaction mixture was washed with saturated aqueous sodium hydrogen carbonate and the organic phase passed through a hydrophobic frit. The solvent was evaporated at reduced pressure and the residue was purified by flash column chromatography (eluent; 100% iso-hexane to 1:1 ethyl acetate/iso-hexane). The residue (2.0 g, 1.76 mmol) was dissolved in ethanol (50 mL) and 10% palladium on carbon (1.0 g) added followed by 1-methyl-1,4-cyclohexadiene (1.0 mL, 8.8 mmol). The mixture was heated at 50° C. for two hours. The suspension was filtered and the filtrate evaporated at reduced pressure to afford the title compound (0.91 g, 25%).

Step 7. (1-Isopropylpiperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate (Compound 7)

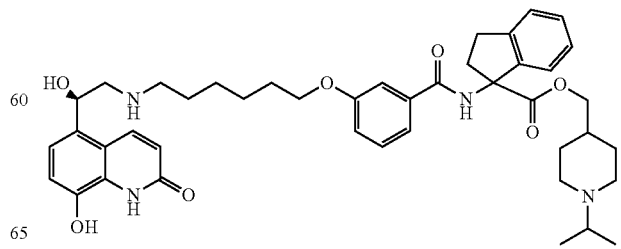

To a solution of piperidin-4-ylmethyl 1-(3-((6-((tert-butoxycarbonyl)((R)-2-((tert-butyldimethylsilyl)oxy)-2-(8-hydroxy-2-oxo-1,2-dihydroquinolin-5-yl)ethyl)amino)hexyl)oxy)benzamido)-2,3-dihydro-1H-indene-1-carboxylate (0.112 g, 0.12 mmol) in DCM (2 mL) was added acetone (0.014 g, 0.24 mmol) and the mixture stirred for 10 minutes. Sodium triacetoxyborohydride (0.03 g, 0.14 mmol) was added and the reaction mixture stirred for 72 hours. Saturated aqueous sodium hydrogen carbonate added and the mixture poured through a hydrophobic fit. The filtrate was evaporated at reduced pressure. The residue was treated with a solution of HCl in dioxane (2 mL) and stirred at room temperature for 30 minutes. The solvent was evaporated at reduced pressure. The residue was purified by reverse phase preparative HPLC to afford the title compound.

$^1$H NMR (400 MHz, DMSO-$d_6$); δ 10.52 (s, 2H), 9.11 (s, 1H), 8.94-8.93 (m, 1H), 8.59-8.58 (m, 2H), 8.16 (d, J=9.9 Hz, 1H), 7.53 (d, J=7.5 Hz, 1H), 7.48 (d, J=7.8 Hz, 1H), 7.44 (dd, J=2.1, 2.1 Hz, 1H), 7.39-7.33 (m, 3H), 7.29-7.23 (m, 1H), 7.15 (d, J=8.2 Hz, 1H), 7.09 (dd, J=2.0, 8.0 Hz, 1H), 6.99 (d, J=8.2 Hz, 1H), 6.59 (d, J=9.8 Hz, 1H), 5.31 (dd, J=2.7, 10.0 Hz, 1H), 4.00 (dd, J=6.3, 6.3 Hz, 2H), 3.89 (d, J=6.5 Hz, 2H), 3.48-3.38 (m, 1H), 3.31 (d, J=11.3 Hz, 2H), 3.13-2.87 (m, 8H), 2.30-2.20 (m, 1H), 1.95-1.59 (m, 7H), 1.47-1.35 (m, 6H), 1.21 (d, J=6.7 Hz, 6H).

Example 8. (R)-Quinuclidin-3-yl 1-(3-((4-(((R)-2-hydroxy-2-(8-hydroxy-2-oxo-1,2-dihydroquinolin-5-yl)ethyl)amino)butyl)carbamoyl)benzamido)-2,3-dihydro-1H-indene-1-carboxylate (Compound 8)

Step 1. Methyl 3-((4,4-diethoxybutyl)carbamoyl)benzoate

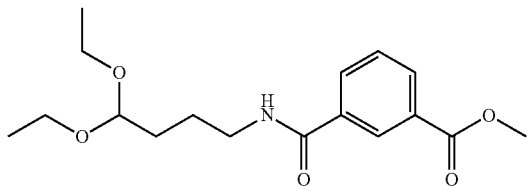 [SMILES: CCOC(CCCNC(=O)c1cccc(C(=O)OC)c1)OCC]

To a solution of mono-methyl isophthalate (0.50 g, 2.77 mmol) in DMF (5 mL) was added DIPEA (0.55 mL, 3 mmol) and HATU (1.15 g, 3.0 mmol) and the mixture stirred at room temperature for 45 minutes. 4,4-Diethoxybutan-1-amine (0.375 g, 2.3 mmol) was added and the reaction mixture stirred at room temperature for 18 hours. The reaction mixture was diluted with ethyl acetate and washed with saturated aqueous sodium carbonate (×2) and brine. The organic phase was dried over anhydrous magnesium sulfate, filtered and the filtrate evaporated at reduced pressure to afford the title compound (0.95 g, >100%).

$^1$H NMR (400 MHz, DMSO-$d_6$); δ 8.69 (dd, J=5.5, 5.5 Hz, 1H), 8.44 (dd, J=1.6, 1.6 Hz, 1H), 8.12-8.08 (m, 2H), 7.63 (dd, J=7.8, 7.8 Hz, 1H), 4.51-4.47 (m, 1H), 3.90 (s, 3H), 3.56 (ddd, J=7.1, 9.5, 14.1 Hz, 2H), 3.43 (ddd, J=7.0, 9.5, 14.1 Hz, 2H), 3.29-3.26 (m, 2H), 1.57-1.54 (m, 4H), 1.11 (dd, J=7.1, 7.1 Hz, 6H).

Step 2; 3-((4,4-Diethoxybutyl)carbamoyl)benzoic acid

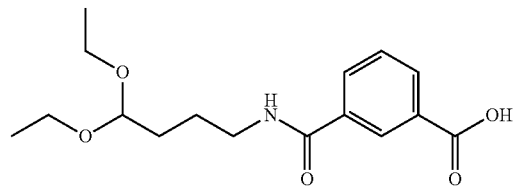 [SMILES: CCOC(CCCNC(=O)c1cccc(C(=O)O)c1)OCC]

To a solution of methyl 3-((4,4-diethoxybutyl)carbamoyl)benzoate (0.95 g, 2.94 mmol) in THF/MeOH (15 mL/15 mL) was added a 2M aqueous sodium hydroxide (15 mL) and the reaction mixture stirred at room temperature for 2 hours. The reaction mixture was evaporated at reduced pressure to half the initial volume and the treated with 1M aqueous hydrochloric acid to pH 4. The mixture was extracted with ethyl acetate (×3) and the combined organic extracts dried over anhydrous magnesium sulfate, filtered and the filtrate evaporated at reduced pressure to afford the title compound (0.90 g, 99%).

$^1$H NMR (400 MHz, DMSO-$d_6$); δ 8.71-8.64 (m, 1H), 8.42 (s, 1H), 8.07 (dd, J=1.8, 7.8 Hz, 2H), 7.60 (dd, J=7.7, 7.7 Hz, 1H), 4.51-4.46 (m, 1H), 3.56 (ddd, J=7.1, 9.5, 14.1 Hz, 2H), 3.46-3.26 (m, 4H), 1.58-1.55 (m, 4H), 1.11 (dd, J=7.1, 7.1 Hz, 6H).

Step 3. (R)-Quinuclidin-3-yl 1-(3-((4-(((R)-2-hydroxy-2-(8-hydroxy-2-oxo-1,2-dihydroquinolin-5-yl)ethyl)amino)butyl)carbamoyl)benzamido)-2,3-dihydro-1H-indene-1-carboxylate (Compound 8)

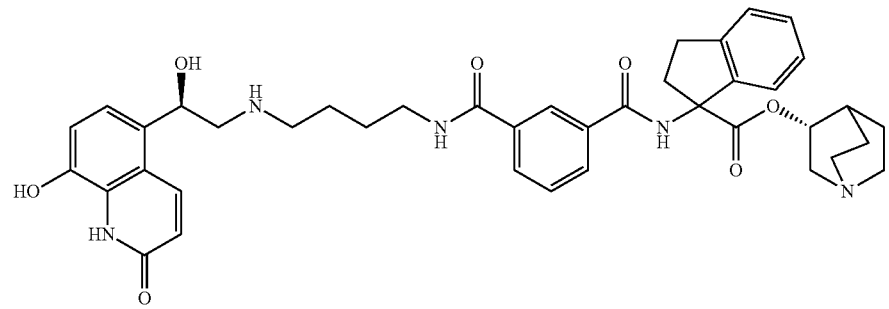 [SMILES: O=C(NCCCCNC[C@H](O)c1ccc(O)c2[nH]c(=O)ccc12)c1cccc(C(=O)NC2(C(=O)O[C@H]3CN4CCC3CC4)CCc3ccccc32)c1]

The title compound was prepared as described in Example 2 with 3-((4,4-diethoxybutyl)carbamoyl)benzoic acid replacing 3-(4-(1,3-dioxolan-2-yl)butoxy)benzoic acid in Step 3 and the product used in subsequent steps.

$^1$H NMR (400 MHz, MeOD); δ 8.52 (s, 2H), 8.40-8.33 (m, 2H), 8.06-7.99 (m, 2H), 7.65-7.57 (m, 2H), 7.37 7.28 (m, 4H), 7.04 (d, J=8.2 Hz, 1H), 6.68 (d, J=9.9 Hz, 1H), 5.41 (dd, J=6.7, 6.7 Hz, 1H), 5.07-4.97 (m, 1H), 3.61-3.50 (m, 1H), 3.47 (dd, J=6.7, 6.7 Hz, 3H), 3.39-3.04 (m, 5H), 3.01-2.92 (m, 1H), 2.44-2.29 (m, 2H), 2.23-2.17 (m, 1H), 2.06-1.89 (m, 3H), 1.86-1.66 (m, 9H).

Example 9. (1-Benzylpiperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate (Compound 9)

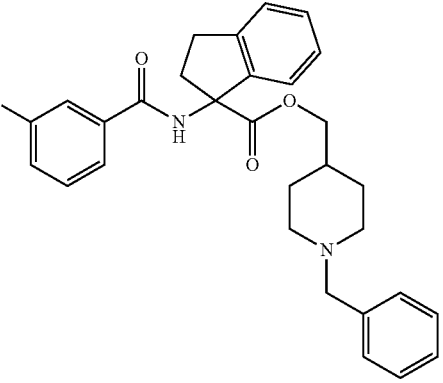

The title compound was prepared as described in Example 7 with benzaldehyde replacing acetone in Step 7.

$^1$H NMR (400 MHz, MeOD); δ 1.39 (d, J=9.9 Hz, 1H), 7.56 (d, J=8.7 Hz, 5H), 7.51 (s, 5H), 7.41-7.26 (m, 4H), 7.12-7.09 (m, 1H), 7.05 (d, J=8.2 Hz, 1H), 6.70 (d, J=9.8 Hz, 1H), 5.41 (dd, J=6.8, 6.8 Hz, 1H), 4.29 (s, 2H), 4.07-4.01 (m, 4H), 3.50-3.43 (m, 2H), 3.29-3.22 (m, 4H), 3.11 (dd, J=7.8, 7.8 Hz, 4H), 3.02-2.94 (m, 2H), 2.37-2.28 (m, 1H), 1.99-1.76 (m, 6H), 1.61-1.46 (m, 6H).

Example 10. (1-(Furan-2-ylmethyl)piperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate (Compound 10)

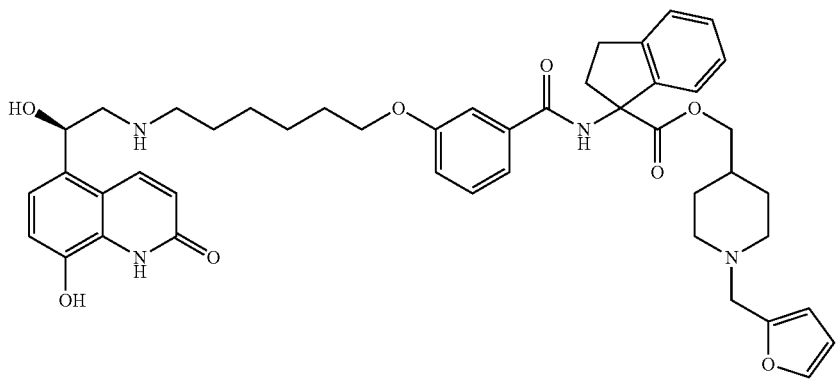 [SMILES: O=C(NC1(C(=O)OCC2CCN(Cc3ccco3)CC2)CCc2ccccc21)c1cccc(OCCCCCCNC[C@H](O)c2ccc(O)c3[nH]c(=O)ccc23)c1]

The title compound was prepared as described in Example 7 with furan-2-carbaldehyde replacing acetone in Step 7.

$^1$H NMR (400 MHz, MeOD); δ 9.03-9.03 (m, 1H), 8.39 (d, J=9.9 Hz, 1H), 7.69 (s, 1H), 7.56 (d, J=7.5 Hz, 1H), 7.43-7.27 (m, 7H), 7.13-7.09 (m, 1H), 7.05 (d, J=8.2 Hz, 1H), 6.70 (d, J=9.9 Hz, 2H), 6.56-6.53 (m, 1H), 5.42 (dd, J=6.7, 6.7 Hz, 1H), 4.38 (s, 2H), 4.04 (dd, J=6.1, 6.1 Hz, 4H), 3.46-3.42 (m, 2H), 3.30-3.23 (m, 3H), 3.15-3.08 (m, 4H), 2.97-2.96 (m, 2H), 2.38-2.28 (m, 1H), 2.01-1.76 (m, 6H), 1.62-1.48 (m, 7H).

Example 11. (1-(3-Hydroxybenzyl)piperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate (Compound 11)

To a solution of methyl 3-(hydroxymethyl)benzoate (0.30 g, 1.8 mmol) in DMF (5 mL), cooled to 0° C., was added sodium hydride (60% dispersion in mineral oil, 0.086 g, 2.15 mmol). The reaction mixture was stirred at this temperature for 10 minutes and then at room temperature for 20 minutes.

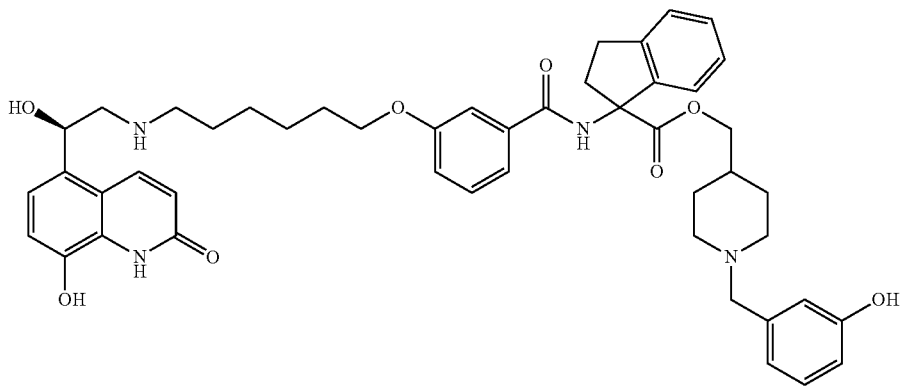 [SMILES: O=C(NC1(C(=O)OCC2CCN(Cc3cccc(O)c3)CC2)CCc2ccccc21)c1cccc(OCCCCCCNC[C@H](O)c2ccc(O)c3[nH]c(=O)ccc23)c1]

The title compound was prepared as described in Example 7 with 3-hydroxybenzaldehyde replacing acetone in Step 7.
¹H NMR (400 MHz, DMSO, 90° C.); δ 8.69 (s, 1H), 8.18 (d, J=9.9 Hz, 1H), 7.54 (d, J=7.7 Hz, 1H), 7.45 (d, J=7.8 Hz, 1H), 7.41-7.40 (m, 1H), 7.36-7.30 (m, 3H), 7.26-7.18 (m, 2H), 7.15 (d, J=8.3 Hz, 1H), 7.07 (dd, J=2.1, 8.0 Hz, 1H), 7.01 (d, J=8.2 Hz, 1H), 6.86-6.82 (m, 3H), 6.57 (d, J=9.9 Hz, 1H), 5.33 (dd, J=4.4, 8.7 Hz, 1H), 4.03 (t, J=6.4 Hz, 2H), 3.95 (s, 2H), 3.17-2.99 (m, 16H), 2.39-2.30 (m, 2H), 1.79-1.67 (m, 6H), 1.51-1.40 (m, 6H).

Example 12. (R)-Quinuclidin-3-yl 1-(3-((4-(((R)-2-hydroxy-2-(8-hydroxy-2-oxo-1,2-dihydroquinolin-5-yl)ethyl)amino)butoxy)methyl)benzamido)-2,3-dihydro-1H-indene-1-carboxylate (Compound 12)

Step 1. 3-((3-(1,3-Dioxolan-2-yl)propoxy)methyl)benzoic acid

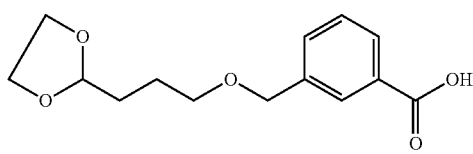 [SMILES: O=C(O)c1cccc(COCCCC2OCCO2)c1]

2-(3-chloropropyl)-1,3-dioxalane (0.25 g, 1.8 mmol) was added and the reaction stirred room temperature for 5 hours. The reaction mixture was quenched with water and saturated aqueous sodium carbonate added. The mixture extracted with ethyl acetate (×3) and the combined organic extracts dried over anhydrous magnesium sulfate, filtered and the filtrate evaporated at reduced pressure. The residue was diluted with THF/MeOH (4.5 mL/4.5 mL) and 2M aqueous sodium hydroxide (4.5 mL) added. The reaction mixture was stirred at room temperature for 2 hours. The reaction mixture was concentrated under reduced pressure to half the volume and the pH adjusted with aqueous 1M hydrochloric acid. The mixture was extracted with ethyl acetate (×2) and the combined organic extracts dried over anhydrous magnesium sulfate, filtered and the filtrate evaporated at reduced pressure to afford the title compound (0.25 g, 52%).

¹H NMR (400 MHz, DMSO-d₆); δ 7.90-7.85 (m, 2H), 7.56-7.45 (m, 2H), 4.80 (dd, J=4.2, 4.2 Hz, 1H), 4.52 (s, 2H), 3.89-3.73 (m, 4H), 3.47 (dd, J=6.0, 6.0 Hz, 2H), 1.65-1.62 (m, 4H).

Step 2. (R)-Quinuclidin-3-yl 1-(3-((4-(((R)-2-hydroxy-2-(8-hydroxy-2-oxo-1,2-dihydroquinolin-5-yl)ethyl)amino)butoxy)methyl)benzamido)-2,3-dihydro-1H-indene-1-carboxylate (Compound 12)

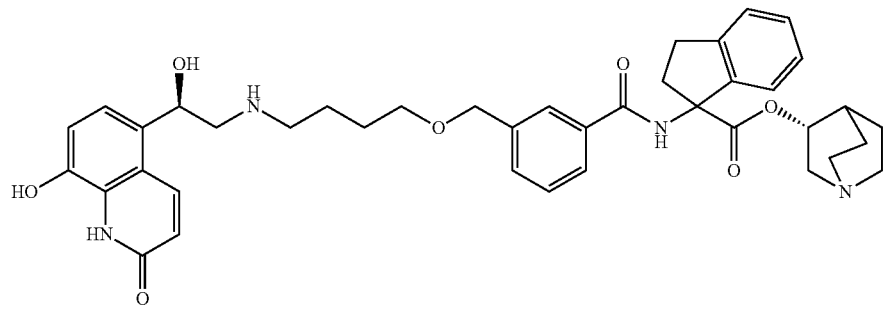 [SMILES: O=C(NC1(C(=O)O[C@H]2CN3CCC2CC3)CCc2ccccc21)c1cccc(COCCCCNC[C@H](O)c2ccc(O)c3[nH]c(=O)ccc23)c1]

The title compound was prepared as described in Example 2 with 3-((3-(1,3-dioxolan-2-yl)propoxy)methyl)benzoic acid replacing 3-(4-(1,3-dioxolan-2-yl)butoxy)benzoic acid in Step 3 and the product used in subsequent steps.

$^1$H NMR (400 MHz, MeOD); δ 8.35 (d, J=1.4, 9.9 Hz, 1H), 7.87 (d, J=7.0 Hz, 1H), 7.81 (dd, J=7.4, 7.4 Hz, 1H), 7.63-7.57 (m, 2H), 7.50-7.44 (m, 1H), 7.38-7.35 (m, 2H), 7.35-7.27 (m, 2H), 7.05 (d, J=8.2 Hz, 1H), 6.68 (d, J=9.9 Hz, 1H), 5.40-5.35 (m, 1H), 5.12-4.92 (m, 1H), 4.59 (s, 2H), 3.77-3.68 (m, 1H), 3.61 (dd, J=5.9, 5.9 Hz, 2H), 3.30-3.20 (m, 7H), 3.19-3.05 (m, 5H), 2.40-2.25 (m, 2H), 2.08-1.74 (m, 8H).

Example 13. (R)-Quinuclidin-3-yl 2-(3-((5-(((R)-2-hydroxy-2-(8-hydroxy-2-oxo-1,2-dihydroquinolin-5-yl)ethyl)amino)pentyl)oxy)benzamido)-2,3-dihydro-1H-indene-2-carboxylate (Compound 13)

Step 1. (R)-Quinuclidin-3-yl 2-amino-2,3-dihydro-1H-indene-2-carboxylate dihydrochloride

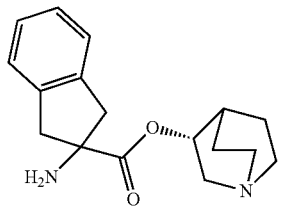

HCl  HCl

To a solution of 2-((tert-butoxycarbonyl)amino)-2,3-dihydro-1H-indene-2-carboxylic acid (0.277 g, 1.0 mmol) in DMF (3 mL) was added CDI (0.195 g, 1.2 mmol) and the reaction mixture stirred at 50° C. for 40 minutes. (R)-3-quinuclidinol (0.382 g, 3.0 mmol) was added and the mixture stirred at this temperature for 5 days. The reaction mixture was diluted with ethyl acetate and washed sequentially with water, 10% aqueous potassium carbonate and brine (×2). The organic phase was dried over magnesium sulfate, filtered and the filtrate evaporated at reduced pressure. The residue was dissolved in a solution of HCl in dioxane (4M, 3 mL) and the reaction mixture stirred at room temperature for 3 hours. The solvent was evaporated to afford the title compound (0.35 g, 98%).

$^1$H NMR (400 MHz, DMSO-d$_6$); δ 10.70 (s, 1H), 9.13 (s, 3H), 7.30-7.29 (m, 2H), 7.27-7.23 (m, 2H), 5.12 (dd, J=4.6, 4.6 Hz, 1H), 3.68-3.50 (m, 3H), 3.44-3.34 (m, 3H), 3.24-3.09 (m, 4H), 2.24-2.23 (m, 1H), 1.94-1.75 (m, 3H), 1.68-1.63 (m, 1H).

Step 2. (R)-Quinuclidin-3-yl 2-(3-((5-(((R)-2-hydroxy-2-(8-hydroxy-2-oxo-1,2-dihydroquinolin-5-yl)ethyl)amino)pentyl)oxy)benzamido)-2,3-dihydro-1H-indene-2-carboxylate (Compound 13)

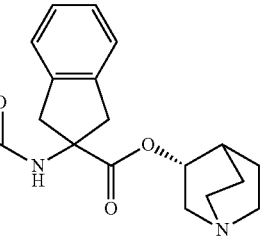

The title compound was prepared as described in Example 2 with (R)-quinuclidin-3-yl 1-amino-2,3-dihydro-1H-indene-2-carboxylate dihydrochloride replacing (R)-quinuclidin-3-yl 1-amino-2,3-dihydro-1H-indene-1-carboxylate dihydrochloride in Step 3 and the product used in subsequent steps.

$^1$H NMR (400 MHz, MeOD); δ 8.52 (s, 2H), 8.39 (d, J=9.9 Hz, 1H), 7.44-7.34 (m, 3H), 7.32-7.19 (m, 6H), 7.13-7.10 (m, 1H), 7.05 (d, J=8.2 Hz, 1H), 6.70 (d, J=9.8 Hz, 1H), 5.41 (dd, J=6.8, 6.8 Hz, 1H), 5.09-5.03 (m, 1H), 4.07 (dd, J=6.1, 6.1 Hz, 2H), 3.84 (d, J=16.7 Hz, 1H), 3.69 (d, J=16.6 Hz, 1H), 3.59 (ddd, J=2.5, 8.3, 14.3 Hz, 1H), 3.50-3.35 (m, 2H), 3.24 (d, J=6.8 Hz, 2H), 3.16-3.08 (m, 6H), 2.96-2.85 (m, 1H), 2.26-2.23 (m, 1H), 2.01-1.78 (m, 7H), 1.68-1.60 (m, 3H).

Example 14. (R)-Quinuclidin-3-yl 2-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-2-carboxylate (Compound 14)

Step 1. N-(4,4-Diethoxybutyl)-5-formylthiophene-2-carboxamide

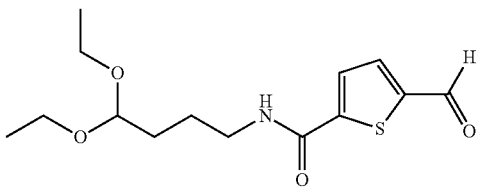 [SMILES: CCOC(CCCNC(=O)c1ccc(C=O)s1)OCC]

The title compound was prepared as described in Example Step 1 with 5-formylthiophene-2-carboxylic acid replacing 3-formylbenzoic acid.

$^1$H NMR (400 MHz, DMSO-d$_6$); δ 9.96 (s, 1H), 8.81 (dd, J=5.6, 5.6 Hz, 1H), 8.02 (d, J=4.0 Hz, 1H), 7.87 (d, J=4.0 Hz, 1H), 4.50-4.46 (m, 1H), 3.56 (ddd, J=7.0, 9.5, 14.1 Hz, 2H), 3.42 (ddd, J=7.1, 9.6, 14.1 Hz, 2H), 3.28-3.24 (m, 2H), 1.57-1.53 (m, 4H), 1.11 (dd, J=7.0, 7.0 Hz, 6H).

Step 2. (R)-Quinuclidin-3-yl 2-(((5-((4,4-diethoxy-butyl)carbamoyl)thiophen-2-yl)methyl)amino)-2,3-dihydro-1H-indene-2-carboxylate

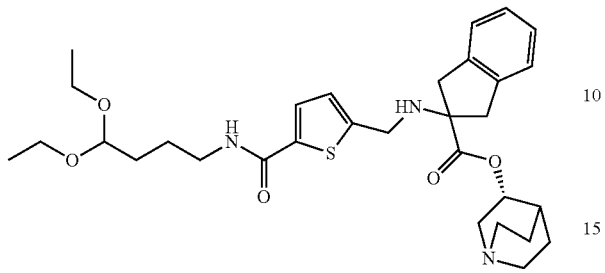

The title compound was prepared as described in Example 1 Step 2 with N-(4,4-diethoxybutyl)-5-formylthiophene-2-carboxamide and (R)-quinuclidin-3-yl 2-amino-2,3-dihydro-1H-indene-2-carboxylate dihydrochloride replacing N-(4,4-diethoxybutyl)-3-formylbenzamide and (R)-quinuclidin-3-yl 1-amino-2,3-dihydro-1H-indene-1-carboxylate dihydrochloride respectively.

$^1$H NMR (400 MHz, DMSO-$d_6$); δ 8.34-8.28 (m, 1H), 7.52 (dd, J=3.6, 3.6 Hz, 1H), 7.22-7.12 (m, 4H), 6.91 (d, J=3.8 Hz, 1H), 4.74-4.68 (m, 1H), 4.47 (dd, J=5.1, 5.1 Hz, 1H), 4.16-4.09 (m, 1H), 3.91-3.83 (m, 2H), 3.54 (ddd, J=7.0, 9.5, 14.1 Hz, 2H), 3.45-3.38 (m, 2H), 3.27-3.00 (m, 7H), 2.69-2.59 (m, 3H), 1.92-1.88 (m, 1H), 1.64-1.57 (m, 3H), 1.52-1.48 (m, 5H), 1.33-1.19 (m, 2H) 1.10 (dd, J=7.0, 7.0 Hz, 6H).

Step 3. (R)-Quinuclidin-3-yl 2-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-2-carboxylate (Compound 14)

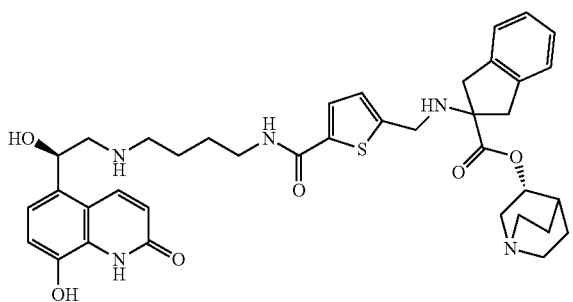 [SMILES: O=C(NCCCCNC[C@H](O)c1ccc(O)c2[nH]c(=O)ccc12)c1ccc(CNC2(C(=O)O[C@H]3CN4CCC3CC4)Cc3ccccc3C2)s1]

The title compound was prepared as described in Example 1 with (R)-quinuclidin-3-yl 2-(((5-((4,4-diethoxybutyl)carbamoyl)thiophen-2-yl)methyl)amino)-2,3-dihydro-1H-indene-2-carboxylate replacing (R)-quinuclidin-3-yl 1-((3-((4,4-diethoxy-butyl)carbamoyl)benzyl)amino)-2,3-dihydro-1H-indene-1-carboxylate in Step 3.

$^1$H NMR (400 MHz, MeOD); δ 8.38 (d, J=9.3 Hz, 1H), 7.66 (d, J=3.1 Hz, 1H), 7.34-7.29 (m, 6H), 7.05 (d, J=8.2 Hz, 1H), 6.63 (d, J=9.5 Hz, 1H), 5.41 (t, J=7.8 Hz, 1H), 5.33 (s, 1H), 4.61 (s, 2H), 3.87-3.70 (m, 3H), 3.64 (d, J=16.6 Hz, 2H), 3.43 (dd, J=6.3, 6.3 Hz, 2H), 3.29-3.21 (m, 6H), 3.16 (dd, J=7.3, 7.3 Hz, 2H), 2.83-2.74 (m, 1H), 2.32 (s, 11-1), 2.07-1.88 (m, 2H), 1.82-1.81 (m, 2H), 1.77-1.65 (m, 3H), 1.46 (t, J=13.0 Hz, 1H).

Example 15. (1-(3-Hydroxybenzyl)piperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate (Compound 15)

Step 1. Benzyl 4-(((1-((tert-butoxycarbonyl)amino)-2,3-dihydro-1H-indene-1-carbonyl)oxy)methyl)piperidine-1-carboxylate

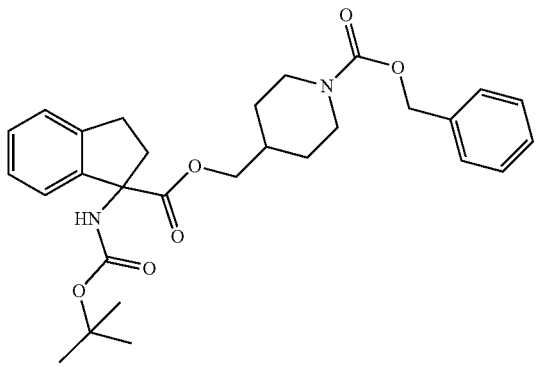 [SMILES: CC(C)(C)OC(=O)NC1(C(=O)OCC2CCN(C(=O)OCc3ccccc3)CC2)CCc2ccccc21]

To a solution of 1-((tert-butoxycarbonyl)amino)-2,3-dihydro-1H-indene-1-carboxylic acid (6.35 g, 22.9 mmol) in DMF (20 mL) was added potassium carbonate (3.8 g, 27.5 mmol) and benzyl 4-((tosyloxy)methyl)piperidine-1-carboxylate (9.75 g, 24.07 mmol). The reaction mixture was stirred at 80° C. for 16 hours. The reaction mixture was diluted with ethyl acetate and washed with water and brine (×2). The organic phase was dried over anhydrous magnesium sulfate, filtered and the filtrate concentrated at reduced pressure to afford the title compound (12.0 g, 100%)

$^1$H NMR (400 MHz, DMSO) d 7.71 (s, 1H), 7.42-7.32 (m, 6H), 7.25-7.23 (m, 2H), 7.22-7.17 (m, 1H), 5.07 (s, 2H), 3.99 (d, J=12.5 Hz, 2H), 3.95-3.81 (m, 2H), 2.94 (dd, J=7.9, 14.3 Hz, 2H), 2.86-2.68 (m, 3H), 2.19-2.10 (m, 1H), 1.80-1.73 (m, 1H), 1.62-1.56 (m, 2H), 1.38 (s, 9H), 1.15-1.04 (m, 2H).

Step 2. Piperidin-4-ylmethyl 1-((tert-butoxycarbonyl)amino)-2,3-dihydro-1H-indene-1-carboxylate

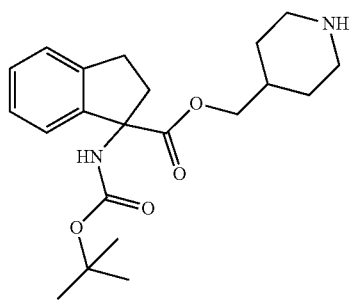 [SMILES: CC(C)(C)OC(=O)NC1(C(=O)OCC2CCNCC2)CCc2ccccc21]

To a stirred solution of benzyl 4-(((1-((tert-butoxycarbonyl)amino)-2,3-dihydro-1H-indene-1-carbonyl)oxy)methyl)piperidine-1-carboxylate (1.2 g, 2.36 mmol) in ethanol (30 mL) was added palladium on charcoal (10%, 1.7 g) and 1-methyl-1,4-cyclohexadiene (1.4 mL, 11.8 mmol). The mixture was heated to reflux and stirred at this temperature for 40 minutes. The suspension was filtered, the filter cake washed with ethanol and the filtrate evaporated at reduced pressure to afford the title material (0.78 g, 88%).

$^1$H NMR (400 MHz, CDCl$_3$); δ 7.32 (d, J=7.5 Hz, 2H), 7.23-7.17 (m, 2H), 5.39 (s, 1H), 3.99-3.90 (m, 2H), 3.13-3.01 (m, 8H), 2.60-2.50 (m, 4H), 2.45-2.34 (m, 3H), 1.76-1.66 (m, 2H), 1.20-1.04 (m, 6H).

Step 3. (1-(3-Hydroxybenzyl)piperidin-4-yl)methyl 1-amino-2,3-dihydro-1H-indene-1-carboxylate dihydrochloride

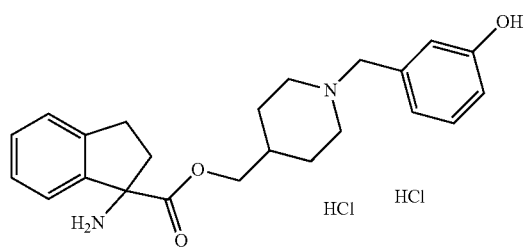 [SMILES: NC1(C(=O)OCC2CCN(Cc3cccc(O)c3)CC2)CCc2ccccc21 ; Cl ; Cl]

To a solution of piperidin-4-ylmethyl 1-((tert-butoxycarbonyl)amino)-2,3-dihydro-1H-indene-1-carboxylate (0.25 g, 0.67 mmol) in DCM (4 mL) was added acetic acid (catalytic) and 3-hydroxybenzaldehyde (0.10 g, 0.8 mmol) and the mixture stirred for 1 hour. Sodium triacetoxyborohydride (0.285 g, 1.4 mmol) added and the reaction mixture stirred at room temperature for 18 hours. Water and DCM added and the mixture poured through a hydrophobic fit. The solvent evaporated at reduced pressure and the resulting residue treated with a solution of HCl in dioxane (4M, 4 mL). The reaction stirred at room temperature for 18 hours. The solvent evaporated at reduced pressure to afford the title compound.

$^1$H NMR (400 MHz, DMSO-d$_6$); δ 9.31 (s, 1H), 9.27 (s, 3H), 7.56 (d, J=7.5 Hz, 1H), 7.41-7.39 (m, 2H), 7.39-7.30 (m, 1H), 7.23 (dd, J=7.8, 7.8 Hz, 1H), 7.05-6.99 (m, 1H), 6.98 (s, 1H), 6.86 (dd, J=1.8, 8.1 Hz, 1H), 4.23-3.95 (m, 4H), 3.32-2.99 (m, 5H), 2.88-2.73 (m, 2H), 2.41-2.32 (m, 1H), 1.89-1.82 (m, 1H), 1.75-1.67 (m, 4H).

Step 4. (1-(3-Hydroxybenzyl)piperidin-4-yl)methyl 1-(((5-((4-(((R)-2-hydroxy-2-(8-hydroxy-2-oxo-1,2-dihydroquinolin-5-yl)ethyl)amino)butyl)carbamoyl) thiophen-2-yl)methyl)amino)-2,3-dihydro-1H-indene-1-carboxylate (Compound 15)

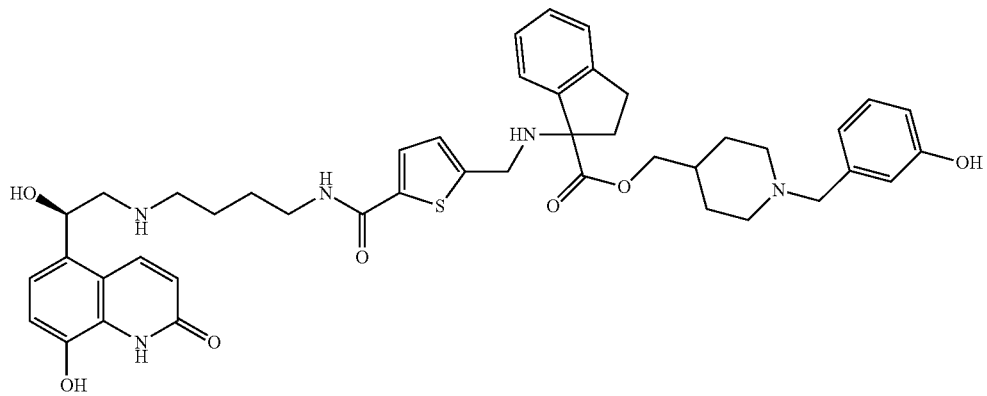 [SMILES: O=C(NCCCCNC[C@H](O)c1ccc(O)c2[nH]c(=O)ccc12)c1ccc(CNC2(C(=O)OCC3CCN(Cc4cccc(O)c4)CC3)CCc3ccccc32)s1]

The title compound was prepared as described in Example 14 with (1-(3-hydroxybenzyl)piperidin-4-yl)methyl 1-amino-2,3-dihydro-1H-indene-1-carboxylate dihydrochloride replacing (R)-quinuclidin-3-yl 2-amino-2,3-dihydro-1H-indene-2-carboxylate dihydrochloride in Step 2 and the product used in subsequent steps.

$^1$H NMR (400 MHz, DMSO-d$_6$); δ 10.52 (s, 1H), 10.47 (s, 1H), 9.54-9.54 (m, 1H), 8.51-8.51 (m, 2H), 8.18 (d, J=9.9 Hz, 1H), 7.60 (d, J=8.2 Hz, 2H), 7.45 (dd, J=7.5, 7.5 Hz, 2H), 7.38 (d, J=5.4 Hz, 5H), 7.30 (dd, J=3.1, 5.3 Hz, 1H), 7.15 (d, J=8.3 Hz, 1H), 7.09 (s, 1H), 7.03 (d, J=1.4 Hz, 1H), 6.98 (d, J=8.2 Hz, 1H), 6.80 (s, 1H), 6.59 (dd, J=2.2, 9.9 Hz, 1H), 6.16 (d, J=3.3 Hz, 1H), 5.32-5.29 (m, 1H), 5.01-4.99 (m, 1H), 4.13 (s, 1H), 4.02 (dd, J=6.3, 6.3 Hz, 2H), 3.89-3.72 (m, 3H), 3.60 (dd, J=8.9, 14.1 Hz, 1H), 3.14-2.95 (m, 9H), 2.49-2.38 (m, 3H), 2.12 (d, J=20.1 Hz, 1H), 1.86-1.67 (m, 9H), 1.59 (s, 2H), 1.47 (dd, J=7.2, 14.9 Hz, 2H).

In a similar fashion were prepared using the appropriate aldehyde in Step 3 above:

(1-Benzylpiperidin-4-yl)methyl 1-(((5-((4-(((R)-2-hydroxy-2-(8-hydroxy-2-oxo-1,2-dihydroquinolin-5-yl)ethyl) amino)butyl)carbamoyl)thiophen-2-yl)methyl)amino)-2,3-dihydro-1H-indene-1-carboxylate (Compound 16) using benzaldehyde.

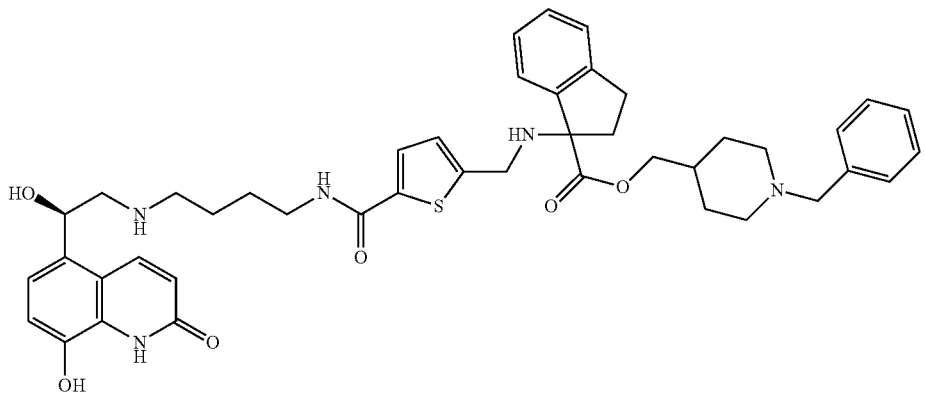 [SMILES: O=C(NCCCCNC[C@H](O)c1ccc(O)c2[nH]c(=O)ccc12)c1ccc(CNC2(C(=O)OCC3CCN(Cc4ccccc4)CC3)CCc3ccccc32)s1]

¹H NMR (400 MHz, MeOD); δ 8.50 (s, 2H), 8.37 (d, J=9.8 Hz, 1H), 7.50 (d, J=3.8 Hz, 1H), 7.43 (s, 5H), 7.37 (d, J=7.5 Hz, 1H), 7.32-7.28 (m, 3H), 7.27-7.20 (m, 1H), 7.04 (d, J=8.2 Hz, 1H), 6.96 (d, J=3.8 Hz, 1H), 6.68 (d, J=9.9 Hz, 1H), 5.41 (t, J=6.0 Hz, 1H), 4.03-3.95 (m, 4H), 3.88 (s, 2H), 3.42 (t, J=7.9 Hz, 2H), 3.26-3.08 (m, 8H), 2.77-2.67 (m, 1H), 2.61-2.59 (m, 2H), 2.31-2.22 (m, 1H), 1.84-1.68 (m, 7H), 1.47-1.35 (m, 2H).

(1-(Thiophen-2-ylmethyl)piperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate (Compound 17) using thiophene-2-carboxaldehyde.

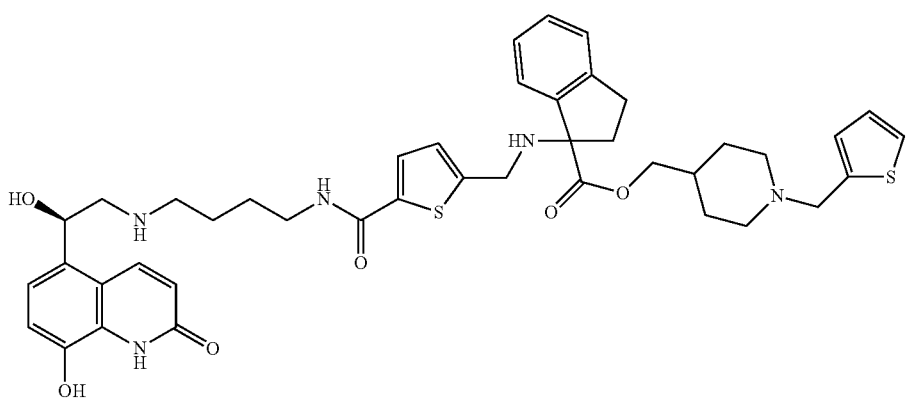 [SMILES: O=C(NCCCCNC[C@H](O)c1ccc(O)c2[nH]c(=O)ccc12)c1ccc(CNC2(C(=O)OCC3CCN(Cc4cccs4)CC3)CCc3ccccc32)s1]

1H NMR (400 MHz, MeOD); δ 8.37 (dd, J=2.4, 9.9 Hz, 1H), 7.66-7.61 (m, 2H), 7.57 (d, J=7.5 Hz, 1H), 7.49 (d, J=6.1 Hz, 2H), 7.41-7.35 (m, 1H), 7.32-7.26 (m, 3H), 7.16 (dd, J=3.6, 5.0 Hz, 1H), 7.05 (d, J=8.2 Hz, 1H), 6.66 (d, J=9.3 Hz, 1H), 5.42 (t, J=6.2 Hz, 1H), 4.56-4.39 (m, 4H), 4.16 (d, J=5.8 Hz, 2H), 3.55-3.48 (m, J=9.3 Hz, 2H), 3.43 (t, J=4.6 Hz, 2H), 3.40-3.30 (m, 2H), 3.28-3.20 (m, 2H), 3.16 (t, J=4.6 Hz, 2H), 3.06-2.94 (m, 3H), 2.70-2.62 (m, 1H), 2.04-1.94 (m, 1H), 1.85-1.69 (m, 6H), 1.47 (s, 2H).

Example 16. (R)-Quinuclidin-3-yl 1-(2-(4-(2-((4-((((R)-2-hydroxy-2-(8-hydroxy-2-oxo-1,2-dihydroquinolin-5-yl)ethyl)amino)methyl)phenyl)amino)-2-oxoethyl)phenyl)acetamido)-2,3-dihydro-1H-indene-1-carboxylate (Compound 18)

Step 1. (R)-5-(2-amino-1-((tert-butyldimethylsilyl)oxy)ethyl)-8-(benzyloxy)quinolin-2(1H)-one

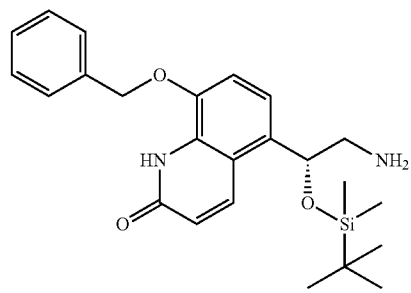 [SMILES: CC(C)(C)[Si](C)(C)O[C@@H](CN)c1ccc(OCc2ccccc2)c2[nH]c(=O)ccc12]

To a solution of (R)-5-(2-azido-1-((tert-butyldimethylsilyl)oxy)ethyl)-8-(benzyloxy)quinolin-2(1H)-one (9.4 g, 21.0 mmol) in THF/water (80 mL/4 mL) was added triphenylphosphine (6.03 g, 23.0 mmol). The reaction mixture was heated at reflux 18 hours. The solvent was evaporated and residue was purified by flash column chromatography (eluent—100% DCM to 25:1 DCM/methanol) to afford the title compound (8.30 g, 93%).

¹H NMR (400 MHz, CDCl₃); δ 9.19-9.17 (m, 1H), 8.23 (d, J=9.9 Hz, 1H), 7.44-7.42 (m, 5H), 7.14 (d, J=8.3 Hz, 1H), 7.01 (d, J=8.2 Hz, 1H), 6.67 (d, J=9.9 Hz, 1H), 5.17 (s, 2H), 4.98 (dd, J=4.4, 7.2 Hz, 1H), 2.99-2.85 (m, 2H), 1.36-1.35 (m, 2H), 0.90 (s, 9H), 0.08 (s, 3H), −0.14 (s, 3H).

Step 2; (R)-tert-butyl (2-(8-(benzyloxy)-2-oxo-1,2-dihydroquinolin-5-yl)-2-((tert-butyldimethylsilyl)oxy)ethyl)(4-nitrobenzyl)carbamate

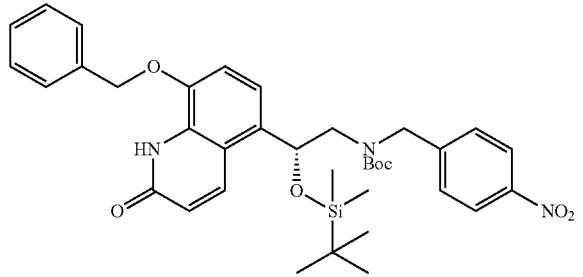 [SMILES: CC(C)(C)OC(=O)N(Cc1ccc([N+](=O)[O-])cc1)C[C@H](O[Si](C)(C)C(C)(C)C)c1ccc(OCc2ccccc2)c2[nH]c(=O)ccc12]

To a solution of (R)-5-(2-amino-1-((tert-butyldimethylsilyl)oxy)ethyl)-8-(benzyloxy)quinolin-2(1H)-one (1.0 g, 2.35 mmol) and 4-nitrobenzaldehyde (0.390 g, 2.58 mmol) in DCM (15 mL) was added magnesium sulfate. The mixture was stirred at room temperature for 72 hours. The suspension was filtered through a plug of celite and the filter cake washed with further DCM. The filtrate was concentrated under reduced pressure. The residue was dissolved in methanol and sodium borohydride (0.178 g, 4.7 mmol) added. The reaction mixture stirred at room temperature for 4 hours. The reaction mixture was partitioned between ethyl acetate and 10% aqueous potassium carbonate. The organic phase was dried over magnesium sulfate, filtered and the filtrate evaporated at reduced. The residue was dissolved in DCM (8 mL) and a solution of di-tert-butyl dicarbonate (0.615 g, 2.82 mmol) in DCM (2 mL) was added. The reaction mixture stirred at room temperature for 18 hours. The solvent was evaporated at reduced pressure and the residue purified by flash column chromatography (eluent; 100% iso-hexane to 2:1 iso-hexane/ethyl acetate) to afford the title compound (1.09 g, 70%).

¹H NMR (400 MHz, CDCl₃); δ 9.18 (s, 1H), 8.43-8.39 and 8.25-8.21 (m, 1H), 8.17-8.12 (m, 2H), 7.56-7.51 (m, 1H), 7.44-7.37 (m, 4H), 7.29-7.23 (m, 1H), 7.05-6.99 (m, 1H), 6.77-6.62 (m, 1H), 5.56 and 5.34 (br s, 1H), 5.20-5.13 (m, 2H), 4.85-4.67 (m, 2H), 4.48-4.36 (m, 1H), 3.65-3.41 (m, 1H), 1.51 and 1.44 (s, 9H), 0.94 and 0.91 (s, 9H), 0.10 (s, 3H), −0.12 (s, 3H).

Step 3; (R)-tert-butyl 4-aminobenzyl(2-((tert-butyldimethylsilyl)oxy)-2-(8-hydroxy-2-oxo-1,2-dihydroquinolin-5-yl)ethyl)carbamate

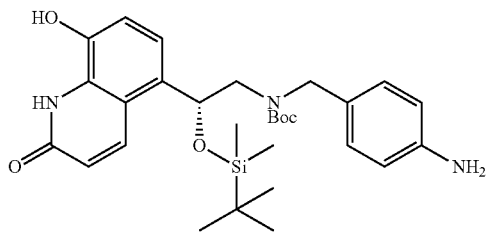 [SMILES: CC(C)(C)OC(=O)N(Cc1ccc(N)cc1)C[C@H](O[Si](C)(C)C(C)(C)C)c1ccc(O)c2[nH]c(=O)ccc12]

To a stirred solution of (R)-tert-butyl (2-(8-(benzyloxy)-2-oxo-1,2-dihydroquinolin-5-yl)-2-((tert-butyldimethylsilyl)oxy)ethyl)(4-nitrobenzyl)carbamate (1.09 g, 1.65 mmol) in ethanol (10 mL) was added palladium on charcoal (10%, 1.0 g) and 1-methyl-1,4-cyclohexadiene (1.85 mL, 16.5 mmol). The reaction mixture was heated to reflux [Care—evolution of gas] and heated at reflux for 1 hour. The suspension was filtered and the filtrate evaporated at reduced pressure to afford the title compound (0.685 g, 77%).

¹H NMR (400 MHz, MeOD); δ 8.42 (br s, 1H), 7.13 (brs, 1H), 6.91-6.73 (m, 3H), 6.62-6.49 (m, 3H), 5.36 (brs, 1H), 4.34-4.08 (m, 2H); 3.34-3.11 (m, 2H), 1.37 and 1.30 (s, 9H), 0.84-0.76 (m, 9H), −0.01 (s, 3H), −0.22 (s, 3H).

Step 4. (R)-2-(4-(2-((4-(((tert-butoxycarbonyl)(2-((tert-butyldimethylsilyl)oxy)-2-(8-hydroxy-2-oxo-1,2-dihydroquinolin-5-yl)ethyl)amino)methyl)phenyl)amino)-2-oxoethyl)phenyl)acetic acid

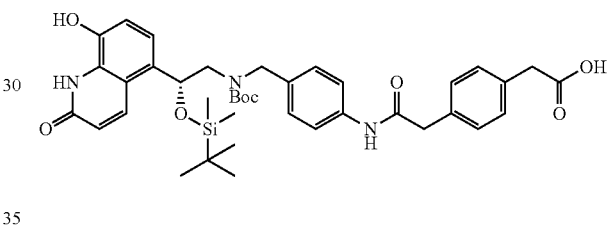

To a solution of 2-(4-(2-ethoxy-2-oxoethyl)phenyl)acetic acid (0.311 g, 1.40 mmol) in DMF (20 mL) was added DIPEA (0.264 mL, 1.51 mmol) and HATU (0.577 g, 1.51 mmol) and the reaction mixture was stirred at room temperature for 30 minutes. A solution of (R)-tert-butyl 4-aminobenzyl(2-((tert-butyldimethylsilyl)oxy)-2-(8-hydroxy-2-oxo-1,2-dihydroquinolin-5-yl)ethyl)carbamate (0.63 g, 1.16 mmol) in DMF (5 mL) was added and the reaction mixture stirred at room temperature for 24 hours. Additional HATU (0.20 g, 5.26 mmol) and DIPEA (0.264 mL, 1.51 mmol) added and the reaction mixture stirred at 40° C. for 2 hours. The reaction mixture was diluted with ethyl acetate and washed with 0.1M aqueous sodium hydroxide (×2), water and brine. The organic phase was dried over anhydrous magnesium sulfate, filtered and the solvent evaporated at reduced pressure. The residue was purified by column chromatography (eluent; 100% iso-hexane to 100% ethyl acetate) to isolate the major product. The residue was dissolved in THF (5 mL) and 2M aqueous sodium hydroxide (5 mL) added. The reaction mixture was stirred at room temperature for 5 hours. The solvent was evaporated at reduced pressure and the residue partitioned between ethyl acetate and water. pH adjusted to 4 and the mixture separated. The aqueous phase extracted with further ethyl acetate (×2) and the combined organic phase dried over magnesium sulfate, filtered and the solvent evaporated at reduced pressure to afford the title compound (0.758 g, 76%).

Step 5. (R)-Quinuclidin-3-yl 1-(2-(4-(2-((4-((((R)-2-hydroxy-2-(8-hydroxy-2-oxo-1,2-dihydroquinolin-5-yl)ethyl)amino)methyl)phenyl)amino)-2-oxoethyl)phenyl)acetamido)-2,3-dihydro-1H-indene-1-carboxylate (Compound 18)

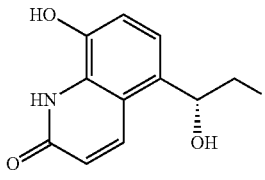

To a stirred solution of (R)-2-(4-(2-((4-(((tert-butoxycarbonyl)(2-((tert-butyldimethylsilyl)oxy)-2-(8-hydroxy-2-oxo-1,2-dihydroquinolin-5-yl)ethyl)amino)methyl)phenyl)amino)-2-oxoethyl)phenyl)acetic acid (0.370 g, 0.516 mmol) in DMF (5 mL) was added EDC (0.159 g, 0.82 mmol), DIPEA (0.269 mL, 1.55 mmol) and HOPO (0.091 g, 0.82 mmol) and the mixture was stirred at room temperature for 1 hour. A solution of (R)-quinuclidin-3-yl 1-amino-2,3-dihydro-1H-indene-1-carboxylate dihydrochloride (0.162 g, 0.568 mmol) in DMF (1 mL). The reaction mixture was stirred at room temperature for 18 hours. The reaction mixture was diluted with water and extracted with ethyl acetate (×3). The combined organic extracts were washed with water, brine and dried over magnesium sulfate. The suspension was filtered and the solvent evaporated at reduced pressure. The residue was treated with a solution of HCl in dioxane (4M, 0.5 mL) and the mixture stirred at room temperature for 2 hours. The solvent was evaporated at reduced pressure, the residue dissolved in DMSO and the mixture purified by reverse phase preparative HPLC to afford the title compound.

$^{1}$H NMR (400 MHz, DMSO-$d_6$, 90° C.); δ 10.05-9.80 (m, 2H), 8.78 (s, 1H), 6.54 (d, J=9.9 Hz, 1H), 8.09 (d, J=8.7 Hz, 2H), 7.48-7.43 (m, 3H), 7.33-7.25 (m, 6H), 7.12 (d, J=8.3 Hz, 1H), 6.99 (d, J=8.2 Hz, 1H), 6.54 (d, J=9.9 Hz, 1H), 5.33 (dd, J=4.9, 8.2 Hz, 1H), 4.87-4.84 (m, 1H), 4.19 (d, J=2.4 Hz, 2H), 3.65 (s, 2H), 3.60-3.44 (m, 4H), 3.22-2.86 (m, 8H), 2.71-2.64 (m, 1H), 2.17-2.10 (m, 2H), 1.83-1.68 (m, 3H), 1.62-1.56 (m, 1H).

Example 17. (R)-Quinuclidin-3-yl 1-(4-((4-((((R)-2-hydroxy-2-(8-hydroxy-2-oxo-1,2-dihydroquinolin-5-yl)ethyl)amino)methyl)benzyl)oxy)benzamido)-2,3-dihydro-1H-indene-1-carboxylate (Compound 19)

Step 1. Methyl 4-((4-formylbenzyl)oxy)benzoate

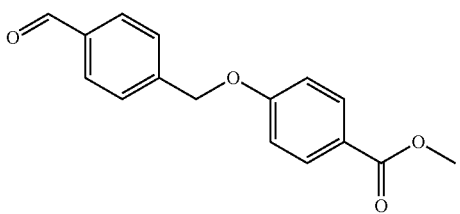 [SMILES: COC(=O)c1ccc(OCc2ccc(C=O)cc2)cc1]

Potassium carbonate (1.66 g, 12 mmol) was added to a solution of methyl 4-hydroxybenzoate (1.67 g, 11 mmol) in DMF (25 mL). After 10 minutes 4-(bromomethyl)benzaldehyde (1.99 g, 10.0 mmol) was added and the mixture stirred at room temperature for 17 hours. The reaction mixture was diluted with ethyl acetate and washed with water, 10% aqueous potassium carbonate and brine (×3). The organic phase was dried over anhydrous magnesium sulfate, the suspension filtered and the filtrate was concentrated at reduced pressure to afford the title compound (2.40 g, 89%).

$^{1}$H NMR (400 MHz, CDCl$_3$); δ 10.03 (s, 1H), 8.03-7.99 (m, 2H), 7.93-7.91 (m, 2H), 7.61 (d, J=8.0 Hz, 2H), 7.01-6.98 (m, 2H), 5.21 (s, 2H), 3.89 (s, 3H).

Step 2. 4-((4-Formylbenzyl)oxy)benzoic acid

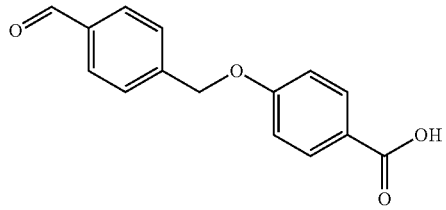 [SMILES: O=Cc1ccc(COc2ccc(C(=O)O)cc2)cc1]

To a stirred solution of methyl 4-((4-formylbenzyl)oxy)benzoate (1.77 g, 6.55 mmol) in methanol/THF (33 mL/33 mL) was added 2M aqueous sodium hydroxide (33 mL). The reaction mixture was stirred at room temperature for 3 hours. The reaction mixture was concentrated at reduced pressure and 2M aqueous hydrochloric acid and ethyl acetate added. The resultant suspension was filtered and the solid dried in vacuo to afford the title compound (1.20 g, 72%).

$^{1}$H NMR (400 MHz, DMSO-$d_6$); δ 10.02 (s, 1H), 7.94 (d, J=8.3 Hz, 2H), 7.79 (d, J=8.8 Hz, 2H), 7.68 (d, J=8.0 Hz, 2H), 6.89 (d, J=8.9 Hz, 2H), 5.23 (s, 2H).

Step 3. (R)-Quinuclidin-3-yl 1-(4-((4-formylbenzyl)oxy)benzamido)-2,3-dihydro-1H-indene-1-carboxylate

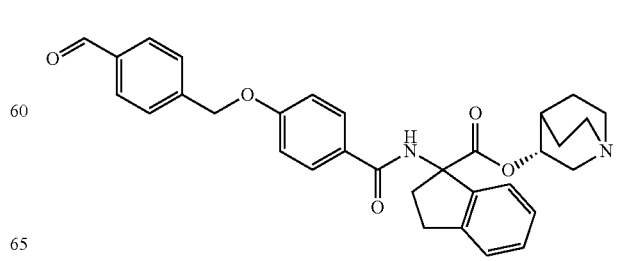

The title compound was prepared as described in Example 2 Step 3 with 4-((4-formylbenzyl)oxy)benzoic acid replacing 3-(4-(1,3-dioxolan-2-yl)butoxy)benzoic acid.

$^1$H NMR (400 MHz, DMSO-d$_6$); δ 10.04-10.02 (m, 1H), 9.04-9.02 (m, 1H), 7.97-7.05 (m, 12H), 5.31 (s, 2H), 4.75-4.67 (m, 1H), 3.20-2.92 (m, 7H), 2.34-2.18 (m, 1H), 2.00-1.85 (m, 2H), 1.65-1.54 (m, 3H), 1.37-1.21 (m, 1H), 1.20-1.05 (m, 1H).

Step 4. (R)-Quinuclidin-3-yl 1-(4-((4-((((R)-2-hydroxy-2-(8-hydroxy-2-oxo-1,2-dihydroquinolin-5-yl)ethyl)amino)methyl)benzyl)oxy)benzamido)-2,3-dihydro-1H-indene-1-carboxylate (Compound 19)

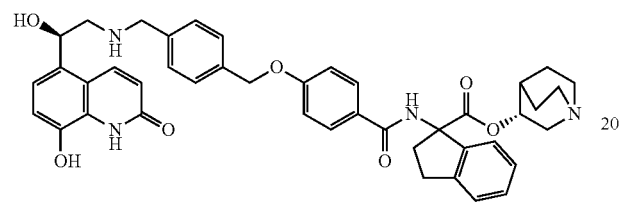

(R)-Quinuclidin-3-yl 1-(4-((4-formylbenzyl)oxy)benzamido)-2,3-dihydro-1H-indene-1-carboxylate (0.30 g, 0.57 mmol) was dissolved in ethanol (2 mL) and added to a pre-stirred (10 minutes) mixture of (R)-5-(2-amino-1-hydroxyethyl)-8-hydroxyquinolin-2(1H)-one hydrochloride (0.175 g, 0.68 mmol) and triethylamine (0.15 mL, 1.14 mmol) in ethanol (4 mL). The reaction mixture was stirred at room temperature for one hour. Sodium triacetoxyborohydride (0.245 g, 1.14 mmol) and acetic acid (0.07 mL, 1.0 mmol) were added and the reaction mixture stirred at room temperature for 18 hours. The reaction mixture was concentrated at reduced pressure and the residue partitioned between water and iso-butanol. The aqueous phase was extracted with additional iso-butanol and the combined organic extracts evaporated at reduced pressure. The residue was purified by reverse phase preparative HPLC to afford the title compound.

$^1$H NMR (400 MHz, MeOD); δ 8.24 (dd, J=2.6, 9.9 Hz, 1H), 7.88 (dd, J=9.2, 9.2 Hz, 2H), 7.62-7.56 (m, 5H), 7.38-7.27 (m, 4H), 7.12-7.08 (m, 2H), 7.04 (d, J=8.2 Hz, 1H), 6.65 (d, J=9.9 Hz, 1H), 5.41 (dd, J=6.7, 6.7 Hz, 1H), 5.22 (s, 2H), 5.13-5.03 (m, 1H), 4.35 (s, 2H), 3.77-3.68 (m, 1H), 3.44 (d, J=11.4 Hz, 1H), 3.30-3.22 (m, 6H), 3.16-3.10 (m, 3H), 2.41-2.26 (m, 2H), 2.08-1.80 (m, 4H).

Example 18. (R)-Quinuclidin-3-yl 1-((3-((4-((((R)-2-hydroxy-2-(8-hydroxy-2-oxo-1,2-dihydroquinolin-5-yl)ethyl)amino)methyl)benzyl)oxy)benzyl)amino)-2,3-dihydro-1H-indene-1-carboxylate (Compound 20)

Step 1. 2-(4-(Bromomethyl)phenyl)-1,3-dioxolane

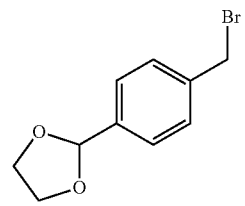 [SMILES: BrCc1ccc(C2OCCO2)cc1]

To a solution of 4-bromomethylbenzaldehyde (1.0 g, 5.03 mmol) in toluene (30 mL) was added pTSA (0.095 g, 0.5 mmol) and ethylene glycol (0.783 g, 2.56 mmol) and the mixture heated at 140° C. under Dean and Stark conditions. The reaction mixture was diluted with DCM and washed with saturated aqueous sodium carbonate. The organic phase was passed through a hydrophobic frit and the solvent evaporated at reduced pressure to afford the title compound (1.52 g, >100%).

$^1$H NMR (400 MHz, CDCl$_3$); δ 7.50-7.41 (m, 4H), 5.74 (s, 1H), 4.73 (s, 2H), 4.06-3.93 (m, 2H).

Step 2. 3-((4-(1,3-Dioxolan-2-yl)benzyl)oxy)benzaldehyde

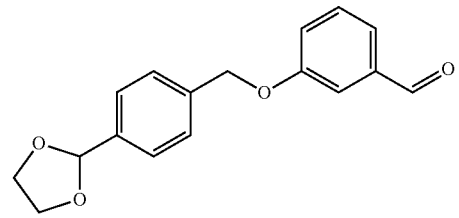 [SMILES: O=Cc1cccc(OCc2ccc(C3OCCO3)cc2)c1]

To a stirred solution of 3-hydroxybenzaldehyde (0.30 g, 2.46 mmol) in DMF (6 mL) was added potassium carbonate (0.60 g 3.7 mmol) and the mixture stirred at room temperature for 10 minutes. 2-(4-(Bromomethyl)phenyl)-1,3-dioxolane (0.30 g, 0.60 g, 2.5 mmol) was added and the reaction mixture was heated at 60° C. for 18 hours. The reaction mixture was diluted with water and extracted with DCM (×3). The combined organics were passed through a hydrophobic phase separator and the filtrate evaporated under reduced pressure. The residue was purified by flash column chromatography (eluent; 100% iso-hexane to 20% ethyl acetate/iso-hexane) to afford the title compound (0.42 g, 61%).

$^1$H NMR (400 MHz, DMSO-d$_6$); δ 9.98 (s, 1H), 7.55-7.47 (m, 6H), 7.46-7.45 (m, 1H), 7.39-7.35 (m, 1H), 5.74 (s, 1H), 5.23 (s, 2H), 4.08-3.93 (m, 4H).

Step 3. (R)-Quinuclidin-3-yl 1-((3-((4-((((R)-2-hydroxy-2-(8-hydroxy-2-oxo-1,2-dihydroquinolin-5-yl)ethyl)amino)methyl)benzyl)oxy)benzyl)amino)-2,3-dihydro-1H-indene-1-carboxylate (Compound 20)

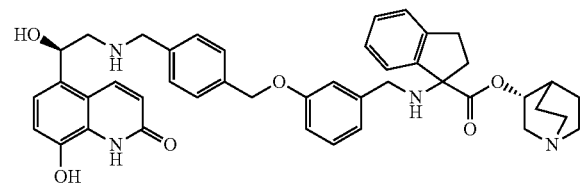 [SMILES: O=C(O[C@H]1CN2CCC1CC2)C1(NCc2cccc(OCc3ccc(CNC[C@H](O)c4ccc(O)c5[nH]c(=O)ccc45)cc3)c2)CCc2ccccc21]

The title compound was prepared as described in Example 1 with 3-((4-(1,3-dioxolan-2-yl)benzyl)oxy)benzaldehyde replacing N-(4,4-diethoxybutyl)-3-formylbenzamide in Step 2 and the product used in subsequent steps.

$^1$H NMR (400 MHz, MeOD); δ 8.45 (s, 2H), 8.23 (dd, J=3.1, 9.9 Hz, 1H), 7.59-7.51 (m, 4H), 7.45 (dd, J=7.3, 15.4 Hz, 1H), 7.35-7.22 (m, 5H), 7.06-7.02 (m, 2H), 6.98-6.90 (m, 2H), 6.65 (d, J=9.8 Hz, 1H), 5.39 (dd, J=6.7, 6.7 Hz,

1H), 5.15 (s, 2H), 5.08-5.01 (m, 1H), 4.29 (s, 2H), 3.69 (d, J=3.5 Hz, 2H), 3.67-3.49 (m, 1H), 3.22-3.21 (m, 1H), 3.21-3.12 (m, 7H), 2.94-2.77 (m, 2H), 2.40-2.24 (m, 3H), 2.03-1.68 (m, 3H), 1.66-1.61 (m, 1H).

Example 19. (R)-Quinuclidin-3-yl 1-((3-((3-(4-(((R)-2-hydroxy-2-(8-hydroxy-2-oxo-1,2-dihydroquinolin-5-yl)ethyl)amino)butoxy)benzyl)oxy)benzyl)amino)-2,3-dihydro-1H-indene-1-carboxylate (Compound 21)

Step 1. 3-((3-(3-(1,3-Dioxolan-2-yl)propoxy)benzyl)oxy)benzaldehyde

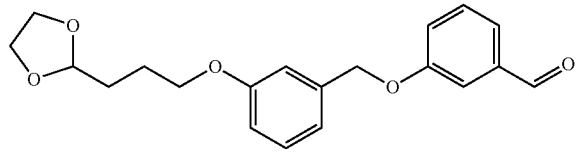 [SMILES: O=Cc1cccc(OCc2cccc(OCCCC3OCCO3)c2)c1]

To a stirred solution of 3-((3-hydroxybenzyl)oxy)benzaldehyde (0.20 g, 0.88 mmol) in DMF (3 mL) was added potassium carbonate (0.24 g, 1.75 mmol) and 2-(3-chloropropyl)-1,3-dioxalane (0.15 mL, 1.14 mmol) and the reaction mixture heated at 80° C. for 3 hours. The reaction mixture was diluted with ethyl acetate and washed with water, dried over magnesium sulfate, filtered and the filtrate evaporated at reduced pressure. The residue was triturated with iso-hexane/10% ethyl acetate to afford the title compound (0.180 g, 60%).

$^1$H NMR (400 MHz, DMSO-$d_6$); δ 9.98 (s, 1H), 7.55-7.50 (m, 3H), 7.40-7.35 (m, 1H), 7.33-7.27 (m, 1H), 7.02 (d, J=7.2 Hz, 2H), 6.89 (dd, J=1.4, 8.1 Hz, 1H), 5.17 (s, 2H), 4.87-4.77 (m, 1H), 4.00 (dd, J=6.3, 6.3 Hz, 2H), 3.92-3.66 (m, 4H), 1.81-1.56 (m, 4H).

Step 2. (R)-Quinuclidin-3-yl 1-((3-((3-(4-(((R)-2-hydroxy-2-(8-hydroxy-2-oxo-1,2-dihydroquinolin-5-yl)ethyl)amino)butoxy)benzyl)oxy)benzyl)amino)-2,3-dihydro-1H-indene-1-carboxylate (Compound 21)

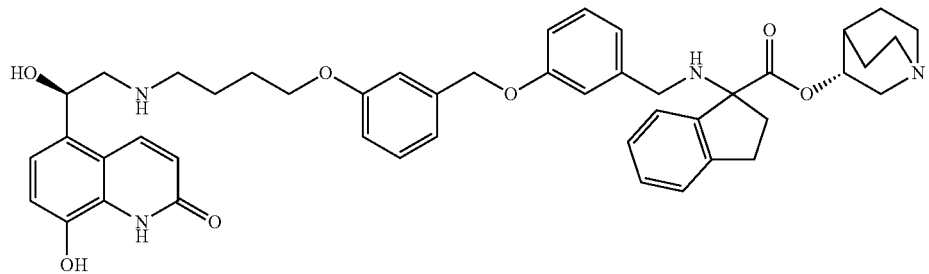 [SMILES: O=C(O[C@H]1CN2CCC1CC2)C1(NCc2cccc(OCc3cccc(OCCCCNC[C@H](O)c4ccc(O)c5[nH]c(=O)ccc45)c3)c2)CCc2ccccc21]

The title compound was prepared as described in Example 1 with 3-((3-(3-(1,3-dioxolan-2-yl)propoxy)benzyl)oxy)benzaldehyde replacing N-(4,4-diethoxybutyl)-3-formylbenzamide in Step 2 and the product used in subsequent steps.

$^1$H NMR (400 MHz, MeOD); δ 8.38 (d, J=9.9 Hz, 1H), 7.64 (dd, J=7.8, 15.8 Hz, 1H), 7.56-7.51 (m, 2H), 7.46-7.37 (m, 2H), 7.32-7.28 (m, 2H), 7.18 (s, 1H), 7.10 (d, J=7.9 Hz, 2H), 7.06-7.02 (m, 3H), 6.92 (dd, J=1.9, 7.3 Hz, 1H), 6.68 (d, J=9.8 Hz, 1H), 5.42 (t, J=6.7 Hz, 1H), 5.36-5.26 (m, 1H), 5.09 (s, 2H), 4.33-4.17 (m, 2H), 4.09 (t, J=4.0 Hz, 2H), 3.81-3.71 (m, 1H), 3.51-3.35 (m, 3H), 3.29-2.96 (m, 8H), 2.87-2.69 (m, 2H), 2.46 (br s, 0.5H), 2.23 (br s, 0.5H), 2.14-1.82 (m, 6H), 1.69-1.60 (m, 1H), 1.34-1.24 (m, 1H).

Example 20. (1-Benzylpiperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate_single stereoisomer 1 (Compound 22)

Step 1. Benzyl 4-(((1-((tert-butoxycarbonyl)amino)-2,3-dihydro-1H-indene-1-carbonyl)oxy)methyl)piperidine-1-carboxylate

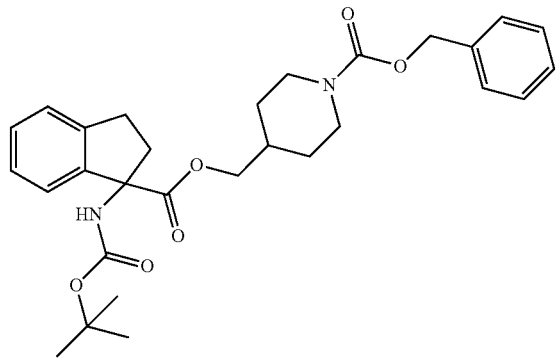 [SMILES: CC(C)(C)OC(=O)NC1(C(=O)OCC2CCN(C(=O)OCc3ccccc3)CC2)CCc2ccccc21]

To a solution of 1-((tert-butoxycarbonyl)amino)-2,3-dihydro-1H-indene-1-carboxylic acid (6.35 g, 22.9 mmol) in DMF (20 mL) was added potassium carbonate (3.8 g, 27.5 mmol) and benzyl 4-((tosyloxy)methyl)piperidine-1-carboxylate (9.75 g, 24.07 mmol). The reaction mixture was stirred at 80° C. for 16 hours. The reaction mixture was diluted with ethyl acetate and washed with water and brine (×2). The organic phase was dried over anhydrous magnesium sulfate, filtered and the filtrate concentrated at reduced pressure to afford the title compound (12.0 g, 100%)

$^1$H NMR (400 MHz, DMSO) d 7.71 (s, 1H), 7.42-7.32 (m, 6H), 7.25-7.23 (m, 2H), 7.22-7.17 (m, 1H), 5.07 (s, 2H), 3.99 (d, J=12.5 Hz, 2H), 3.95-3.81 (m, 2H), 2.94 (dd, J=7.9, 14.3 Hz, 2H), 2.86-2.68 (m, 3H), 2.19-2.10 (m, 1H), 1.80-1.73 (m, 1H), 1.62-1.56 (m, 2H), 1.38 (s, 9H), 1.15-1.04 (m, 2H).

Step 2. Separation of Enantiomers

The material was purified by SFC chromatography (Column—LUX Cellulose-4; Eluent 20% to 80% gradient of iso-propanol with 0.1% diethylamine/carbon dioxide at 120 bar pressure, column temperature 40° C. with a flow rate of 5.0 mL/min) to afford;
Isomer 1: Retention Time 4.53 min; Enantiomeric Excess 100%.
$^1$H NMR (400 MHz, DMSO-$d_6$); δ 7.71 (s, 1H), 7.42-7.32 (m, 6H), 7.25-7.23 (m, 2H), 7.22-7.15 (m, 1H) 5.07 (s, 2H), 4.00-3.81 (m, 4H), 2.98-2.86 (m, 3H), 2.81-2.78 (m, 2H), 2.21-2.11 (m, 1H), 1.75 (brs, 1H), 1.62-1.57 (m, 2H), 1.38 (s, 9H), 1.14-1.02 (m, 2H).
Isomer 2: Retention Time 5.78 min; Enantiomeric Excess 100%.
$^1$H NMR (400 MHz, DMSO-$d_6$); δ 7.71 (s, 1H), 7.42-7.32 (m, 6H), 7.25-7.23 (m, 2H), 7.22-7.17 (m, 1H), 5.07 (s, 2H), 4.00-3.82 (m, 4H), 2.98-2.87 (m, 3H), 2.80-2.79 (m, 2H), 2.19-2.09 (m, 1H), 1.80-1.73 (m, 1H), 1.62-1.52 (m, 2H), 1.38 (s, 9H), 1.14-1.02 (m, 2H).

Step 3. Piperidin-4-ylmethyl 1-((tert-butoxycarbonyl)amino)-2,3-dihydro-1H-indene-1-carboxylate_single stereoisomer 1

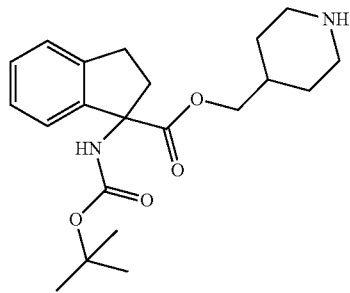 [SMILES: CC(C)(C)OC(=O)NC1(C(=O)OCC2CCNCC2)CCc2ccccc21]

The title compound was prepared as described previously (Example 15, Step 2).
$^1$H NMR (400 MHz, DMSO-$d_6$); δ 7.68 (s, 1H), 7.43 (d, J=7.5 Hz, 1H), 7.26 (d, J=3.3 Hz, 2H), 7.20 (dd, J=3.7, 3.7 Hz, 1H), 4.35 (s, 1H), 3.86-3.75 (m, 2H), 2.98-2.80 (m, 6H), 2.39 (dd, J=11.7, 11.7 Hz, 2H), 2.19-2.10 (m, 1H), 1.64-1.52 (m, 3H), 1.39 (s, 9H), 1.03-0.94 (m, 1H).

Step 4. (1-Benzylpiperidin-4-yl)methyl 1-((tert-butoxycarbonyl)amino)-2,3-dihydro-1H-indene-1-carboxylate_single stereoisomer 1

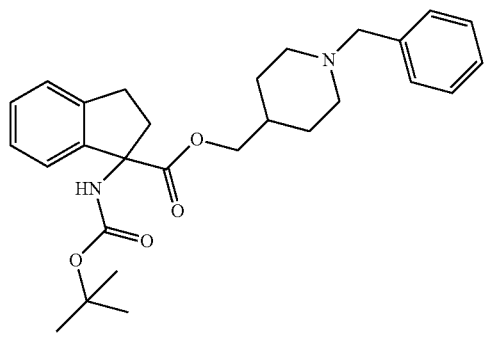 [SMILES: CC(C)(C)OC(=O)NC1(C(=O)OCC2CCN(Cc3ccccc3)CC2)CCc2ccccc21]

To a solution of piperidin-4-ylmethyl 1-((tert-butoxycarbonyl)amino)-2,3-dihydro-1H-indene-1-carboxylate (0.39 g, 1.04 mmol) in DCM (10 mL) was added acetic acid (catalytic) and benzaldehyde (0.16 mL, 1.56 mmol) and the mixture stirred for 1 hour. Sodium triacetoxyborohydride (0.441 g, 2.08 mmol) added and the reaction mixture stirred at room temperature for 18 hours. Water and DCM added and the mixture poured through a hydrophobic frit. The solvent evaporated at reduced pressure and the resulting residue purified by flash column chromatography (eluent 100% iso-hexane to 100% ethyl acetate to 10% ammonia in methanol/ethyl acetate) to afford the title compound (0.419 g, 87%).

$^1$H NMR (400 MHz, DMSO-$d_6$); δ 7.69 (s, 1H), 7.42 (d, J=7.5 Hz, 1H), 7.34-7.23 (m, 8H), 3.89-3.80 (m, 2H), 2.98-2.83 (m, 2H), 2.80-2.72 (m, 2H), 2.18-2.10 (m, 1H), 1.91 (s, 2H), 1.89-1.83 (m, 3H), 1.54 (d, J=9.2 Hz, 4H), 1.38 (s, 9H), 1.18 (dd, J=7.2, 7.2 Hz, 1H).

Step 5. (1-Benzylpiperidin-4-yl)methyl 1-amino-2,3-dihydro-1H-indene-1-carboxylate dihydrochloride

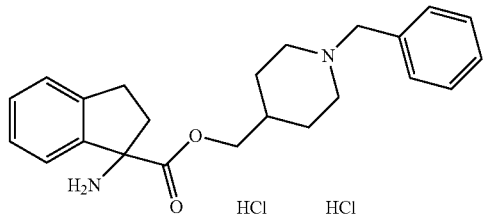 [SMILES: NC1(C(=O)OCC2CCN(Cc3ccccc3)CC2)CCc2ccccc21 ; Cl ; Cl]

To (1-benzylpiperidin-4-yl)methyl 1-((tert-butoxycarbonyl)amino)-2,3-dihydro-1H-indene-1-carboxylate (0.415 g, 0.89 mmol) was added a solution of HCl in dioxane (4M, 3 mL) and the mixture stirred at room temperature for two hours. The solvent was evaporated under reduced pressure to afford the title compound (0.40 g, 100%).

$^1$H NMR (400 MHz, DMSO-$d_6$); δ 10.76 (br s, 1H), 9.23-9.17 (m, 3H), 7.63-7.59 (m, 2H), 7.54 (d, J=7.5 Hz, 1H), 7.48-7.44 (m, 3H), 7.42-7.40 (m, 2H), 7.36-7.30 (m, 1H), 4.24 (d, J=4.1 Hz, 2H), 4.09 (dd, J=5.9, 10.9 Hz, 1H), 3.98 (dd, J=5.7, 10.9 Hz, 1H), 3.31-3.25 (m, 2H), 3.20-3.12 (m, 2H), 2.89-2.76 (m, 3H), 2.39-2.29 (m, 1H), 1.92-1.81 (m, 1H), 1.73-1.65 (m, 4H).

Step 6. (1-Benzylpiperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate_single stereoisomer 1 (Compound 22)

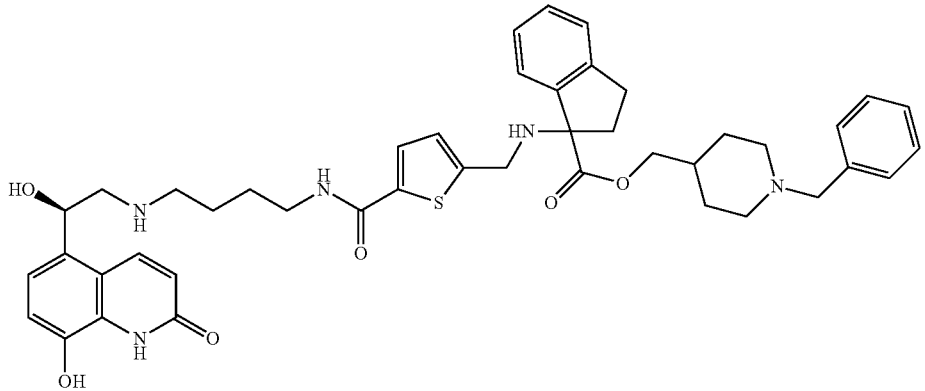 [SMILES: O=C(NCCCCNC[C@H](O)c1ccc(O)c2[nH]c(=O)ccc12)c1ccc(CNC2(C(=O)OCC3CCN(Cc4ccccc4)CC3)CCc3ccccc32)s1]

The title compound was prepared as described in Example 14 with (1-benzylpiperidin-4-yl)methyl 1-amino-2,3-dihydro-1H-indene-1-carboxylate dihydrochloride replacing (R)-quinuclidin-3-yl 2-amino-2,3-dihydro-1H-indene-2-carboxylate dihydrochloride in Step 2 and the product used in subsequent steps.

$^1$H NMR (400 MHz, MeOD); δ 8.55 (s, 1H), 8.37 (d, J=9.9 Hz, 1H), 7.50 (d, J=3.8 Hz, 1H), 7.40-7.32 (m, 6H), 7.31-7.27 (m, 3H), 7.27-7.20 (m, 1H), 7.04 (d, J=8.2 Hz, 1H), 6.96 (d, J=3.9 Hz, 1H), 6.68 (d, J=9.9 Hz, 1H), 5.38 (t, J=7.6 Hz, 1H), 4.04-3.93 (m, 2H), 3.88 (s, 2H), 3.69 (s, 2H), 3.42 (t, J=6.3 Hz, 2H), 3.21 (d, J=6.4 Hz, 2H), 3.15-3.07 (m, 4H), 3.02-2.97 (m, 2H), 2.78-2.67 (m, 1H), 2.31-2.18 (m, 3H), 1.82-1.56 (m, 7H), 1.39-1.25 (m, 2H).

In an identical fashion was prepared the compound from Isomer 2 from SFC purification.

(1-Benzylpiperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate_single stereoisomer 2 (Compound 23)

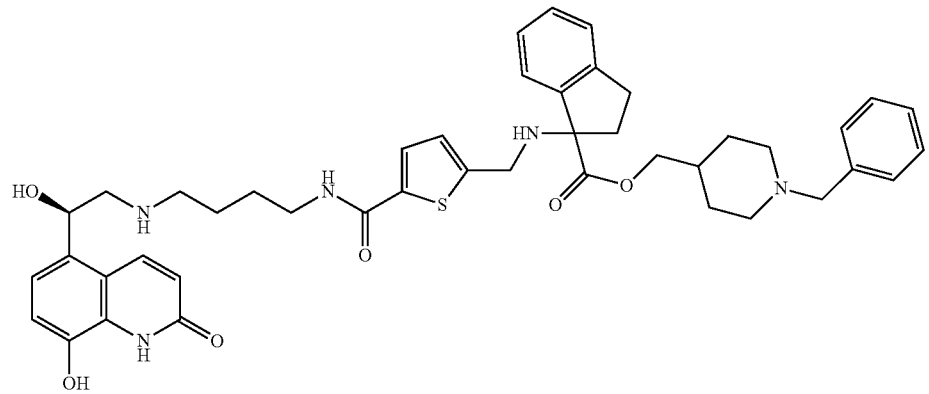 [SMILES: O=C(NCCCCNC[C@H](O)c1ccc(O)c2[nH]c(=O)ccc12)c1ccc(CNC2(C(=O)OCC3CCN(Cc4ccccc4)CC3)CCc3ccccc32)s1]

$^1$H NMR (400 MHz, MeOD); δ 8.37 (d, J=9.8 Hz, 1H), 7.63 (d, J=3.8 Hz, 1H), 7.57 (d, J=7.7 Hz, 1H), 7.49 (d, J=1.1 Hz, 7H), 7.42-7.37 (m, 1H), 7.32-7.27 (m, 2H), 7.05 (d, J=8.2 Hz, 1H), 6.65 (d, J=9.9 Hz, 1H), 5.41 (t, J=6.7 Hz, 1H), 4.50 (dd, J=13.5, 35.0 Hz, 2H), 4.28 (s, 2H), 4.16 (d, J=6.1 Hz, 2H), 3.50-3.40 (m, 4H), 3.39-3.33 (m, 2H), 3.31-3.25 (m, 2H), 3.24-3.13 (m, 2H), 3.06-2.91 (m, 3H), 2.71-2.62 (m, 1H), 1.96-1.95 (m, 1H), 1.82-1.69 (m, 6H), 1.50-1.39 (m, 2H).

Example 21. 1-Benzylpiperidin-4-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate_single stereoisomer 1 (Compound 24)

Step 1. 1-((tert-Butoxycarbonyl)amino)-2,3-dihydro-1H-indene-1-carboxylic acid

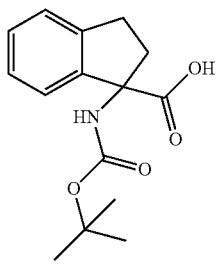 [SMILES: CC(C)(C)OC(=O)NC1(C(=O)O)CCc2ccccc21]

To a solution of benzyl 4-(((1-((tert-butoxycarbonyl)amino)-2,3-dihydro-1H-indene-1-carbonyl)oxy)methyl)piperidine-1-carboxylate_isomer 1 (3.6 g, 7.08 mmol) in THF/methanol (20 mL/20 mL) was added aqueous sodium hydroxide (2M, 36 mL). The reaction mixture was stirred at room temperature for one hour. The solvent was evaporated at reduced pressure and the residue partitioned between DCM and aqueous potassium hydrogensulfate (10%). The organic phase removed and the aqueous extracted with further DCM (×3). The combined organic extracts poured through a hydrophobic phase and the filtrate evaporated at reduced pressure. The residue was purified by flash column chromatography (eluent; 100% iso-hexane to 100% ethyl acetate) to afford the title compound (2.08 g, >100%).

$^1$H NMR (400 MHz, DMSO-d$_6$); δ 12.41-12.41 (m, 1H), 7.44 (d, J=7.2 Hz, 2H), 7.25 (d, J=3.6 Hz, 2H), 7.22-7.17 (m, 1H), 2.97-2.90 (m, 2H), 2.77 (s, 2H), 1.38 (s, 9H).

Step 2. 1-Benzylpiperidin-4-yl 1-amino-2,3-dihydro-1H-indene-1-carboxylate dihydrochloride

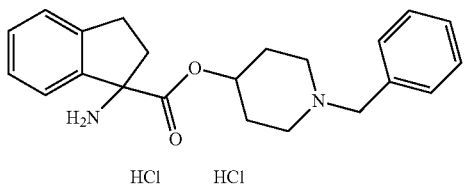 [SMILES: NC1(C(=O)OC2CCN(Cc3ccccc3)CC2)CCc2ccccc21 ; Cl ; Cl]

To a solution of 1-((tert-butoxycarbonyl)amino)-2,3-dihydro-1H-indene-1-carboxylic acid (0.17 g, 0.61 mmol) in DMF (1 mL) was added CDI (0.15 g, 0.92 mmol) and the reaction mixture stirred at 60° C. for one hour. The mixture was cooled and a pre-mixed suspension of 1-benzylpiperidin-4-ol (0.151 g, 0.8 mmol) and sodium hydride (60% dispersion in mineral oil, 0.04 g, 0.92 mmol) in DMF (1 mL) was added. The reaction mixture was stirred at room temperature for two hours. The reaction mixture was diluted with ethyl acetate and the mixture washed with aqueous sodium carbonate (10%). The organic phase was dried over magnesium sulfate, filtered and evaporated at reduced pressure. The residue was treated with a solution of HCl in dioxane (4M, 2 mL) and the mixture stirred at room temperature for one hour. The solvent was evaporated at reduced pressure to afford the title compound (0.360 g, >100%).

$^1$H NMR (400 MHz, DMSO-d$_6$); δ 10.76 (br s, 1H), 9.23-9.17 (m, 3H), 7.63-7.59 (m, 2H), 7.54 (d, J=7.5 Hz, 1H), 7.48-7.44 (m, 3H), 7.42-7.40 (m, 2H), 7.36-7.30 (m, 1H), 4.71 (d, J=4.1 Hz, 1H), 4.09 (dd, J=5.9, 10.9 Hz, 1H), 3.98 (dd, J=5.7, 10.9 Hz, 1H), 3.31-3.25 (m, 2H), 3.20-3.12 (m, 2H), 2.89-2.76 (m, 3H), 1.92-1.81 (m, 1H), 1.73-1.65 (m, 4H).

Step 3. 1-Benzylpiperidin-4-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate_single stereoisomer 1 (Compound 24)

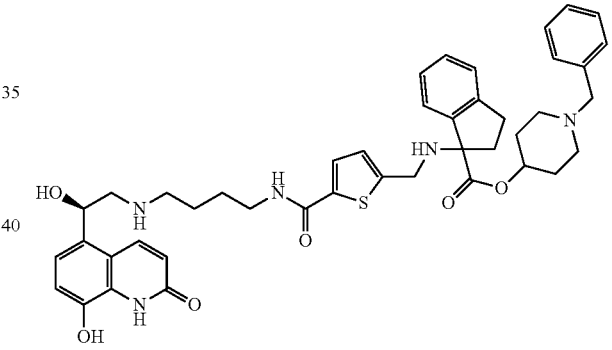

The title compound was prepared as described in Example 14 with (1-benzylpiperidin-4-yl)methyl 1-amino-2,3-dihydro-1H-indene-1-carboxylate dihydrochloride replacing (R)-quinuclidin-3-yl 2-amino-2,3-dihydro-1H-indene-2-carboxylate dihydrochloride in Step 2 and the product used in subsequent steps.

$^1$H NMR (400 MHz, DMSO-d$_6$, 90° C.); δ 8.23 (d, J=9.9 Hz, 1H), 8.08-8.06 (m, 1H), 7.56 (d, J=3.3 Hz, 1H), 7.52 (s, 5H), 7.45 (d, J=7.6 Hz, 1H), 7.36 (d, J=4.0 Hz, 2H), 7.31-7.27 (m, 1H), 7.20 (d, J=8.1 Hz, 1H), 7.07 (d, J=8.1 Hz, 1H), 6.97 (d, J=3.8 Hz, 1H), 6.61 (d, J=9.9 Hz, 1H), 5.39 (dd, J=5.1, 7.1 Hz, 1H), 5.06-5.02 (m, 1H), 4.23 (s, 2H), 3.99-3.89 (m, 2H), 3.37-3.27 (m, 2H), 3.22-3.00 (m, 10H), 2.74-2.67 (m, 1H), 2.34-2.25 (m, 1H), 2.15-2.05 (m, 2H), 1.97-1.84 (m, 1H), 1.83-1.74 (m, 3H), 1.71-1.63 (m, 2H).

The following compounds were prepared in the same fashion using the appropriate alcohol in Step 2 above:

(R)-1-Benzylpiperidin-3-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate_single stereoisomer 1 (Compound 25)

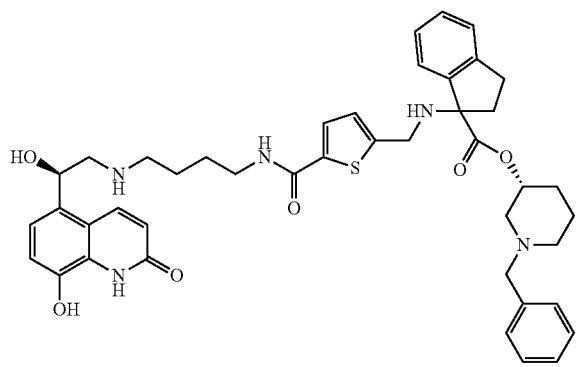 [SMILES: O=C(NCCCCNC[C@H](O)c1ccc(O)c2[nH]c(=O)ccc12)c1ccc(CNC2(C(=O)O[C@@H]3CCCN(Cc4ccccc4)C3)CCc3ccccc32)s1]

¹H NMR (400 MHz, DMSO-d₆); δ 1.33 (t, J=5.6 Hz, 1H), 8.17 (d, J=9.9 Hz, 1H), 7.53 (d, J=3.8 Hz, 1H), 7.39 (d, J=7.4 Hz, 1H), 7.30-7.20 (m, 8H), 7.04 (d, J=8.3 Hz, 1H), 6.90-6.85 (m, 2H), 6.48 (d, J=9.8 Hz, 1H), 4.99 (dd, J=4.3, 8.0 Hz, 1H), 4.76-4.72 (m, 1H), 3.84-3.76 (m, 2H), 3.50-3.39 (m, 2H), 3.31-3.16 (m, 4H), 3.03-2.90 (m, 3H), 2.70-2.54 (m, 3H), 2.39-2.33 (m, 1H), 2.25-2.09 (m, 3H), 1.73-1.69 (m, 2H), 1.54-1.39 (m, 6H).

(R)-1-Benzylpyrrolidin-3-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate_single stereoisomer 1 (Compound 26)

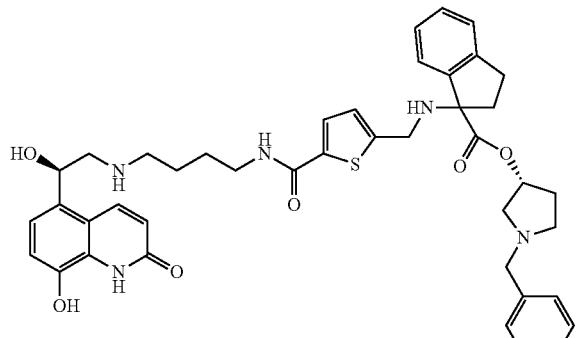

¹H NMR (400 MHz, DMSO-d₆, 100° C.); δ 1.33 (t, J=5.6 Hz, 1H), 8.17 (d, J=9.9 Hz, 1H), 7.53 (d, J=3.8 Hz, 1H), 7.39 (d, J=7.4 Hz, 1H), 7.30-7.20 (m, 8H), 7.04 (d, J=8.3 Hz, 1H), 6.90-6.85 (m, 2H), 6.48 (d, J=9.8 Hz, 1H), 4.99 (dd, J=4.3, 8.0 Hz, 1H), 4.76-4.72 (m, 1H), 3.84-3.76 (m, 2H), 3.50-3.39 (m, 2H), 3.31-3.16 (m, 4H), 3.03-2.90 (m, 3H), 2.70-2.54 (m, 3H), 2.39-2.33 (m, 1H), 2.25-2.09 (m, 3H), 1.73-1.69 (m, 2H), 1.54-1.39 (m, 4H).

The following compound was prepared in the same fashion using benzyl 4-(((1-((tert-butoxycarbonyl)amino)-2,3-dihydro-1H-indene-1-carbonyl)oxy)methyl)piperidine-1-carboxylate_isomer 2 in Step 1 above:

1-Benzylpiperidin-4-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate_single stereoisomer 2 (Compound 27)

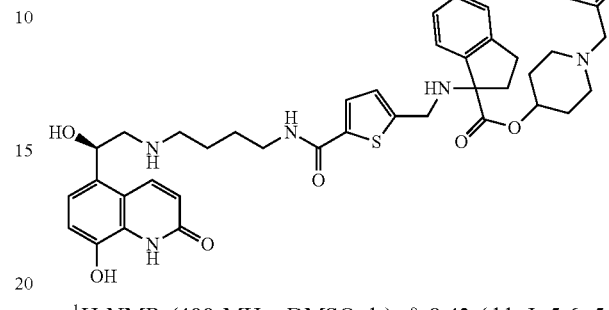

¹H NMR (400 MHz, DMSO-d₆); δ 8.42 (dd, J=5.6, 5.6 Hz, 1H), 8.34 (s, 2H), 8.23 (d, J=9.9 Hz, 1H), 7.59 (d, J=3.8 Hz, 1H), 7.44 (d, J=7.3 Hz, 1H), 7.38-7.25 (m, 8H), 7.16 (d, J=8.3 Hz, 1H), 7.01 (d, J=8.1 Hz, 1H), 6.96 (d, J=3.5 Hz, 1H), 6.58 (d, J=9.9 Hz, 1H), 5.26 (dd, J=4.0, 8.6 Hz, 1H), 4.84-4.78 (m, 1H), 3.86 (s, 2H), 3.46 (s, 2H), 3.30-3.22 (m, 3H), 3.09-2.83 (m, 6H), 2.49-2.45 (m, 1H), 2.40-2.15 (m, 4H), 1.85-1.75 (m, 2H), 1.64-1.53 (m, 7H).

The following compound was prepared in the same fashion using benzyl 4-(((1-((tert-butoxycarbonyl)amino)-2,3-dihydro-1H-indene-1-carbonyl)oxy)methyl)piperidine-1-carboxylate_isomer 2 in Step 1 and using the appropriate alcohol in Step 2 above:

(R)-1-benzylpyrrolidin-3-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate_single stereoisomer 2 (Compound 28)

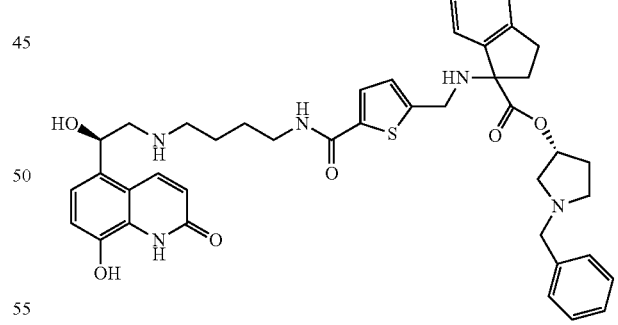

¹H NMR (400 MHz, DMSO-d₆, 90° C.); δ 8.14 (d, J=9.9 Hz, 1H), 8.06 (s, 1H), 7.48 (d, J=3.6 Hz, 1H), 7.42 (s, 6H), 7.30-7.26 (m, 2H), 7.23-7.19 (m, 1H), 7.12 (d, J=8.2 Hz, 1H), 6.98 (d, J=8.2 Hz, 1H), 6.90 (d, J=3.5 Hz, 1H), 6.53 (d, J=9.9 Hz, 1H), 5.35-5.29 (m, 2H), 4.28-4.19 (m, 2H), 3.92-3.82 (m, 2H), 3.28-3.22 (m, 6H), 3.11-2.98 (m, 6H), 2.69-2.61 (m, 1H), 2.43-2.28 (m, 1H), 2.27-2.19 (m, 1H), 1.97 (s, 1H), 1.71-1.66 (m, 2H), 1.62-1.54 (m, 2H).

The compounds prepared in the above described Examples are reported in the following table along with their analytical and NMR data.

| No | $R_t$ (min) | Method | NMR data | Structure | Chemical name | Salt Two equiv. |
|---|---|---|---|---|---|---|
| 1 | 6.89 | 1 | ¹H NMR (400 MHz, MeOD): δ 8.37 (d, J = 9.9 Hz, 1H), 8.02-8.00 (m, 1H), 7.90 (d, J = 9.5 Hz, 1H), 7.73-7.52 (m, 5H), 7.46-7.38 (m, 1H), 7.31 (d, J = 8.3 Hz, 1H), 7.05 (d, J = 8.2 Hz, 1H), 6.66 (d, J = 9.8 Hz, 1H), 5.44-5.39 (m, 1H), 5.39-5.28 (m, 1H), 4.39 (dd, J = 8.8, 12.5 Hz, 1H), 4.29 (dd, J = 5.5, 12.5 Hz, 1H), 3.83-3.72 (m, 1H), 3.50-3.35 (m, 3H), 3.32-3.21 (m, 6H), 3.18-2.99 (m, 4H), 2.88-2.72 (m, 2H), 2.49-2.45 (m, 0.5H), 2.25-2.20 (m, 0.5H), 2.10-1.72 (m, 6H), 1.71-1.62 (m, 1H), 1.33-1.24 (m, 1H). | 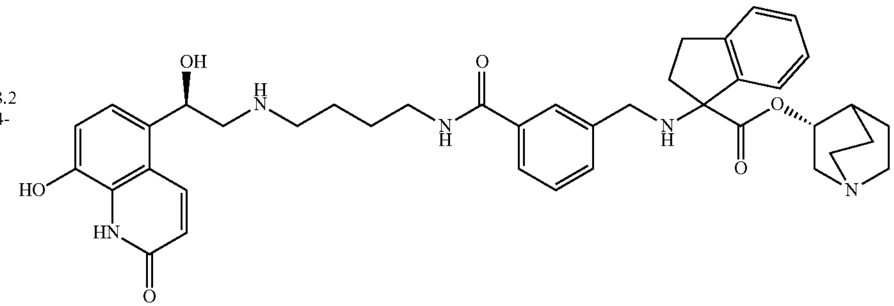 | (R)-quinuclidin-3-yl 1-(3-((4-(((R)-2-hydroxy-2-(8-hydroxy-2-oxo-1,2-dihydroquinolin-5-yl)ethyl)amino)butyl)carbamoyl)benzyl)amino)-2,3-dihydro-1H-indene-1-carboxylate | TFA |
| 2 | 8.27 | 1 | ¹H NMR (400 MHz, MeOD): δ 8.52 (s, 2H), 8.39 (d, J = 9.9 Hz, 1H), 7.61 (t, J = 8.9 Hz, 1H), 7.46-7.28 (m, 7H), 7.14-7.10 (m, 1H), 7.05 (d, J = 8.2 Hz, 1H), 6.70 (d, J = 9.8 Hz, 1H), 5.41 (t, J = 6.7 Hz, 1H), 5.04-5.01 (m, 0.5H), 4.99-4.95 (m, 0.5H), 4.09 (t, J = 5.6 Hz, 2H), 3.60-3.50 (m, 1H), 3.31-3.22 (m, 3H), 3.19-3.05 (m, 8H), 2.99-2.90 (m, 1H), 2.41-2.22 (m, 2H), 2.00-1.79 (m, 7H), 1.73-1.59 (m, 3H). | 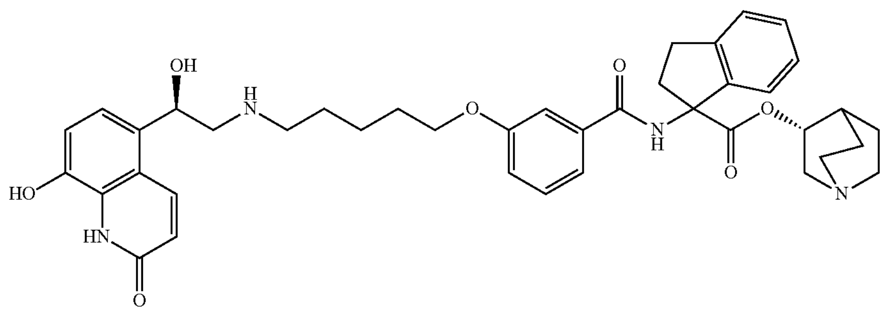 | (R)-quinuclidin-3-yl 1-(3-((5-(((R)-2-hydroxy-2-(8-hydroxy-2-oxo-1,2-dihydroquinolin-5-yl)ethyl)amino)pentyl)oxy)benzamido)-2,3-dihydro-1H-indene-1-carboxylate | Formate |
| 3 | 7.34 | 1 | ¹H NMR (400 MHz, MeOD): δ 8.39 (d, J = 9.9 Hz, 1H), 7.64 (dd, J = 7.7, 17.0 Hz, 1H), 7.54-7.50 (m, 2H), 7.44-7.30 (m, 3H), 7.10-6.99 (m, 4H), 6.68 (dd, J = 5.6, 7.8 Hz, 1H), 5.43 (dd, J = 9.8 Hz, 1H), 5.35-5.25 (m, 1H), 4.30-4.15 (m, 2H), 4.07-4.02 (m, 2H), 3.82-3.71 (m, 1H), 3.46-3.35 (m, 2H), 3.30-3.21 (m, 4H), 3.17-2.97 (m, 4H), 2.89-2.69 (m, 2H), 2.68 (s, 2H), 2.49-2.41 (m, 0.5H), 2.27-2.18 (m, 0.5H), 2.08-1.79 (m, 6H), 1.67-1.59 (m, 3H). | 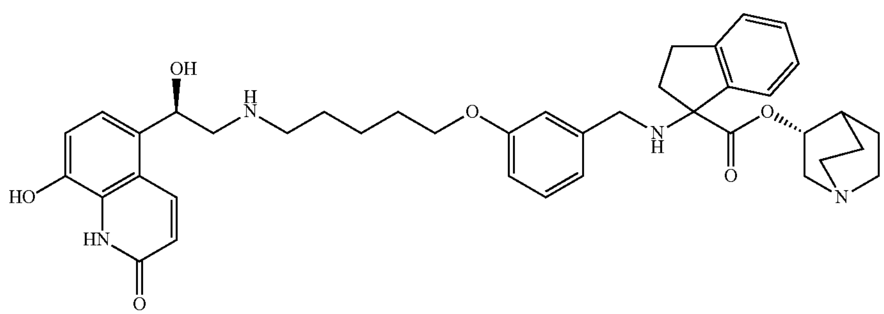 [SMILES: O=C(O[C@H]1CN2CCC1CC2)C1(NCc2cccc(OCCCCCNC[C@H](O)c3ccc(O)c4[nH]c(=O)ccc34)c2)CCc2ccccc21] | (R)-quinuclidin-3-yl 1-((3-((5-(((R)-2-hydroxy-2-(8-hydroxy-2-oxo-1,2-dihydroquinolin-5-yl)ethyl)amino)pentyl)oxy)benzyl)amino)-2,3-dihydro-1H-indene-1-carboxylate | TFA |

| No | R$_t$ (min) | Method | NMR data | Structure | Chemical name | Salt Two equiv. |
|---|---|---|---|---|---|---|
| 4 | 7.79 | 2 | $^1$H NMR (400 MHz, DMSO-d$_6$ @ 90° C.); δ 8.17 (d, J = 9.9 Hz, 1H), 8.12-8.09 (m, 1H), 7.51 (d, J = 3.8 Hz, 1H), 7.45 (dd, J = 7.5, 16.7 Hz, 1H), 7.33-7.24 (m, 3H), 7.15 (d, J = 8.2 Hz, 1H), 7.01 (d, J = 8.2 Hz, 1H), 6.93 (d, J = 3.6 Hz, 1H), 6.56 (d, J = 9.9 Hz, 1H), 5.33 (dd, J = 4.4, 8.5 Hz, 1H), 5.11-5.05 (m, 1H), 4.00-3.84 (m, 2H), 3.71-3.65 (m, 1H), 3.30-3.01 (m, 13H), 2.75-2.64 (m, 1H), 2.35-2.16 (m, 1H), 1.93-1.82 (m, 3H), 1.75-1.57 (m, 6H). | 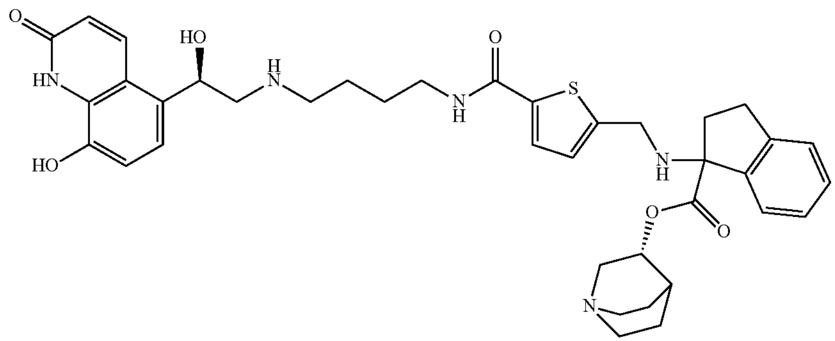 [SMILES: O=C(NCCCCNC[C@H](O)c1ccc(O)c2[nH]c(=O)ccc12)c1ccc(CNC2(C(=O)O[C@H]3CN4CCC3CC4)CCc3ccccc32)s1] | (R)-quinuclidin-3-yl 1-((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate | TFA |
| 5 | 7.74 | 2 | $^1$H NMR (400 MHz, MeOD); δ 8.47 (s, 3H), 8.37 (d, J = 9.6 Hz, 1H), 7.83 (s, 1H), 7.72 (d, J = 7.6 Hz, 1H), 7.55 (d, J = 7.6 Hz, 1H), 7.43 (t, J = 8.7 Hz, 1H), 7.32-7.23 (m, 2H), 7.22-7.12 (m, 2H), 7.04 (d, J = 8.1 Hz, 1H), 6.67 (d, J = 9.1 Hz, 1H), 5.42 (s, 1H), 5.07-5.04 (m, 1H), 3.76 (d, J = 2.5 Hz, 2H), 3.65-3.55 (m, 1H), 3.46 (br s, 2H), 3.25 (d, J = 3.3 Hz, 2H), 3.21-3.00 (m, 8H), 2.92-2.79 (m, 2H), 2.40-2.31 (m, 6H), 2.06-1.94 (m, 1H), 1.81 (br s, 3H), 1.74 (br s, 3H), 1.65-1.57 (m, 1H). | 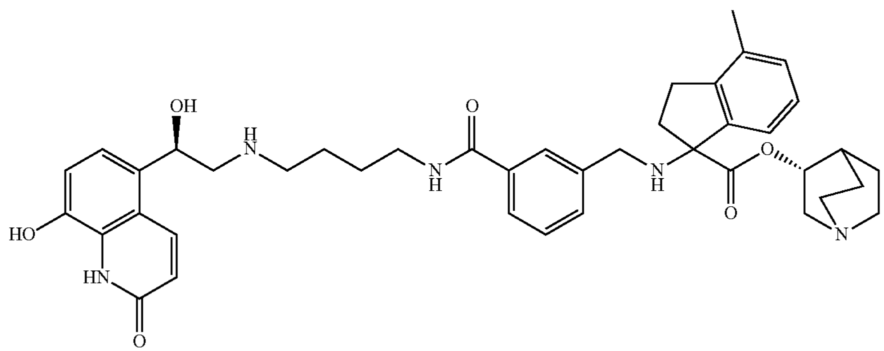 [SMILES: Cc1cccc2c1CCC2(NCc1cccc(C(=O)NCCCCNC[C@H](O)c2ccc(O)c3[nH]c(=O)ccc23)c1)C(=O)O[C@H]1CN2CCC1CC2] | (R)-quinuclidin-3-yl 1-((3-((4-(((R)-2-hydroxy-2-(8-hydroxy-2-oxo-1,2-dihydroquinolin-5-yl)ethyl)amino)butyl)carbamoyl)benzyl)amino)-4-methyl-2,3-dihydro-1H-indene-1-carboxylate | Formate |

| No | R₁ (min) | Method | NMR data | Structure | Chemical name | Salt Two equiv. |
|---|---|---|---|---|---|---|
| 5A | 7.98 | 2 | ¹H NMR (400 MHz, MeOD); δ 8.39 (d, J = 11.2 Hz, 1H), 7.46-7.35 (m, 4H), 7.31 (d, J = 8.2 Hz, 1H), 7.25-7.18 (m, 2H), 7.13-7.11 (m, 1H), 7.05 (d, J = 8.2 Hz, 1H), 6.70 (d, J = 9.9 Hz, 1H), 5.41 (t, J = 9.3 Hz, 1H), 5.12-5.08 (m, 1H), 4.08 (t, J = 7.5 Hz, 2H), 3.73 (ddd, J = 2.5, 8.4, 14.2 Hz, 1H), 3.27 (t, J = 11.2 Hz, 8H), 3.17-3.03 (m, 4H), 2.32 (s, 5H), 2.05 (dd, J = 16.8, 27.9 Hz, 2H), 1.87 (tt, J = 18.0, 17.7 Hz, 6H), 1.68-1.59 (m, 2H). | 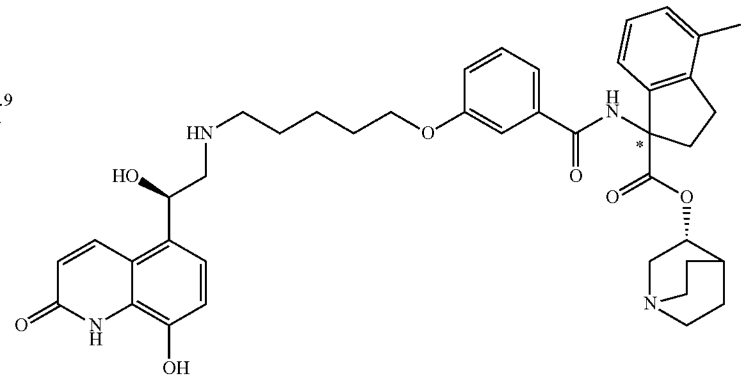 | (R)-quinuclidin-3-yl 1-(3-((5-(((R)-2-(8-hydroxy-2-oxo-1,2-dihydroquinolin-5-yl)ethyl)amino)pentyl)oxy)benzamido)-4-methyl-2,3-dihydro-1H-indene-1-carboxylate single diastereoisomer 1 | TFA |
| 5B | 7.17 | 2 | ¹H NMR (400 MHz, MeOD); δ 8.38 (d, J = 9.9 Hz, 1H), 7.47 (d, J = 7.8 Hz, 1H), 7.43-7.36 (m, 3H), 7.31 (d, J = 8.4 Hz, 1H), 7.26-7.19 (m, 2H), 7.14-7.11 (m, 1H), 7.05 (d, J = 8.2 Hz, 1H), 6.70 (d, J = 9.8 Hz, 1H), 5.41 (t, J = 8.7 Hz), 5.05-4.98 (m, 1H), 4.07 (t, J = 7.3 Hz, 2H), 3.72 (ddd, J = 2.6, 8.2, 14.1 Hz, 1H), 3.38 (dd, J = 7.3, 19.6 Hz, 1H), 3.34-3.32 (ddd, J = 6.7, 6.7, 6.7 Hz, 2H), 3.06 (dd, J = 8.6, 11.0 Hz, 3H), 2.39 (d, J = 17.1 Hz, 1H), 2.33-2.25 (m, 4H), 2.06-1.84 (m, 7H), 1.68-1.59 (m, 2H). | 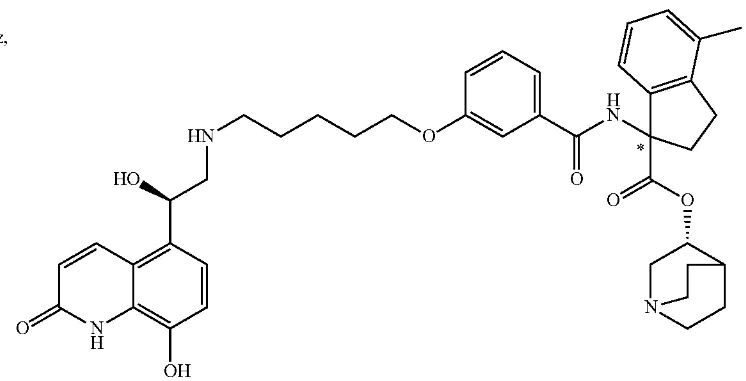 | (R)-quinuclidin-3-yl 1-(3-((5-(((R)-2-(8-hydroxy-2-oxo-1,2-dihydroquinolin-5-yl)ethyl)amino)pentyl)oxy)benzamido)-4-methyl-2,3-dihydro-1H-indene-1-carboxylate single diastereoisomer 2 | TFA |

| No | R$_t$ (min) | Method | NMR data | Structure | Chemical name | Salt Two equiv. |
|---|---|---|---|---|---|---|
| 6 | 8.72 | 2 | $^1$H NMR (400 MHz, DMSO-d$_6$): δ 10.51 (d, J = 3.9 Hz, 2H), 9.78-9.78 (m, 1H), 9.29 (d, J = 37.0 Hz, 1H), 8.67 (s, 2H), 8.17 (d, J = 9.9 Hz, 1H), 7.63-7.32 (m, 6H), 7.31-7.24 (m, 1H), 7.17-7.09 (m, 2H), 6.99 (d, J = 8.2 Hz, 1H), 6.58 (d, J = 9.9 Hz, 1H), 6.20-6.19 (m, 1H), 5.32 (d, J = 9.2 Hz, 1H), 5.03-4.99 (m, 1H), 4.02 (s, 2H), 3.70-3.63 (m, 1H), 3.24-2.98 (m, 11H), 2.37-2.17 (m, 2H), 1.68-1.60 | 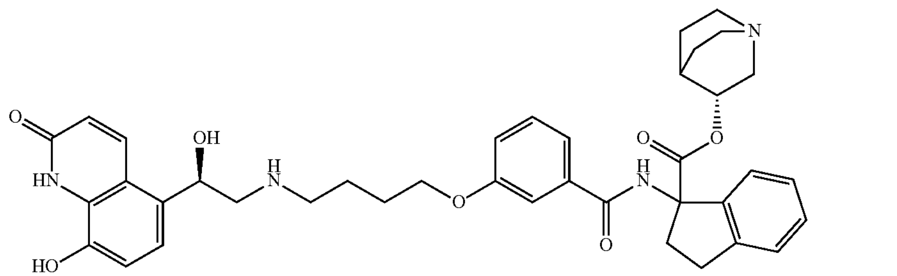 [SMILES: O=C(NC1(C(=O)O[C@H]2CN3CCC2CC3)CCc2ccccc21)c1cccc(OCCCCNC[C@H](O)c2ccc(O)c3[nH]c(=O)ccc23)c1] | (R)-quinuclidin-3-yl 1-(3-(4-(((R)-2-hydroxy-2-(8-hydroxy-2-oxo-1,2-dihydroquinolin-5-yl)ethyl)amino)butoxy)benzamido)-2,3-dihydro-1H-indene-1-carboxylate | TFA |
| 7 | 2.33 | 3 | $^1$H NMR (400 MHz, DMSO-d$_6$): δ 10.52 (s, 1H), 9.11 (s, 1H), 8.94-8.93 (m, 1H), 8.59-8.58 (m, 2H), 8.16 (d, J = 9.9 Hz, 1H), 7.53 (d, J = 7.5 Hz, 1H), 7.48 (d, J = 7.8 Hz, 1H), 7.44 (dd, J = 2.1, 2.1 Hz, 1H), 7.39-7.33 (m, 3H), 7.29-7.23 (m, 1H), 7.15 (d, J = 8.2 Hz, 1H), 7.09 (dd, J = 2.0, 8.0 Hz, 1H), 6.99 (d, J = 8.2 Hz, 1H), 6.59 (d, J = 9.8 Hz, 1H), 5.31 (dd, J = 6.3, 6.3 Hz, 1H), 4.00 (dd, J = 6.5, 6.3 Hz, 2H), 3.89 (d, J = 6.5 Hz, 2H), 3.48-3.38 (m, 1H), 3.31 (d, J = 11.3 Hz, 2H), 3.13-2.87 (m, 8H), 2.30-2.20 (m, 1H), 1.95-1.59 (m, 7H), 1.47-1.35 (m, 6H), 1.21 (d, J = 6.7 Hz, 6H). | 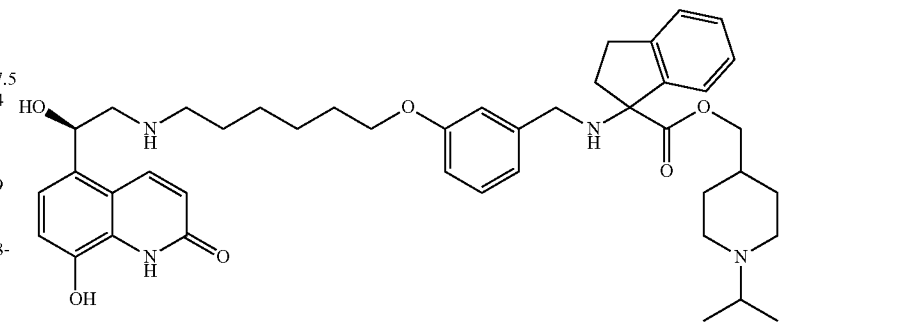 | (1-isopropylpiperidin-4-yl)methyl 1-(3-(((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate | TFA |
| 8 | 8.64 | 2 | $^1$H NMR (400 MHz, MeOD): δ 8.52 (s, 2H), 8.40-8.33 (m, 2H), 8.06-7.99 (m, 2H), 7.65-7.57 (m, 2H), 7.37-7.28 (m, 4H), 7.04 (d, J = 8.2 Hz, 1H), 6.68 (d, J = 9.9 Hz, 1H), 5.41 (dd, J = 6.7, 6.7 Hz, 1H), 5.07-4.97 (m, 1H), 3.61-3.50 (m, 1H), 3.47 (dd, J = 6.7, 6.7 Hz, 3H), 3.39-3.04 (m, 5H), 3.01-2.92 (m, 1H), 2.44-2.29 (m, 2H), 2.23-2.17 (m, 1H), 2.06-1.89 (m, 3H), 1.86-1.66 (m, 9H). | 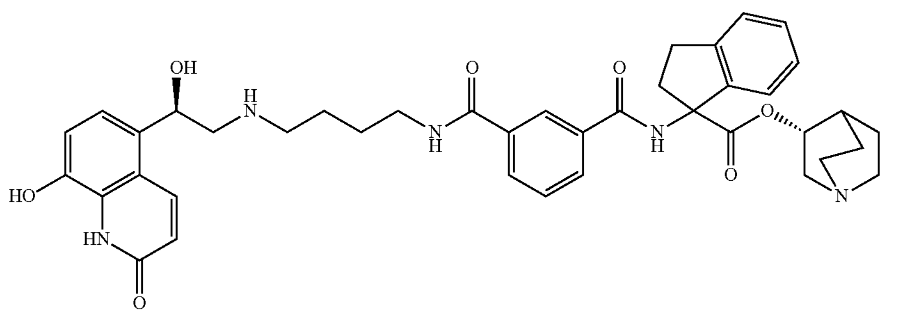 [SMILES: O=C(NCCCCNC[C@H](O)c1ccc(O)c2[nH]c(=O)ccc12)c1cccc(C(=O)NC2(C(=O)O[C@H]3CN4CCC3CC4)CCc3ccccc32)c1] | (R)-quinuclidin-3-yl 1-(3-(4-(((R)-2-hydroxy-2-(8-hydroxy-2-oxo-1,2-dihydroquinolin-5-yl)ethyl)amino)butyl)carbamoyl)benzamido)-2,3-dihydro-1H-indene-1-carboxylate | Formate |

| No | R$_t$ (min) | Method | $^1$H NMR data | Structure | Chemical name | Salt Two equiv. |
|---|---|---|---|---|---|---|
| 9 | 2.44 | 3 | $^1$H NMR (400 MHz, MeOD): δ 8.39 (d, J = 9.9 Hz, 1H), 7.56 (d, J = 8.7 Hz, 5H), 7.51 (s, 5H), 7.41-7.26 (m, 4H), 7.12-7.09 (m, 1H), 7.05 (d, J = 8.2 Hz, 1H), 6.70 (d, J = 9.8 Hz, 1H), 5.41 (dd, J = 6.8, 6.8 Hz, 1H), 4.29 (s, 2H), 4.07-4.01 (m, 4H), 3.50-3.43 (m, 2H), 3.29-3.22 (m, 4H), 3.11 (dd, J = 7.8, 7.8 Hz, 4H), 3.02-2.94 (m, 2H), 2.37-2.28 (m, 1H), 1.99-1.76 (m, 6H), 1.61-1.46 (m, 6H). | 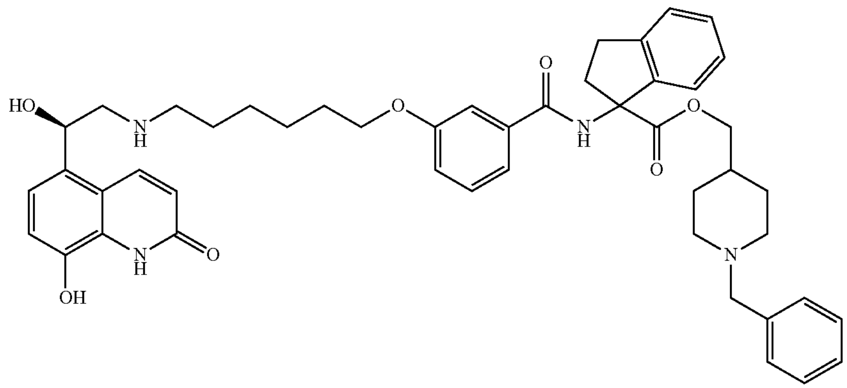 [SMILES: O=C(NC1(C(=O)OCC2CCN(Cc3ccccc3)CC2)CCc2ccccc21)c1cccc(OCCCCCCNC[C@H](O)c2ccc(O)c3[nH]c(=O)ccc23)c1] | (1-benzylpiperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate | TFA |
| 10 | 9.45 | 2 | $^1$H NMR (400 MHz, MeOD): δ 9.03-9.03 (m, 1H), 8.39 (d, J = 9.9 Hz, 1H), 7.69 (s, 1H), 7.56 (d, J = 7.5 Hz, 1H), 7.43-7.27 (m, 7H), 7.13-7.09 (m, 1H), 7.05 (d, J = 8.2 Hz, 1H), 6.70 (d, J = 9.9 Hz, 2H), 6.56-6.53 (m, 1H), 5.42 (dd, J = 6.7, 6.7 Hz, 1H), 4.38 (s, 2H), 4.04 (dd, J = 6.1, 6.1 Hz, 4H), 3.46-3.42 (m, 2H), 3.30-3.23 (m, 3H), 3.15-3.08 (m, 4H), 2.97-2.96 (m, 2H), 2.38-2.28 (m, 1H), 2.01-1.76 (m, 6H), 1.62-1.48 (m, 7H). | 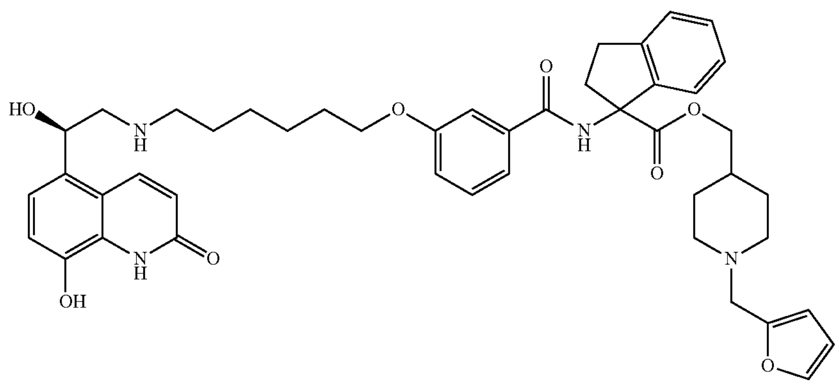 [SMILES: O=C(NC1(C(=O)OCC2CCN(Cc3ccco3)CC2)CCc2ccccc21)c1cccc(OCCCCCCNC[C@H](O)c2ccc(O)c3[nH]c(=O)ccc23)c1] | (1-(furan-2-ylmethyl)piperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate | TFA |

| No | R$_t$ (min) | Method | NMR data | Structure | Chemical name | Salt Two equiv. |
|---|---|---|---|---|---|---|
| 11 | 7.28 | 2 | $^1$H NMR (400 MHz, DMSO, 90° C); δ 8.69 (s, 1H), 8.18 (d, J = 9.9 Hz, 1H), 7.54 (d, J = 7.7 Hz, 1H), 7.45 (d, J = 7.8 Hz, 1H), 7.41-7.40 (m, 1H), 7.36-7.30 (m, 3H), 7.26-7.18 (m, 2H), 7.15 (d, J = 8.3 Hz, 1H), 7.07 (dd, J = 2.1, 8.0 Hz, 1H), 7.01 (d, J = 8.2 Hz, 1H), 6.86-6.82 (m, 3H), 6.57 (d, J = 9.9 Hz, 1H), 5.33 (dd, J = 4.4, 8.7 Hz, 1H), 4.03 (t, J = 6.4 Hz, 2H), 3.95 (s, 2H), 3.17-2.99 (m, 16H), 2.39-2.30 (m, 2H), 1.79-1.67 (m, 6H), 1.51-1.40 (m, 6H). | 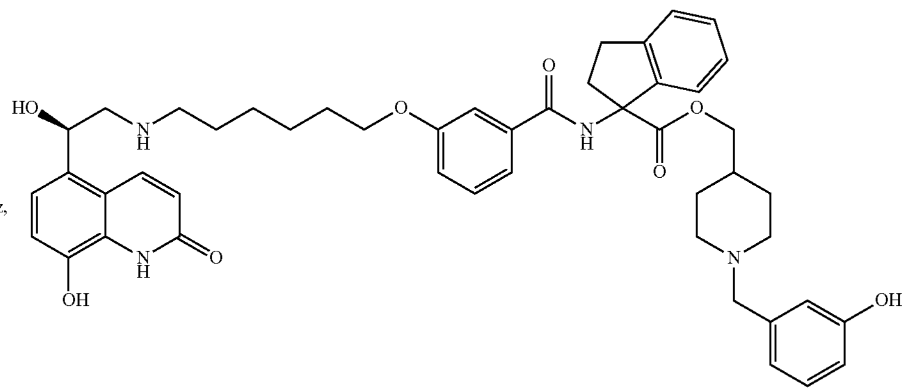 | (1-(3-hydroxybenzyl) piperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate | TFA |
| 12 | 6.95 | 2 | $^1$H NMR (400 MHz, MeOD): δ 8.35 (d, J = 1.4, 9.9 Hz, 1H), 7.87 (d, J = 7.0 Hz, 1H), 7.81 (dd, J = 7.4, 7.4 Hz, 1H), 7.63-7.57 (m, 2H), 7.50-7.44 (m, 1H), 7.38-7.35 (m, 2H), 7.35-7.27 (m, 2H), 7.05 (d, J = 8.2 Hz, 1H), 6.68 (d, J = 9.9 Hz, 1H), 5.40-5.35 (m, 1H), 5.12-4.92 (m, 1H), 4.59 (s, 2H), 3.77-3.68 (m, 1H), 3.61 (dd, J = 5.9, 5.9 Hz, 2H), 3.30-3.20 (m, 7H), 3.19-3.05 (m, 5H), 2.40-2.25 (m, 2H), 2.08-1.74 (m, 8H). | 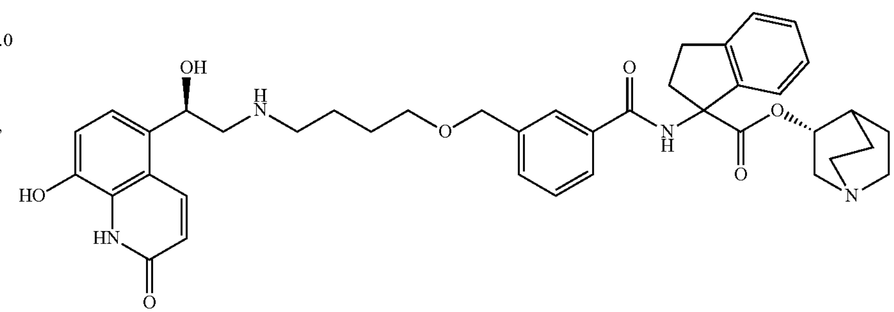 | (R)-quinuclidin-3-yl 1-(3-((4-(((R)-2-hydroxy-2-(8-hydroxy-2-oxo-1,2-dihydroquinolin-5-yl)ethyl)amino)butoxy)methyl)benzamido)-2,3-dihydro-1H-indene-1-carboxylate | TFA |

| No | R_t (min) | Method | NMR data | Structure | Chemical name | Salt Two equiv. |
|----|-----------|--------|----------|-----------|---------------|-----------------|
| 13 | 7.10 | 2 | $^1$H NMR (400 MHz, MeOD): δ 8.52 (s, 2H), 8.39 (d, J = 9.9 Hz, 1H), 7.44-7.34 (m, 3H), 7.32-7.19 (m, 6H), 7.13-7.10 (m, 1H), 7.05 (d, J = 8.2 Hz, 1H), 6.70 (d, J = 9.8 Hz, 1H), 5.41 (dd, J = 6.8, 6.8 Hz, 1H), 5.09-5.03 (m, 1H), 4.07 (dd, J = 6.1, 6.1 Hz, 2H), 3.84 (d, J = 16.7 Hz, 1H), 3.69 (d, J = 16.6 Hz, 1H), 3.59 (ddd, J = 2.5, 8.3, 14.3 Hz, 1H), 3.50-3.35 (m, 2H), 3.24 (d, J = 6.8 Hz, 2H), 3.16-3.08 (m, 6H), 2.96-2.85 (m, 1H), 2.26-2.23 (m, 1H), 2.01-1.78 (m, 7H), 1.68-1.60 (m, 3H). | 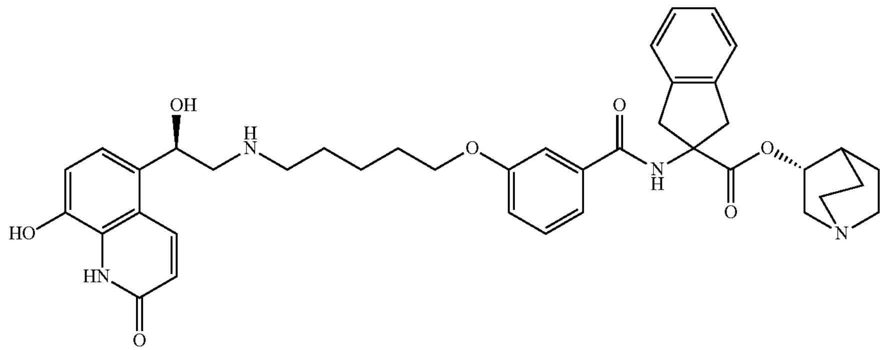 [SMILES: O=C(NC1(C(=O)O[C@H]2CN3CCC2CC3)Cc2ccccc2C1)c1cccc(OCCCCCNC[C@H](O)c2ccc(O)c3[nH]c(=O)ccc23)c1] | (R)-quinuclidin-3-yl 2-(3-((5-(((R)-2-hydroxy-2-(8-hydroxy-2-oxo-1,2-dihydroquinolin-5-yl)ethyl)amino)pentyl)oxy)benzamido)-2,3-dihydro-1H-indene-2-carboxylate | Formate |
| 14 | 6.52 | 2 | $^1$H NMR (400 MHz, MeOD): δ 8.38 (d, J = 9.3 Hz, 1H), 7.66 (d, J = 3.1 Hz, 1H), 7.34-7.29 (m, 6H), 7.05 (d, J = 8.2 Hz, 1H), 6.63 (d, J = 9.5 Hz, 1H), 5.41 (t, J = 7.8 Hz, 1H), 5.33 (s, 1H), 4.61 (s, 2H), 3.87-3.70 (m, 3H), 3.64 (d, J = 16.6 Hz, 2H), 3.43 (dd, J = 6.3, 6.3 Hz, 2H), 3.29-3.21 (m, 6H), 3.16 (dd, J = 7.3, 7.3 Hz, 2H), 2.83-2.74 (m, 1H), 2.32 (s, 1H), 2.07-1.88 (m, 2H), 1.82-1.81 (m, 2H), 1.77-1.65 (m, 3H), 1.46 (t, J = 13.0 Hz, 1H). | 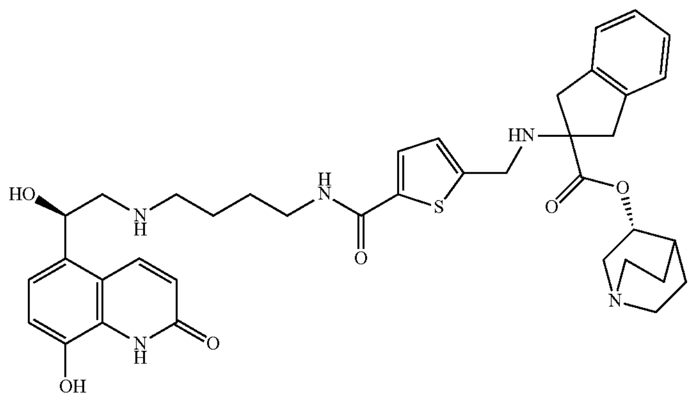 [SMILES: O=C(NCCCCNC[C@H](O)c1ccc(O)c2[nH]c(=O)ccc12)c1ccc(CNC2(C(=O)O[C@H]3CN4CCC3CC4)Cc3ccccc3C2)s1] | (R)-quinuclidin-3-yl 2-((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-2-carboxylate | TFA |

-continued

| No | R$_t$ (min) | Method | NMR data | Structure | Chemical name | Salt Two equiv. |
|---|---|---|---|---|---|---|
| 15 | 7.25 | 2 | $^1$H NMR (400 MHz, DMSO-d$_6$): δ 10.52 (s, 1H), 10.47 (s, 1H), 9.54-9.54 (m, 1H), 8.51-8.51 (m, 2H), 8.18 (d, J = 9.9 Hz, 1H), 7.60 (d, J = 8.2 Hz, 2H), 7.45 (dd, J = 7.5, 7.5 Hz, 2H), 7.38 (d, J = 5.4 Hz, 5H), 7.30 (dd, J = 3.1, 5.3 Hz, 2H), 7.15 (d, J = 8.3 Hz, 1H), 7.09 (s, 1H), 7.03 (d, J = 1.4 Hz, 1H), 6.98 (d, J = 8.2 Hz, 1H), 6.80 (s, 1H), 6.59 (dd, J = 2.2, 9.9 Hz, 1H), 6.16 (d, J = 3.3 Hz, 1H), 5.32-5.29 (m, 1H), 5.01-4.99 (m, 1H), 4.13 (s, 1H), 4.02 (dd, J = 6.3, 6.3 Hz, 2H), 3.89-3.72 (m, 3H), 3.60 (dd, J = 8.9, 14.1 Hz, 1H), 3.14-2.95 (m, 9H), 2.49-2.38 (m, 3H), 2.12 (d, J = 20.1 Hz, 1H), 1.86-1.67 (m, 9H), 1.59 (s, 2H), 1.47 (dd, J = 7.2, 14.9 Hz, 2H). | 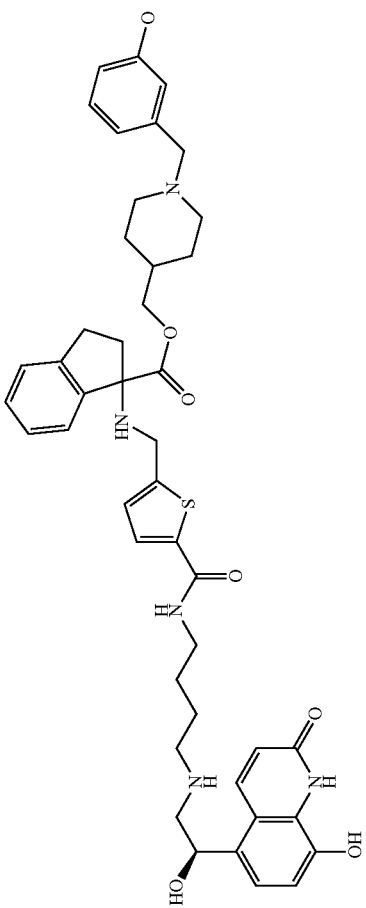 | (1-(3-hydroxybenzyl)piperidin-4-yl)methyl 1-(((5-(((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate | TFA |
| 16 | 6.74 | 2 | $^1$H NMR (400 MHz, MeOD): δ 8.50 (s, 2H), 8.37 (d, J = 9.8 Hz, 1H), 7.50 (d, J = 3.8 Hz, 1H), 7.43 (s, 5H), 7.37 (d, J = 7.5 Hz, 1H), 7.32-7.28 (m, 3H), 7.27-7.20 (m, 1H), 7.04 (d, J = 8.2 Hz, 1H), 6.96 (d, J = 3.8 Hz, 1H), 6.68 (d, J = 9.9 Hz, 1H), 5.41 (t, J = 6.0 Hz, 1H), 4.03-3.95 (m, 4H), 3.88 (s, 2H), 3.42 (t, J = 7.9 Hz, 2H), 3.26-3.08 (m, 8H), 2.77-2.67 (m, 1H), 2.61-2.59 (m, 2H), 2.31-2.22 (m, 1H), 1.84-1.68 (m, 7H), 1.47-1.35 (m, 2H). | 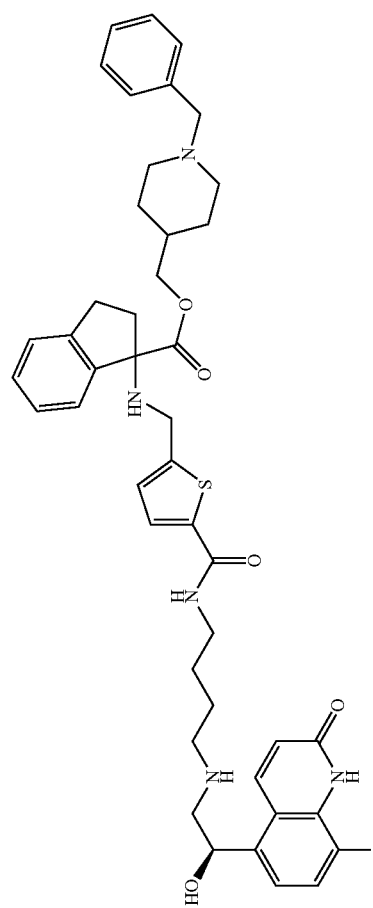 | (1-benzylpiperidin-4-yl)methyl 1-(((5-(((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate | Formate |

-continued

| No | R, (min) | Method | NMR data | Structure | Chemical name | Salt Two equiv. |
|---|---|---|---|---|---|---|
| 17 | 6.70 | 2 | 1H NMR (400 MHz, MeOD): δ 8.37 (dd, J = 2.4, 9.9 Hz, 1H), 7.66-7.61 (m, 2H), 7.57 (d, J = 7.5 Hz, 1H), 7.4 (d, J = 6.1 Hz, 2H), 7.41-7.35 (m, 1H), 7.32-7.26 (m, 3H), 7.16 (dd, J = 3.6, 5.0 Hz, 1H), 7.05 (d, J = 8.2 Hz, 1H), 6.66 (d, J = 9.3 Hz, 1H), 5.42 (t, J = 6.2 Hz, 1H), 4.56-4.39 (m, 4H), 4.16 (d, J = 5.8 Hz, 2H), 3.55-3.48 (m, 2H), 3.43 (t, J = 4.6 Hz, 2H), 3.40-3.30 (m, 2H), 3.28-3.20 (m, 2H), 3.16 (t, J = 4.6 Hz, 2H), 3.06-2.94 (m, 3H), 2.70-2.62 (m, 1H), 2.04-1.94 (m, 1H), 1.85-1.69 (m, 6H), 1.47 (s, 2H). | [structure] | (1-(thiophen-2-ylmethyl)piperidin-4-yl)methyl 1-(((5-(((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate | TFA |
| 18 | 6.99 | 2 | 1H NMR (400 MHz, DMSO-d6, 90° C.): δ 10.05-9.80 (m, 2H), 8.78 (s, 1H), 6.54 (d, J = 9.9 Hz, 1H), 8.09 (d, J = 8.7 Hz, 2H), 7.48-7.43 (m, 3H), 7.33-7.25 (m, 6H), 7.12 (d, J = 8.3 Hz, 1H), 6.99 (d, J = 9.9 Hz, 1H), 6.54 (d, J = 9.9 Hz, 1H), 5.33 (dd, J = 4.9, 8.2 Hz, 1H), 4.87-4.84 (m, 1H), 4.19 (d, J = 2.4 Hz, 2H), 3.65 (s, 2H), 3.60-3.44 (m, 4H), 3.22-2.86 (m, 8H), 2.71-2.64 (m, 1H), 2.17-2.10 (m, 2H), 1.83-1.68 (m, 3H), 1.62-1.56 (m, 1H). | [structure] | (R)-quinuclidin-3-yl 1-(2-(4-(2-((((R)-2-(8-hydroxy-2-oxo-1,2-dihydroquinolin-5-yl)ethyl)amino)methyl)phenyl)amino)-2-oxoethyl)phenyl)acetamido)-2,3-dihydro-1H-indene-1-carboxylate | TFA |
| 19 | 7.12 | 2 | 1H NMR (400 MHz, MeOD): δ 8.24 (dd, J = 2.6, 9.9 Hz, 1H), 7.88 (dd, J = 9.2, 9.2 Hz, 2H), 7.62-7.56 (m, 5H), 7.38-7.27 (m, 4H), 7.12-7.08 (m, 2H), 7.04 (d, J = 8.2 Hz, 1H), 6.65 (d, J = 9.9 Hz, 1H), 5.41 (dd, J = 6.7, 6.7 Hz, 1H), 5.22 (s, 2H), 5.13-5.03 (m, 1H), 4.35 (s, 2H), 3.77-3.68 (m, 1H), 3.44 (d, J = 11.4 Hz, 1H), 3.30-3.22 (m, 6H), 3.16-3.10 (m, 3H), 2.41-2.26 (m, 2H), 2.08-1.80 (m, 4H). | [structure] | (R)-quinuclidin-3-yl 1-(4-(4-((((R)-2-hydroxy-2-(8-hydroxy-2-oxo-1,2-dihydroquinolin-5-yl)ethyl)amino)methyl)benzyl)oxy)benzamido)-2,3-dihydro-1H-indene-1-carboxylate | TFA |

-continued

| No | R_t (min) | Method | NMR data | Structure | Chemical name | Salt Two equiv. |
|----|-----------|--------|----------|-----------|---------------|-----------------|
| 20 | 7.07 | 2 | ¹H NMR (400 MHz, MeOD): δ 8.45 (s, 2H), 8.23 (dd, J = 3.1, 9.9 Hz, 1H), 7.59-7.51 (m, 4H), 7.45 (dd, J = 7.3, 15.4 Hz, 1H), 7.35-7.22 (m, 5H), 7.06-7.02 (m, 2H), 6.98-6.90 (m, 2H), 6.65 (d, J = 9.8 Hz, 1H), 5.39 (dd, J = 6.7, 6.7 Hz, 1H), 5.15 (s, 2H), 5.08-5.01 (m, 1H), 4.29 (s, 2H), 3.69 (d, J = 3.5 Hz, 2H), 3.67-3.49 (m, 1H), 3.22-3.21 (m, 1H), 3.21-3.12 (m, 7H), 2.94-2.77 (m, 2H), 2.40-2.24 (m, 3H), 2.03-1.68 (m, 3H), 1.66-1.61 (m, 1H). | 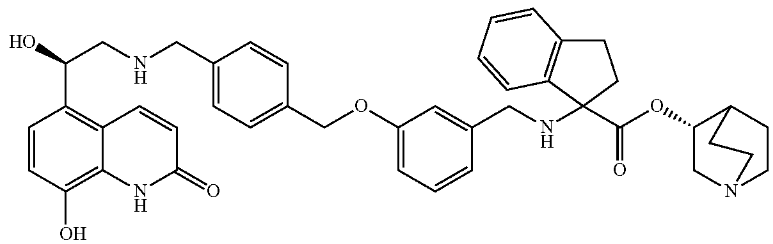 [SMILES: O=C(O[C@H]1CN2CCC1CC2)C1(NCc2cccc(OCc3ccc(CNC[C@H](O)c4ccc(O)c5[nH]c(=O)ccc45)cc3)c2)CCc2ccccc21] | (R)-quinuclidin-3-yl 1-(3-((4-((((R)-2-hydroxy-2-(8-hydroxy-2-oxo-1,2-dihydroquinolin-5-yl)ethyl)amino)methyl)benzyl)oxy)benzyl)amino)-2,3-dihydro-1H-indene-1-carboxylate | TFA |
| 21 | 2.34 | 4 | ¹H NMR (400 MHz, MeOD): δ 8.38 (d, J = 9.9 Hz, 1H), 7.64 (dd, J = 7.8, 15.8 Hz, 1H), 7.56-7.51 (m, 2H), 7.46-7.37 (m, 2H), 7.32-7.28 (m, 2H), 7.18 (s, 1H), 7.10 (d, J = 7.9 Hz, 2H), 7.06-7.02 (m, 3H), 6.92 (dd, J = 1.9, 7.3 Hz, 1H), 6.68 (d, J = 9.8 Hz, 1H), 5.42 (t, J = 6.7 Hz, 1H), 5.36-5.26 (m, 1H), 5.09 (s, 2H), 4.33-4.17 (m, 2H), 4.09 (t, J = 4.0 Hz, 2H), 3.81-3.71 (m, 1H), 3.51-3.35 (m, 3H), 3.29-2.96 (m, 8H), 2.87-2.69 (m, 2H), 2.46 (br s, 0.5H), 2.23 (br s, 0.5H), 2.14-1.82 (m, 6H), 1.69-1.60 (m, 1H), 1.34-1.24 (m, 1H). | 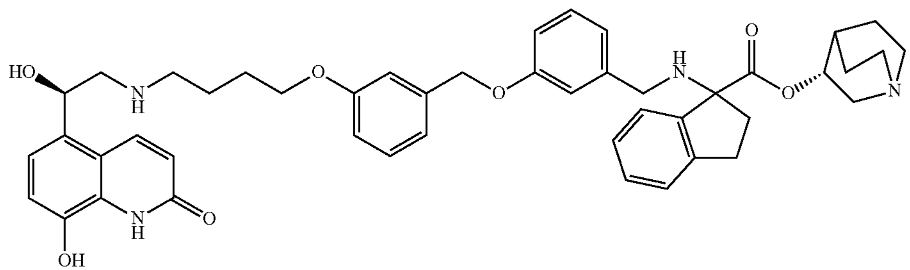 [SMILES: O=C(O[C@H]1CN2CCC1CC2)C1(NCc2cccc(OCc3cccc(OCCCCNC[C@H](O)c4ccc(O)c5[nH]c(=O)ccc45)c3)c2)CCc2ccccc21] | (R)-quinuclidin-3-yl 1-((3-(4-(((R)-2-hydroxy-2-(8-hydroxy-2-oxo-1,2-dihydroquinolin-5-yl)ethyl)amino)butoxy)benzyl)amino)-2,3-dihydro-1H-indene-1-carboxylate | TFA |
| 22 | 2.27 | 4 | ¹H NMR (400 MHz, MeOD): δ 8.55 (s, 1H), 8.37 (d, J = 9.9 Hz, 1H), 7.50 (d, J = 3.8 Hz, 1H), 7.40-7.32 (m, 6H), 7.31-7.27 (m, 3H), 7.27-7.20 (m, 1H), 7.04 (d, J = 8.2 Hz, 1H), 6.96 (d, J = 3.9 Hz, 1H), 6.68 (d, J = 9.9 Hz, 1H), 5.38 (t, J = 7.6 Hz, 1H), 4.04-3.93 (m, 2H), 3.88 (s, 2H), 3.69 (s, 2H), 3.42 (t, J = 6.3 Hz, 2H), 3.21 (d, J = 6.4 Hz, 2H), 3.15-3.07 (m, 4H), 3.02-2.97 (m, 2H), 2.78-2.67 (m, 1H), 2.31-2.18 (m, 3H), 1.82-1.56 (m, 7H), 1.39-1.25 (m, 2H). | 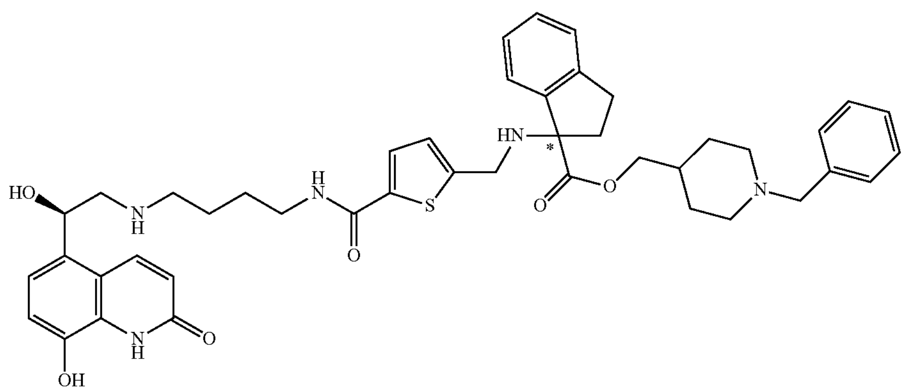 [SMILES: O=C(NCCCCNC[C@H](O)c1ccc(O)c2[nH]c(=O)ccc12)c1ccc(CNC2(C(=O)OCC3CCN(Cc4ccccc4)CC3)CCc3ccccc32)s1] | (1-benzylpiperidin-4-yl)methyl 1-((5-(((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate single diastereoisomer 1 | Formate |

| No | R_t (min) | Method | NMR data | Structure | Chemical name | Salt Two equiv. |
|---|---|---|---|---|---|---|
| 23 | 2.28 | 4 | $^1$H NMR (400 MHz, MeOD); δ 8.37 (d, J = 9.8 Hz, 1H), 7.63 (d, J = 3.8 Hz, 1H), 7.57 (d, J = 7.7 Hz, 1H), 7.49 (d, J = 1.1 Hz, 7H), 7.42-7.37 (m, 1H), 7.32-7.27 (m, 2H), 7.05 (d, J = 8.2 Hz, 1H), 6.65 (d, J = 9.9 Hz, 1H), 5.41 (t, J = 6.7 Hz, 1H), 4.50 (dd, J = 13.5, 35.0 Hz, 2H), 4.28 (s, 2H), 4.16 (d, J = 6.1 Hz, 2H), 3.50-3.40 (m, 4H), 3.39-3.33 (m, 2H), 3.31-3.25 (m, 2H), 3.24-3.13 (m, 2H), 3.06-2.91 (m, 3H), 2.71-2.62 (m, 1H), 1.96-1.95 (m, 1H), 1.82-1.69 (m, 6H), 1.50-1.39 (m, 2H). | 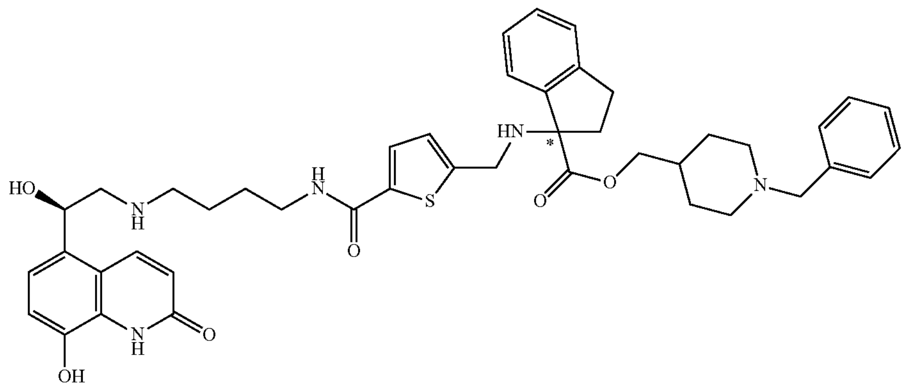 [SMILES: O=C(NCCCCNC[C@H](O)c1ccc(O)c2[nH]c(=O)ccc12)c1ccc(CNC2(C(=O)OCC3CCN(Cc4ccccc4)CC3)CCc3ccccc32)s1] | (1-benzylpiperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate single stereoisomer 2 | TFA |
| 24 | 2.28 | 4 | $^1$H NMR (400 MHz, DMSO-d$_6$, 90° C.); δ 8.23 (d, J = 9.9 Hz, 1H), 8.08-8.06 (m, 1H), 7.56 (d, J = 3.3 Hz, 1H), 7.52 (s, 5H), 7.45 (d, J = 7.6 Hz, 1H), 7.36 (d, J = 4.0 Hz, 2H), 7.31-7.27 (d, J = 8.1 Hz, 1H), 7.20 (d, J = 8.1 Hz, 1H), 7.07 (d, J = 8.1 Hz, 1H), 6.97 (d, J = 3.8 Hz, 1H), 6.61 (d, J = 9.9 Hz, 1H), 5.39 (dd, J = 5.1, 7.1 Hz, 1H), 5.06-5.02 (m, 1H), 4.23 (s, 2H), 3.99-3.89 (m, 2H), 3.37-3.27 (m, 2H), 3.22-3.00 (m, 10H), 2.74-2.67 (m, 1H), 2.34-2.25 (m, 1H), 2.15-2.05 (m, 2H), 1.97-1.84 (m, 1H), 1.83-1.74 (m, 3H), 1.71-1.63 (m, 2H). | 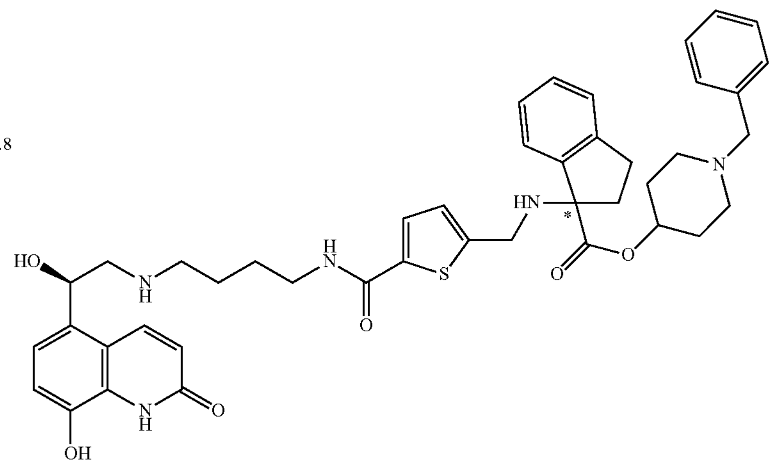 | 1-benzylpiperidin-4-yl1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate single stereoisomer 1 | TFA |

| No | R_t (min) | Method | NMR data | Structure | Chemical name | Salt Two equiv. |
|---|---|---|---|---|---|---|
| 25 | 2.33 | 4 | ¹H NMR (400 MHz, DMSO-d₆); δ 8.33 (t, J = 5.6 Hz, 1H), 8.17 (d, J = 9.9 Hz, 1H), 7.53 (d, J = 3.8 Hz, 1H), 7.39 (d, J = 7.4 Hz, 1H), 7.30-7.20 (m, 8H), 7.04 (d, J = 8.3 Hz, 1H), 6.90-6.85 (m, 2H), 6.48 (d, J = 9.8 Hz, 1H), 4.99 (dd, J = 4.3, 8.0 Hz, 1H), 4.76-4.72 (m, 1H), 3.84-3.76 (m, 2H), 3.50-3.39 (m, 2H), 3.31-3.16 (m, 4H), 3.03-2.90 (m, 3H), 2.70-2.54 (m, 3H), 2.39-2.33 (m, 1H), 2.25-2.09 (m, 3H), 1.73-1.69 (m, 2H), 1.54-1.39 (m, 6H). | 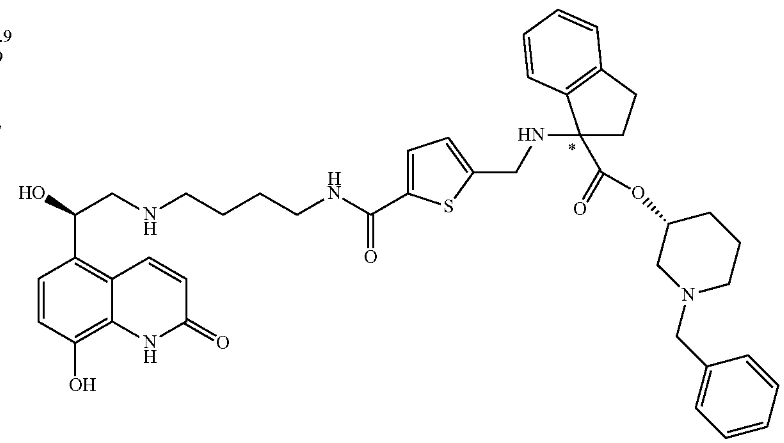 | (R)-1-benzylpiperidin-3-yl 1-((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate single stereoisomer 1 | Free Base |
| 26 | 2.30 | 4 | ¹H NMR (400 MHz, DMSO-d₆, 100° C.); δ 8.33 (t, J = 5.6 Hz, 1H), 8.17 (d, J = 9.9 Hz, 1H), 7.53 (d, J = 3.8 Hz, 1H), 7.39 (d, J = 7.4 Hz, 1H), 7.30-7.20 (m, 8H), 7.04 (d, J = 8.3 Hz, 1H), 6.90-6.85 (m, 2H), 6.48 (d, J = 9.8 Hz, 1H), 4.99 (dd, J = 4.3, 8.0 Hz, 1H), 3.84-3.76 (m, 2H), 3.50-3.39 (m, 2H), 3.31-3.16 (m, 4H), 3.03-2.90 (m, 3H), 2.70-2.54 (m, 3H), 2.39-2.33 (m, 1H), 2.25-2.09 (m, 3H), 1.73-1.69 (m, 2H), 1.54-1.39 (m, 4H). | 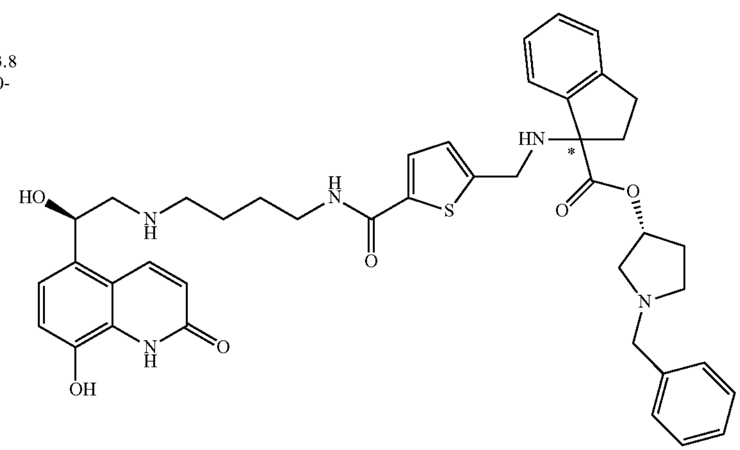 | (R)-1-benzylpyrrolidin-3-yl 1-((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate single stereoisomer 1 | TFA |

| No | $R_t$ (min) | Method | NMR data | Structure | Chemical name | Salt Two equiv. |
|---|---|---|---|---|---|---|
| 27 | 2.26 | 4 | ¹H NMR (400 MHz, DMSO-d₆): δ 8.42 (dd, J = 5.6, 5.6 Hz, 1H), 8.34 (s, 2H), 8.23 (d, J = 9.9 Hz, 1H), 7.59 (d, J = 3.8 Hz, 1H), 7.44 (d, J = 7.3 Hz, 1H), 7.38-7.25 (m, 8H), 7.16 (d, J = 8.3 Hz, 1H), 7.01 (d, J = 8.1 Hz, 1H), 6.96 (d, J = 3.5 Hz, 1H), 6.58 (d, J = 9.9 Hz, 1H), 5.26 (dd, J = 4.0, 8.6 Hz, 1H), 4.84-4.78 (m, 1H), 3.86 (s, 2H), 3.46 (s, 2H), 3.30-3.22 (m, 3H), 3.09-2.83 (m, 6H), 2.49-2.45 (m, 1H), 2.40-2.15 (m, 4H), 1.85-1.75 (m, 2H), 1.64-1.53 (m, 7H). | 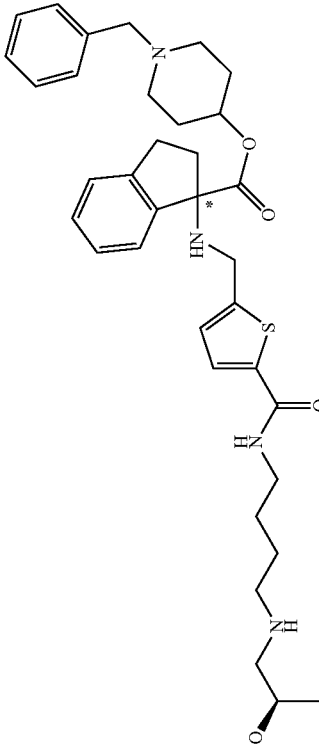 | 1-benzylpiperidin-4-yl 1-((5-((4-(((R)-2-hydroxy-2-(8-hydroxy-2-oxo-1,2-dihydroquinolin-5-yl)ethyl)amino)butyl)carbamoyl)thiophen-2-yl)methylamino)-2,3-dihydro-1H-indene-1-carboxylate single stereoisomer 2 | TFA |
| 28 | 2.31 | 4 | ¹H NMR (400 MHz, DMSO-d₆ 90° C.): δ 8.14 (d, J = 9.9 Hz, 1H), 8.06 (s, 1H), 7.48 (d, J = 3.6 Hz, 1H), 7.42 (s, 6H), 7.30-7.26 (m, 2H), 7.23-7.19 (m, 1H), 7.12 (d, J = 8.2 Hz, 1H), 6.98 (d, J = 8.2 Hz, 1H), 6.90 (d, J = 3.5 Hz, 1H), 6.53 (d, J = 9.9 Hz, 1H), 5.35-5.29 (m, 2H), 4.28-4.19 (m, 2H), 3.92-3.82 (m, 2H), 3.28-3.22 (m, 6H), 3.11-2.98 (m, 6H), 2.69-2.61 (m, 1H), 2.43-2.28 (m, 1H), 2.27-2.19 (m, 1H), 1.97 (s, 1H), 1.71-1.66 (m, 2H), 1.62-1.54 (m, 2H). | 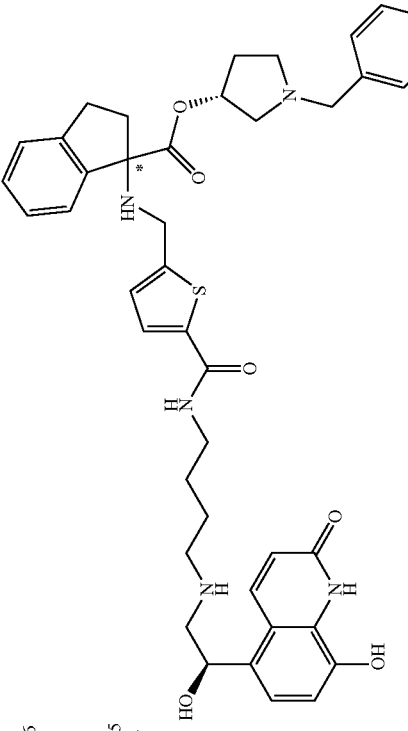 | (R)-1-benzylpyrrolidin-3-yl 1-((5-((4-(((R)-2-hydroxy-2-(8-hydroxy-2-oxo-1,2-dihydroquinolin-5-yl)ethyl)amino)butyl)carbamoyl)thiophen-2-yl)methylamino)-2,3-dihydro-1H-indene-1-carboxylate single stereoisomer 2 | TFA |

Biological Characterization

Example. M3 Receptor Radioligand Binding Assay

Human M3 receptor membranes (15 ug/well) from Perkin Elmer were incubated with 0.52 nM Scopolamine Methyl Chloride, [N-methyl-3H] with or without test compounds, or a saturating concentration of Atropine (5 µM) for the determination of non-specific binding. The assay was carried out in 96-well polypropylene plates in a volume of 250 ul. The assay buffer used was 50 mM Tris-HCl, 154 mM NaCl (pH 7.4). The final assay concentration of DMSO was 0.5% (v/v). The plates were sealed and incubated for 2 hours at room temperature on an orbital shaker (slow speed). Membranes were harvested onto 96-well unifilter GF/C filter plates pre-treated with 0.5% polyethyleneimine (v/v), using a filter manifold, washed four times with 200 µl of assay buffer. The plates were dried before addition of 50 µl of microscint-0, sealed then read in a Trilux Microbeta scintillation counter. IC50 values are determined from competition curves using a non-linear curve fitting program. Ki values were calculated from IC50 values by the Cheng and Prusoff equation.

The Ki values of the compounds according to the invention are less than 50 nM, most of them even less than 10 nM.

Example. β2 Adrenoceptor Radioligand Binding Assay

Human $\beta_2$ adrenoceptor membranes (7.5 ug/well) from Perkin Elmer were incubated with 0.3 nM 125-I Cyanopindolol with or without test compounds, or a saturating concentration of s-propranolol (2 µM) for the determination of non-specific binding. The assay was carried out in 96-well polypropylene plates in a volume of 200 ul. The assay buffer used was 25 mM HEPES, 0.5% BSA (w/v), 1 mM EDTA, 0.02% ascorbic acid (v/v), (pH 7.4). The final assay concentration of DMSO was 0.5% (v/v). The plates were sealed and incubated for 1 hour at room temperature on an orbital shaker (slow speed). Membranes were harvested onto 96-well unifilter GF/C filter plates pre-treated with 0.5% polyethyleneimine (v/v), using a filter manifold, washed six times with 200 µl of wash buffer containing 10 mM HEPES and 500 mM NaCl. The plates were dried before addition of 50 µl of microscint-0, sealed then read in a Trilux Microbeta scintillation counter. IC50 values are determined from competition curves using a non-linear curve fitting program. Ki values were calculated from IC50 values by the Cheng and Prusoff equation.

The Ki values of the compounds according to the invention are less than 50 nM, most of them even less than 10 nM.

In the following table the compounds tested are classified in terms of binding affinity according to the following ranges:
+++: Ki<1 nM
++: Ki in the range 1-10 nM
+: Ki>10 nM

| Compound Number | M3 | B2 |
|---|---|---|
| 1 | +++ | +++ |
| 2 | +++ | +++ |
| 3 | +++ | +++ |
| 4 | +++ | +++ |
| 5 | +++ | +++ |
| 6 | +++ | ++ |
| 7 | +++ | + |
| 8 | ++ | + |
| 9 | +++ | + |
| 10 | ++ | + |
| 11 | ++ | + |
| 12 | ++ | + |
| 5A | ++ | ++ |
| 5B | +++ | +++ |
| 13 | +++ | ++ |
| 14 | +++ | ++ |
| 15 | +++ | ++ |
| 16 | +++ | ++ |
| 17 | +++ | + |
| 18 | ++ | + |
| 19 | ++ | + |
| 20 | ++ | +++ |
| 21 | +++ | +++ |
| 22 | +++ | ++ |
| 23 | +++ | ++ |
| 24 | +++ | + |
| 25 | +++ | + |
| 26 | + | + |
| 27 | +++ | + |
| 28 | +++ | ++ |

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

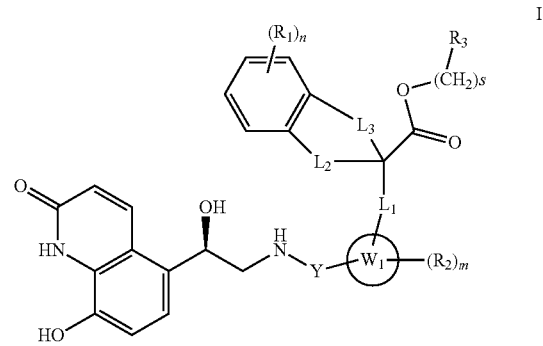

wherein
Y is a divalent group of formula

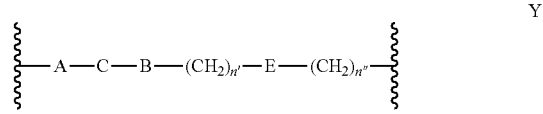

wherein
A is $(C_1\text{-}C_6)$alkylene;
B is absent or is $(C_3\text{-}C_8)$cycloalkylene, $(C_3\text{-}C_8)$heterocycloalkylene, arylene or heteroarylene optionally substituted by one or more groups selected from the group consisting of halogen, —CN, $(C_1\text{-}C_6)$alkyl, $(C_1\text{-}C_6)$alkoxy, and aryl $(C_1\text{-}C_6)$alkyl;
C is absent or is —O—, —C(O)—, —OC(O)—, —(O)CO—, —S—, —S(O)—, —S(O)$_2$—, or —N(R$_5$)—
n' n" are at each occurrence independently 0 or an integer from 1 to 3;
E is absent or is —O—, —NR$_5$—, —NR$_5$—C(O)—, —C(O)—NR$_5$—, —OC(O)—, or —S—;
W$_1$ is a divalent arylene or a divalent heteroarylene group;
R$_1$ and R$_2$, when present, are at each occurrence independently halogen, $(C_1\text{-}C_6)$alkyl, or $(C_1\text{-}C_6)$alkoxy;
n and m are in each occurrence independently 0 or an integer ranging from 1 to 3;
L$_1$ is —(CH$_2$)$_t$—NR$_5$—, —(CH$_2$)$_t$—C(O)—NR$_5$—, or —C(O)—NR$_5$—(CH$_2$)$_t$—C(O)—NR$_5$—; wherein t is an integer ranging from 0 to 4;
L$_2$ is —(CH$_2$)$_q$— and L$_3$ is —(CH$_2$)$_{2-q}$—; wherein q is an integer ranging from 0 to 2;
s is an integer ranging from 0 to 3,
R$_3$ is a nitrogen containing group of formulae J1, J2, J3, or J4:

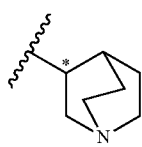

J1

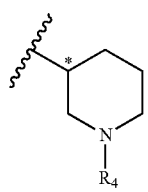

J2

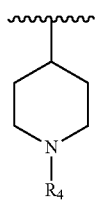

J3

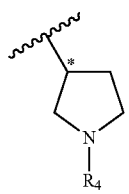

J4

R$_4$ is a group of formula K

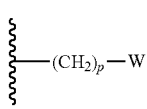

K wherein p is 0 or an integer from 1 to 4; and W is H, $(C_1\text{-}C_6)$alkyl, $(C_3\text{-}C_8)$cycloalkyl, aryl, or heteroaryl, optionally substituted by one or more substituents selected independently from the group consisting of a halogen atom, —OH, oxo (═O), and —SH;
R$_5$ is at each occurrence independently H, linear or branched $(C_1\text{-}C_6)$alkyl, $(C_3\text{-}C_8)$cycloalkyl, $(C_3\text{-}C_8)$heterocycloalkyl, aryl, or heteroaryl;
or a pharmaceutically acceptable salt thereof.

2. A compound or pharmaceutically acceptable salt according to claim 1, wherein R$_3$ is a group of formula J1:

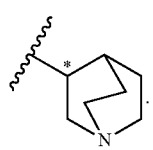

J1

3. A compound or pharmaceutically acceptable salt according to claim 2, wherein R$_3$ is a group of formula J1 which has an absolute configuration is R.

4. A compound or pharmaceutically acceptable salt according to claim 1, wherein R$_3$ is a nitrogen containing group selected from J2, J3 or J4

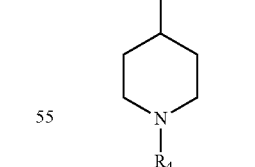

J2

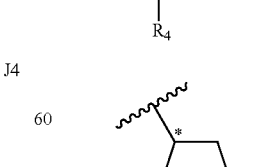

J3

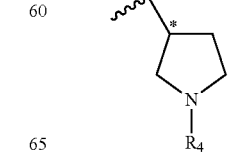

J4 wherein R₄ is a group of formula K

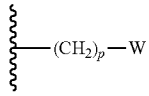

wherein p is 0 or 1 and W is H or is selected from the group consisting of (C₁-C₆)alkyl, (C₃-C₈)cycloalkyl aryl and heteroaryl optionally substituted by hydroxyl.

5. A compound or pharmaceutically acceptable salt according to claim 3, wherein R₃ is a group of formula J3 and R₄ is benzyl optionally substituted by —OH.

6. A compound or pharmaceutically acceptable salt according to claim 1, wherein q is 0 or 2 which is a compound of formula Ia:

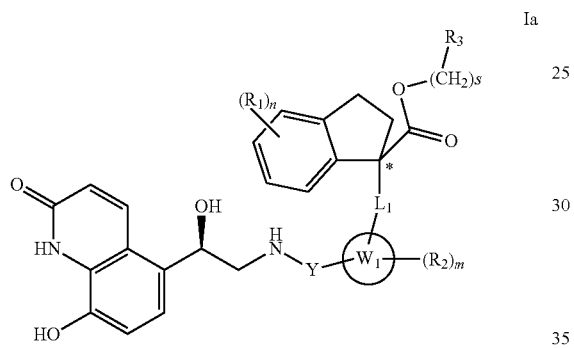

wherein
Y is a divalent group of formula

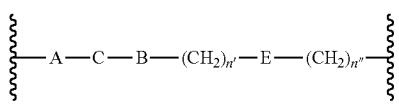

wherein
A is methylene, butylene, pentylene, or hexylene;
B is absent or is phenylene;
C is absent or is —O—;
n' and n" are at each occurrence independently 0 or 1;
E is absent or is —O—, —NR₅—C(O)—, or —C(O)—NR₅—;
W₁ is phenylene or thiophenediyl;
R₁, when present, is methyl; R₂, when present, is methoxyl; n and m are in each occurrence independently 0 or 1;
L₁ is —CH₂—NH—, —C(O)—NH—, CH₂—C(O)—NH— or —C(O)—NH—(CH₂)₂—C(O)—NH—;
s is 0 or 1;
R₃ is a nitrogen containing group of formulae J1, J2, J3, J4:

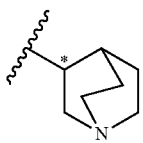

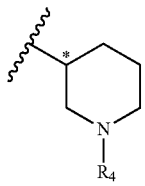

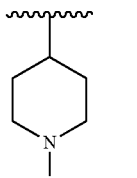

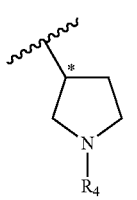

R₄ is a group of formula K

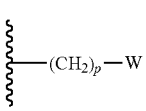

wherein p is 0 or 1; and
W is H, isopropyl, cyclopentyl, phenyl, thienyl, or furanyl, optionally substituted by an —OH;
R₅ is at each occurrence H;
or a pharmaceutically acceptable salt thereof.

7. A compound or pharmaceutically acceptable salt according to claim 1, wherein q is 1 which is a compound of formula Ib:

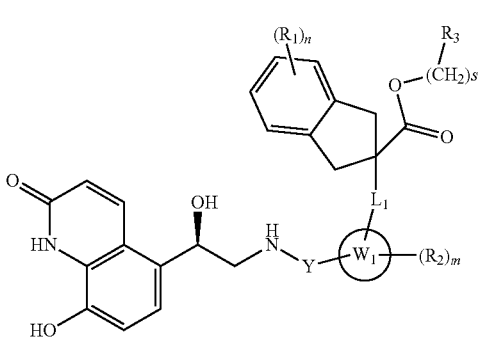

wherein
Y is a divalent group of formula

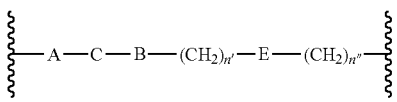

wherein
A is butylene or pentylene;
B is absent;
C is absent;
n' n" are 0;
E is —O— or —NR$_5$—C(O)—;
W$_1$ is phenylene or thiophenediyl;
n and m are 0;
L$_1$ is —(CH$_2$)$_t$—NR$_5$— wherein t is 1 or —(CH$_2$)$_t$—C(O)—NR$_5$— wherein t is 0;
s is 0,
R$_3$ is a nitrogen containing group of formula J1:

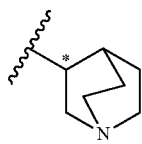

R$_5$ is in each occurrence H;
or a pharmaceutically acceptable salt thereof.

8. A compound or pharmaceutically acceptable salt according to claim 7, wherein R$_3$ is a group of formula J1 which has an absolute configuration is R.

9. A compound or pharmaceutically acceptable salt according to claim 1, which exists as a single optical stereoisomer, a diastereoisomer, or a mixture thereof, in any proportion.

10. A compound or pharmaceutically acceptable salt according to claim 1, which is a compound selected from the group consisting of:

(R)-quinuclidin-3-yl 1-((3-((4-(((R)-2-hydroxy-2-(8-hydroxy-2-oxo-1,2-dihydroquinolin-5-yl)ethyl)amino)butyl)carbamoyl)benzyl)amino)-2,3-dihydro-1H-indene-1-carboxylate;

(R)-quinuclidin-3-yl 1-(3-((5-(((R)-2-hydroxy-2-(8-hydroxy-2-oxo-1,2-dihydroquinolin-5-yl)ethyl)amino)pentyl)oxy)benzamido)-2,3-dihydro-1H-indene-1-carboxylate;

(R)-quinuclidin-3-yl 1-(3-((5-(((R)-2-hydroxy-2-(8-hydroxy-2-oxo-1,2-dihydroquinolin-5-yl)ethyl)amino)pentyl)oxy)benzyl)amino)-2,3-dihydro-1H-indene-1-carboxylate;

(R)-quinuclidin-3-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate;

(R)-quinuclidin-3-yl 1-((3-((4-(((R)-2-hydroxy-2-(8-hydroxy-2-oxo-1,2-dihydroquinolin-5-yl)ethyl)amino)butyl)carbamoyl)benzyl)amino)-4-methyl-2,3-dihydro-1H-indene-1-carboxylate;

(R)-quinuclidin-3-yl 1-(3-((5-(((R)-2-hydroxy-2-(8-hydroxy-2-oxo-1,2-dihydroquinolin-5-yl)ethyl)amino)pentyl)oxy)benzamido)-4-methyl-2,3-dihydro-1H-indene-1-carboxylate;

(R)-quinuclidin-3-yl 1-(3-(4-(((R)-2-hydroxy-2-(8-hydroxy-2-oxo-1,2-dihydroquinolin-5-yl)ethyl)amino)butoxy)benzamido)-2,3-dihydro-1H-indene-1-carboxylate;

(1-isopropylpiperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate;

(R)-quinuclidin-3-yl 1-(3-((4-(((R)-2-hydroxy-2-(8-hydroxy-2-oxo-1,2-dihydroquinolin-5-yl)ethyl)amino)butyl)carbamoyl)benzamido)-2,3-dihydro-1H-indene-1-carboxylate;

(1-benzylpiperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate;

(1-(furan-2-ylmethyl)piperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate;

(1-(3-hydroxybenzyl)piperidin-4-yl)methyl 1-(3-((6-(((R)-2-hydroxy-2-(8-hydroxy-2-oxo-1,2-dihydroquinolin-5-yl)ethyl)amino)hexyl)oxy)benzamido)-2,3-dihydro-1H-indene-1-carboxylate;

(R)-quinuclidin-3-yl 1-(3-((4-(((R)-2-hydroxy-2-(8-hydroxy-2-oxo-1,2-dihydroquinolin-5-yl)ethyl)amino)butoxy)methyl)benzamido)-2,3-dihydro-1H-indene-1-carboxylate;

(R)-quinuclidin-3-yl 2-(3-((5-(((R)-2-hydroxy-2-(8-hydroxy-2-oxo-1,2-dihydroquinolin-5-yl)ethyl)amino)pentyl)oxy)benzamido)-2,3-dihydro-1H-indene-2-carboxylate;

(R)-quinuclidin-3-yl 2-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-2-carboxylate;

(1-(3-hydroxybenzyl)piperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate;

(1-benzylpiperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate;

(1-(thiophen-2-ylmethyl)piperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate;

(R)-quinuclidin-3-yl 1-(2-(4-(2-((4-((((R)-2-hydroxy-2-(8-hydroxy-2-oxo-1,2-dihydroquinolin-5-yl)ethyl)amino)methyl)phenyl)amino)-2-oxoethyl)phenyl)acetamido)-2,3-dihydro-1H-indene-1-carboxylate;

(R)-quinuclidin-3-yl 1-(4-((4-((((R)-2-hydroxy-2-(8-hydroxy-2-oxo-1,2-dihydroquinolin-5-yl)ethyl)amino)methyl)benzyl)oxy)benzamido)-2,3-dihydro-1H-indene-1-carboxylate;

(R)-quinuclidin-3-yl 1-((3-((4-((((R)-2-hydroxy-2-(8-hydroxy-2-oxo-1,2-dihydroquinolin-5-yl)ethyl)amino)methyl)benzyl)oxy)benzyl)amino)-2,3-dihydro-1H-indene-1-carboxylate;

(R)-quinuclidin-3-yl 1-((3-((3-(4-(((R)-2-hydroxy-2-(8-hydroxy-2-oxo-1,2-dihydroquinolin-5-yl)ethyl)amino)butoxy)benzyl)oxy)benzyl)amino)-2,3-dihydro-1H-indene-1-carboxylate;

(1-benzylpiperidin-4-yl)methyl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-H-indene-1-carboxylate;

1-benzylpiperidin-4-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate;

(R)-1-benzylpiperidin-3-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate; and (R)-1-benzylpyrrolidin-3-yl 1-(((5-((4-(((R)-2-hydroxy-2-(8-hydroxy-2-oxo-1,2-dihydroquinolin-5-yl)ethyl)amino)butyl)carbamoyl)thiophen-2-yl)methyl)amino)-2,3-dihydro-1H-indene-1-carboxylate;

or a pharmaceutically acceptable salt of said compound.

11. A pharmaceutical composition, comprising a compound or pharmaceutically acceptable salt according to claim 1 and one or more pharmaceutically acceptable carriers and/or excipients.

12. A pharmaceutical composition according to claim 11, which is in a form suitable to be administered by inhalation, selected from the group consisting of an inhalable powder, a propellant-containing metering aerosol, and a propellant-free inhalable formulation.

13. A pharmaceutical composition according to claim 11, which is an inhalable powder, a propellant-containing metering aerosol, or a propellant-free inhalable formulation.

14. A method for the prevention and/or treatment of a broncho-obstructive or inflammatory disease, comprising administering to a subject in need thereof an effective amount of a compound or pharmaceutically acceptable salt according to claim 1.

15. A method for the prevention and/or treatment of asthma, chronic bronchitis, or chronic obstructive pulmonary disease, comprising administering to a subject in need thereof an effective amount of a compound or pharmaceutically acceptable salt according to claim 1.

16. A combination, comprising a compound or pharmaceutically acceptable salt according to claim 1 and one or more active ingredients selected from the group consisting of a corticosteroid, a P38 MAP kinase inhibitor, a IKK2 inhibitor, a HNE inhibitor, a PDE4 inhibitor, a leukotriene modulator, a NSAID, and a mucus regulatos.

17. A device, comprising a pharmaceutical composition according to claim 12, which is a single-dose dry powder inhaler, multi-dose dry powder inhaler, a metered dose inhaler, or a soft mist nebulizer.

* * * * *